United States Patent
Frattini et al.

(10) Patent No.: US 11,045,446 B2
(45) Date of Patent: Jun. 29, 2021

(54) CDC7 KINASE INHIBITORS AND USES THEREOF

(71) Applicant: SLOAN-KETTERING INSTITUTE FOR CANCER RESEARCH, New York, NY (US)

(72) Inventors: Mark G. Frattini, Ridgewood, NJ (US); Hakim Djaballah, Scarsdale, NY (US); Thomas J. Kelly, New York, NY (US)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

(21) Appl. No.: 16/189,780

(22) Filed: Nov. 13, 2018

(65) Prior Publication Data
US 2019/0314329 A1  Oct. 17, 2019

Related U.S. Application Data

(63) Continuation of application No. 15/728,609, filed on Oct. 10, 2017, now Pat. No. 10,123,992, which is a continuation of application No. 15/349,905, filed on Nov. 11, 2016, now Pat. No. 9,782,386, which is a continuation of application No. 14/936,472, filed on Nov. 9, 2015, now Pat. No. 9,492,427, which is a continuation of application No. 13/583,170, filed as application No. PCT/US2011/027619 on Mar. 8, 2011, now Pat. No. 9,180,105.

(Continued)

(51) Int. Cl.
| | |
|---|---|
| *C07D 493/08* | (2006.01) |
| *C07D 493/18* | (2006.01) |
| *A61K 31/122* | (2006.01) |
| *A61K 31/352* | (2006.01) |
| *A61K 31/365* | (2006.01) |
| *C09B 13/02* | (2006.01) |
| *C09B 61/00* | (2006.01) |
| *C12Q 1/6886* | (2018.01) |
| *A61N 5/10* | (2006.01) |
| *A61K 9/00* | (2006.01) |

(52) U.S. Cl.
CPC .......... *A61K 31/365* (2013.01); *A61K 9/0019* (2013.01); *A61K 31/122* (2013.01); *A61K 31/352* (2013.01); *A61N 5/10* (2013.01); *C07D 493/08* (2013.01); *C07D 493/18* (2013.01); *C09B 13/02* (2013.01); *C09B 61/00* (2013.01); *C12Q 1/6886* (2013.01); *C12Q 2600/106* (2013.01); *C12Q 2600/156* (2013.01)

(58) Field of Classification Search
CPC .. A61K 9/0019; A61K 31/122; A61K 31/352; A61K 31/365; C09B 61/00; C12Q 2600/106; C12Q 2600/156; C12Q 1/6886; A61N 5/10

USPC .......................................... 514/453, 454, 27
See application file for complete search history.

(56) References Cited

U.S. PATENT DOCUMENTS

| | | | |
|---|---|---|---|
| 3,836,642 | A | 9/1974 | Keller et al. |
| 4,270,537 | A | 6/1981 | Romaine |

(Continued)

FOREIGN PATENT DOCUMENTS

| | | |
|---|---|---|
| DE | 4121468 | 1/1993 |
| GB | 1184422 | 3/1970 |

(Continued)

OTHER PUBLICATIONS

Chang et al, The Journal of Antibiotics, 1975, 156.*

(Continued)

*Primary Examiner* — Ganapathy Krishnan
(74) *Attorney, Agent, or Firm* — Bryan Cave Leighton Paisner LLP

(57) ABSTRACT

The invention provides compounds, methods, pharmaceutical compositions, and kits for the treatment of proliferative disorders such as cancer. In one aspect, the methods comprise compounds that inhibit the activity of protein kinases, such as cell division cycle (Cdc) kinase. In another aspect, the methods comprise compounds that inhibit Cdc7 and/or Dbf4 activity. In another aspect, the methods comprise compounds that exhibit anti-proliferative properties useful in treating diseases such as cancer. Compounds useful for any of the methods include compounds of the Formula (A) or (B):

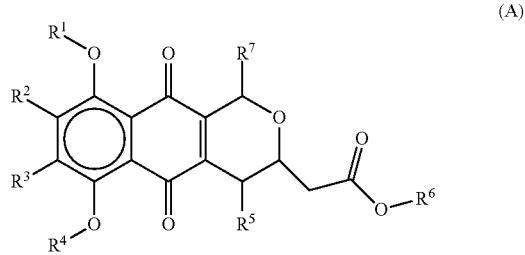

(A)

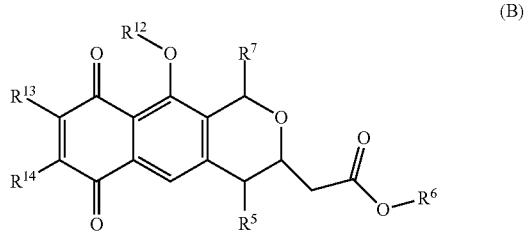

(B)

or pharmaceutically acceptable salts thereof. Exemplary compounds of Formula (A) or (B) include granaticin A, granaticin B, dihydrogranaticin A, dihydrogranaticin B, medermycin, and actinorhodin.

2 Claims, 31 Drawing Sheets

Related U.S. Application Data

(60) Provisional application No. 61/311,741, filed on Mar. 8, 2010.

(56) References Cited

U.S. PATENT DOCUMENTS

| | | |
|---|---|---|
| 4,596,556 A | 6/1986 | Morrow et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hiertman et al. |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,593,970 A | 1/1997 | Attardo et al. |
| 5,599,302 A | 2/1997 | Lillev et al. |
| 5,649,912 A | 7/1997 | Peterson |
| 5,704,911 A | 1/1998 | Parsons |
| 5,893,397 A | 4/1999 | Peterson et al. |
| 5,993,412 A | 11/1999 | Deily et al. |
| 6,610,684 B2* | 8/2003 | Zaharevitz ............ C07D 487/04 514/212.06 |
| 9,180,105 B2* | 11/2015 | Frattini ................ A61K 31/365 |
| 9,492,427 B2* | 11/2016 | Frattini ................ A61K 31/352 |
| 9,782,386 B2* | 10/2017 | Frattini ................ A61K 31/365 |
| 10,123,992 B2* | 11/2018 | Frattini ................ A61K 31/352 |
| 2007/0191330 A1 | 8/2007 | Castillo et al. |
| 2013/0035301 A1 | 2/2013 | Frattini et al. |
| 2017/0119731 A1 | 5/2017 | Frattini et al. |
| 2017/0360746 A1 | 12/2017 | Kunnari |

FOREIGN PATENT DOCUMENTS

| | | |
|---|---|---|
| JP | 2005220037 | 8/2005 |
| WO | 97/13537 | 4/1997 |
| WO | 97/37705 | 10/1997 |
| WO | 99/34850 | 7/1999 |
| WO | 2011/112635 | 9/2011 |

OTHER PUBLICATIONS

Kulanthaivel et al, The Journal of Antibiotics, 1999, 52(3), 256-262.*
Nomura et al, J. Am. Chem. Soc. 1987, 109, 3402-3408.*
Shimbashi et al, Bull. Chem. Soc. Jpn., 2004, 77, 1925-1930.*
Sherr, Cancer cell cycles. Science. Dec. 6, 1996;274(5293):1672-7.
Shimbashi et al., Synthesis of the naphthalene-derived inhibitors against Cdc25A dual-specificity protein phosphatase and their biological activity. Bioorg Med Chem Lett. Jan. 3, 2005;15(1):61-5.
Slebos et al., Gene expression differences associated with human papillomavirus status in head and neck squamous cell carcinoma. Clin Cancer Res. Feb. 1, 2006;12(3 Pt 1):701-9.
Stillman, Cell cycle control of DNA replication. Science. Dec. 6, 1996;274(5293):1659-64.
Sturdik et al., The cytotoxic action of granaticin, a sulfhydryl-reactive antibiotic, on Ehrlich ascites carcinoma cells. Neoplasma. 1983;30(1):3-6.
Tanaka et al., Lactoquinomycin, a novel anticancer antibiotic. I. Taxonomy, isolation and biological activity. J Antibiot (Tokyo). Oct. 1985;38(10):1327-32.
Toral-Barza et al., Discovery of lactoquinomycin and related pyranonaphthoquinones as potent and allosteric inhibitors of AKT/PKB: mechanistic involvement of AKT catalytic activation loop cysteines. Mol Cancer Ther. Nov. 2007;6(11):3028-38. Epub Nov. 7, 2007.
Vashee et al., Assembly of the human origin recognition complex. J Biol Chem. Jul. 13, 2001;276(28):26666-73. Epub Apr. 25, 2001.
Velculescu et al., Analysis of human transcriptomes. Nat Genet. Dec. 1999;23(4):387-8.
Walter, Evidence for sequential action of cdc7 and cdk2 protein kinases during initiation of DNA replication in Xenopus egg extracts. J Biol Chem. Dec. 15, 2000;275(50):39773-8.
Wilen, Tables of Resolving Agents and Optical Resolutions. E.L. Eliel, ed. Universtify of Notre Dame Press, Notre Dame, IN. 1972:268-90.
Wilen et al., Strategies in Optical Resolution. Tetrahedron. 1977;33:2725-36.
Yamashita et al., Functional analyses of mouse ASK, an activation subunit for Cdc7 kinase, using conditional ASK knockout ES cells. Genes Cells. Jun. 2005;10(6):551-63.
Gottesman, Ann. Rev. Med. 2002, 52, 615-27.
Sethi, In Vitro Inhibition of Viral DNA Polymerase Activity by Litmomycin. J Pharm Sci Jan. 1977; 66(1): 130-2.
Nomura et al. J. Am. Chem. Soc. 1987, 109, 3402-08.
Kulanthaivel, et al. Novel naphthoquinones from a *Streptomyces* sp. J Antibiot (Tokyo) Mar. 1999; 52(3): 256-62.
The Merck Manual, 1992, pp. 81-82, 1263, 1266-1269, 1276-1277, 1403-1444, 1488-1489 and 2293-2294.
Change et al. The Journal of Antibodies, Feb. 28, 1975 (2), p. 156.
Sturdik et al. Neoplasma, 1983, 30(1), 3-6.
Hiratake et al. Biomed Pharmacother 1997, 51(6-7), 276-83, abstract.
Tanaka et al., The Journal of Antibiotics, 1985, XXXVIII (10), 1327-32.
Williamson et al. Org. Lett., 2002, 4-4659-62.
Poulsen et al. Amino Acids, 202, 22(4), 333-50, abstract.
International Search Report and Written Opinion for PCT/US2011/027619, dated May 13, 2011.
International Preliminary Report on Patentability for for PCT/US2011/027619, dated Sep. 20, 2012.
Bell et al., DNA replication in eukaryotic cells. Annu Rev Biochem. 2002;71:333-74. Epub Nov. 9, 2001.
Berge et al., Pharmaceutical salts. J Pharm Sci. Jan. 1977;66(1):1-19.
Brown et al., Interaction of the S phase regulator cdc18 with cyclin-dependent kinase in fission yeast. Proc Natl Acad Sci U S A. Jun. 10, 1997;94(12):6142-7.
Chan et al., The role of protein tyrosine kinases and protein tyrosine phosphatases in T cell antigen receptor signal transduction. Annu Rev Immunol. 1994;12:555-92.
Chang et al., Identity of the antitumor antibiotic litmomycin with granaticin A. J Antibiot (Tokyo). Feb. 1975;28(2):156.
Chuang et al., Purification and characterization of the Schizosaccharomyces pombe origin recognition complex: interaction with origin DNA and Cdc18 protein. J Biol Chem. May 10, 2002;277(19):16920-7. Epub Feb. 15, 2002.
Dowell et al., Interaction of Dbf4, the Cdc7 protein kinase regulatory subunit, with yeast replication origins in vivo. Science. Aug. 26, 1994;265(5176):1243-6.
Dutta et al., Initiation of DNA replication in eukaryotic cells. Annu Rev Cell Dev Biol. 1997;13:293-332.
Egerer et al., [The effect of potential antineoplastic antibiotics and the metal complex compound cisplatin on in vitro phagocytosis]. Pharmazie. Dec. 1991;46(12):872-4. German.
Floss et al., Studies on the biosynthesis of antibiotics. J Nat Prod. Nov.-Dec. 1986;49(6):957-70.
Fluge et al., Gene expression in poorly differentiated papillary thyroid carcinomas. Thyroid. Feb. 2006;16(2):161-75.
Gao et al., A dimeric Smac/diablo peptide directly relieves caspase-3 inhibition by XIAP. Dynamic and cooperative regulation of XIAP by Smac/Diablo. J Biol Chem. Oct. 19, 2007;282(42):30718-27. Epub Aug. 27, 2007.

(56) References Cited

OTHER PUBLICATIONS

Gossen et al., A *Drosophila homolog* of the yeast origin recognition complex. Science. Dec. 8, 1995;270(5242):1674-7. Erratum in: Science. Mar. 8, 1996;271(5254):1349.

Hanks et al., Protein kinases 6. The eukaryotic protein kinase superfamily: kinase (catalytic) domain structure and classification. FASEB J. May 1995;9(8):576-96.

Heinstein, Mechanism of action of granaticin: inhibition of ribosomal RNA maturation and cell cycle specificity. J Pharm Sci. Feb. 1982;71(2):197-200.

Hess et al., A human homolog of the yeast CDC7 gene is overexpressed in some tumors and transformed cell lines. Gene. Apr. 28, 1998;211(1):133-40.

Hopwood, Genetic Contributions to Understanding Polyketide Synthases. Chem Rev. Nov. 10, 1997;97(7):2465-2498.

Huiqun et al., Practical procedures for genetic manipulation systems for medermycin-producing *Streptomyces* sp. AM-7161. J Basic Microbiol. Jun. 2010;50(3):299-301.

Ichinose et al., Biosynthetic gene clusters of benzoisochromanequinone antibiotics in *Streptomyces* spp.—identification of genes involved in post-PKS tailoring steps. Actinomycetologica. 1998;12:99-109.

Ichinose et al., Cloning, sequencing and heterologous expression of the medermycin biosynthetic gene cluster of *Streptomyces* sp. AM-7161: towards comparative analysis of the benzoisochromanequinone gene clusters. Microbiology. Jul. 2003;149(Pt 7):1633-45.

Ichinose et al., Functional complementation of pyran ring formation in actinorhodin biosynthesis in *Streptomyces coelicolor* A3(2) by ketoreductase genes for granaticin biosynthesis. J Bacteriol. May 2001;183(10):3247-50.

Iwashita et al., Signal transduction system for growth factor receptors associated with tyrosine kinase activity: epidermal growth factor receptor signalling and its regulation. Cell Signal. Mar. 1992;4(2):123-32.

Jallepalli et al., Cyclin-dependent kinase and initiation at eukaryotic origins: a replication switch? Curr Opin Cell Biol. Jun. 1997;9(3):358-63.

Jares et al., Xenopus cdc7 function is dependent on licensing but not on XORC, XCdc6, or CDK activity and is required for XCdc45 loading. Genes Dev. Jun. 15, 2000;14(12):1528-40.

Johnston et al., First the CDKs, now the DDKs. Trends Cell Biol. Jul. 1999;9(7):249-52.

Kelly et al., Regulation of chromosome replication. Annu Rev Biochem. 2000;69:829-80.

Krone et al., 13C-NMR and CD Spectroscopy with Isochromanquinones—Potent Methods to Determine the Stereochemistry and the Tautomeric Equilibrium in This Group of Antibiotics. Liebigs Annalen der Chemie. 1987;1987(9):751-58.

Leatherwood et al., Interaction of Cdc2 and Cdc18 with a fission yeast ORC2-like protein. Nature. Jan. 25, 1996;379(6563):360-3.

Montagnoli et al., Cdc7 inhibition reveals a p53-dependent replication checkpoint that is defective in cancer cells. Cancer Res. Oct. 1, 2004;64(19):7110-6.

Moon et al., Identification and reconstitution of the origin recognition complex from Schizosaccharomyces pombe. Proc Natl Acad Sci U S A. Oct. 26, 1999;96(22):12367-72.

Nambiar et al., Identification and functional characterization of ASK/Dbf4, a novel cell survival gene in cutaneous melanoma with prognostic relevance. Carcinogenesis. Dec. 2007;28(12):2501-10. Epub Sep. 3, 2007.

Newton, Protein kinase C: structure, function, and regulation. J Biol Chem. Dec. 1, 1995;270(48):28495-8.

Nomoto et al., Mechanism of action of lactoquinomycin a with special reference to the radical formation. J Antibiot (Tokyo). Aug. 1988;41(8):1124-9.

Pines, Cyclins and cyclin-dependent kinases: take your partners. Trends Biochem Sci. Jun. 1993;18(6):195-7.

Rowles et al., Interaction between the origin recognition complex and the replication licensing system in Xenopus. Cell. Oct. 18, 1996;87(2):287-96.

Salaski et al., Pyranonaphthoquinone lactones: a new class of AKT selective kinase inhibitors alkylate a regulatory loop cysteine. J Med Chem. Apr. 23, 2009;52(8):2181-4.

Sclafani, Cdc7p-Dbf4p becomes famous in the cell cycle. J Cell Sci. Jun. 2000;113 ( Pt 12):2111-7.

\* cited by examiner

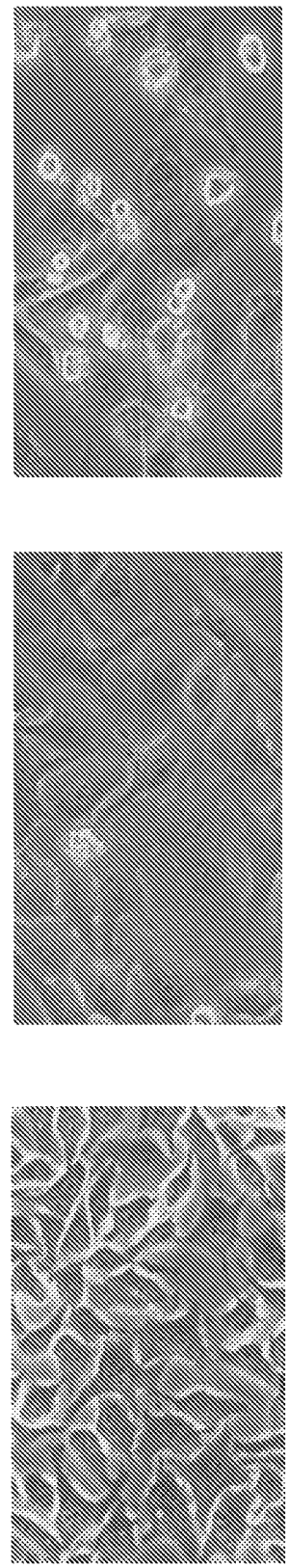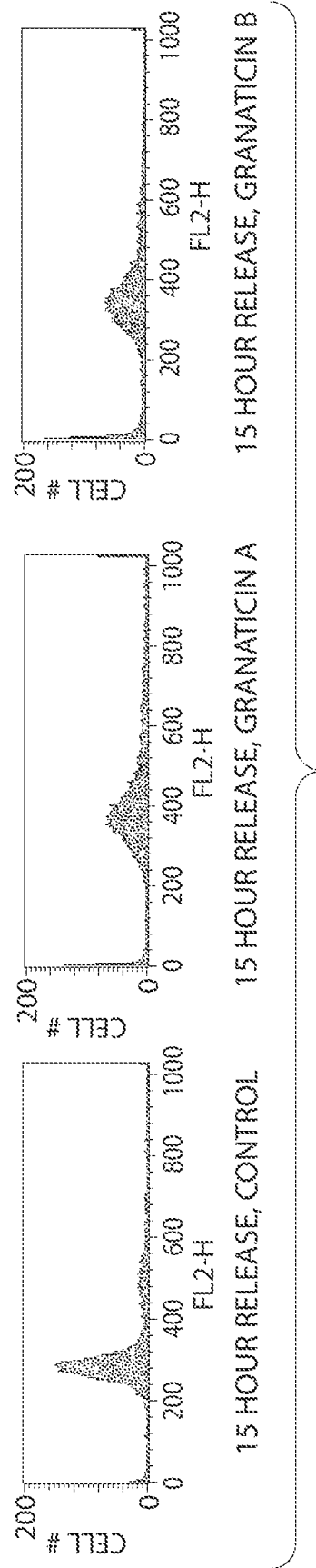
Fig. 11

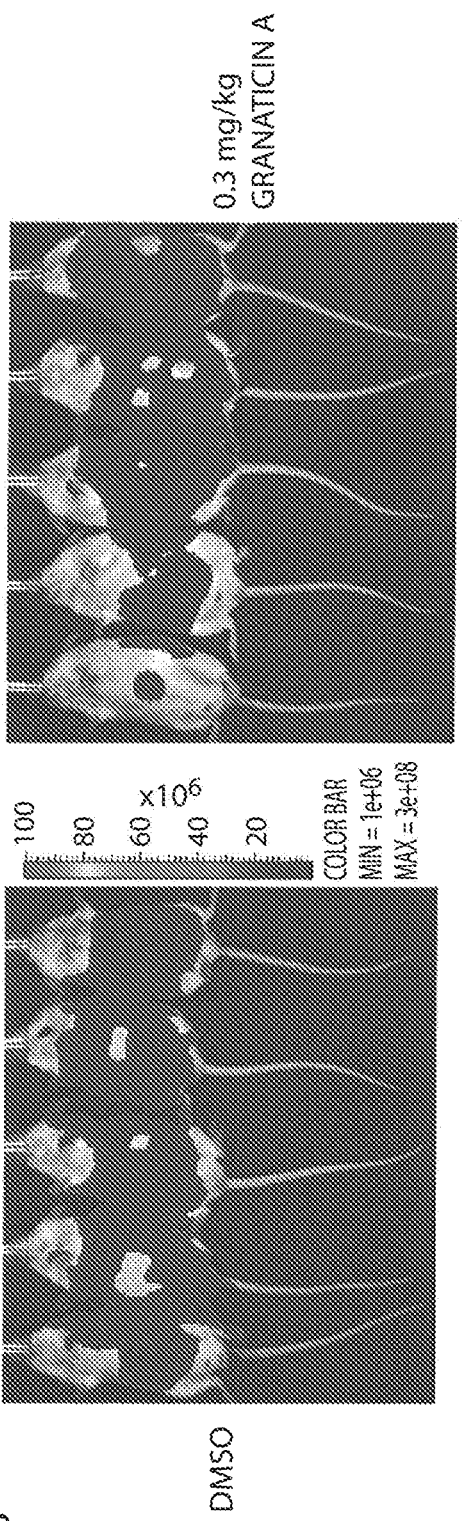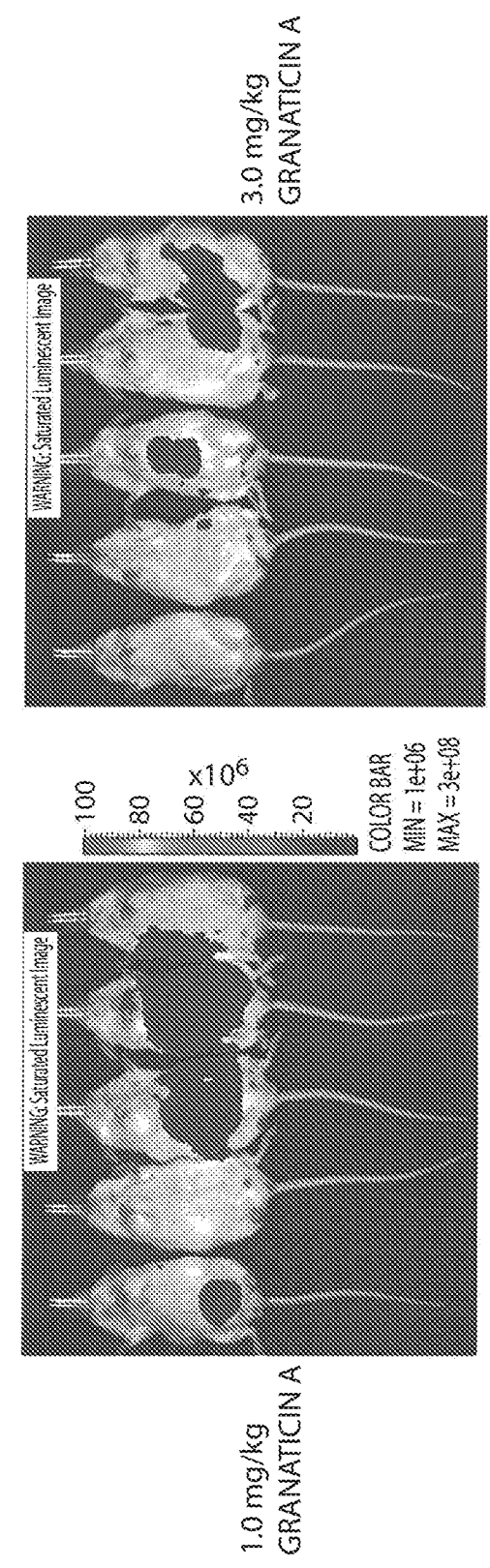
Fig. 19A

GRANATICIN B STABILITY STUDY COMPARISON
IN HUMAN AND MOUSE PLASMA

GRANATICIN B IS EFFECTIVE IN A MELANOMA XENOGRAFT

GRANATICIN B IS EFFECTIVE IN A NON-SMALL CELL LUNG CANCER XENOGRAFT

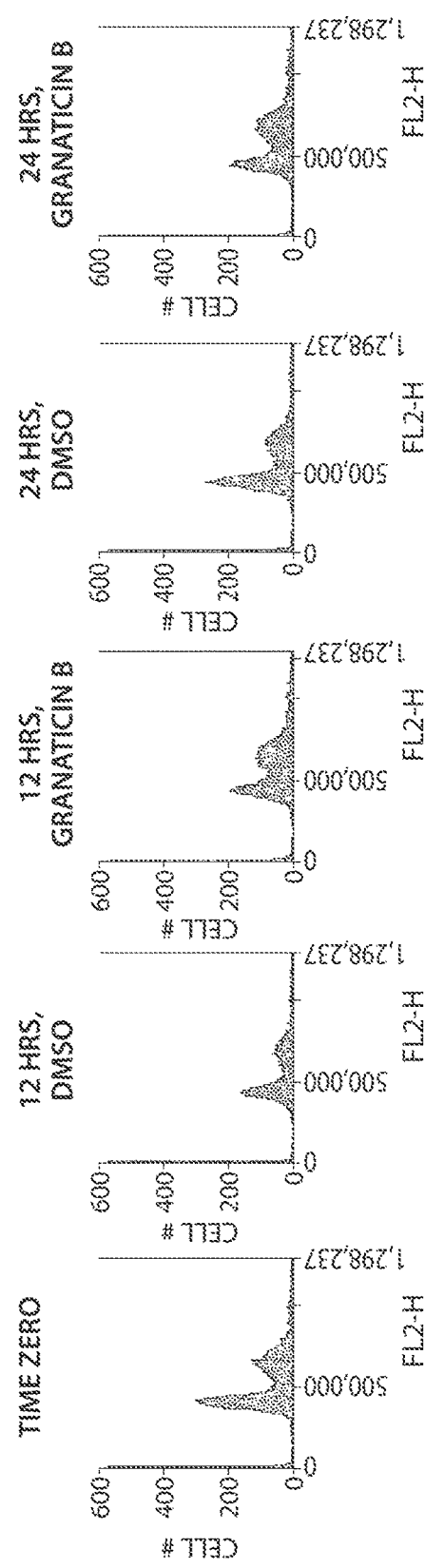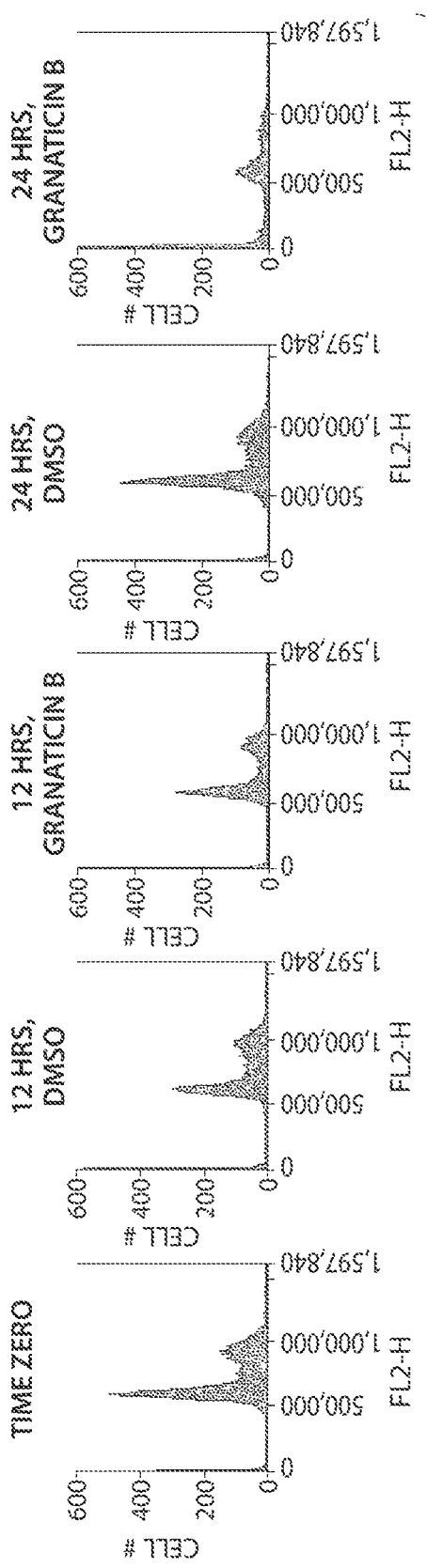
Fig. 23A

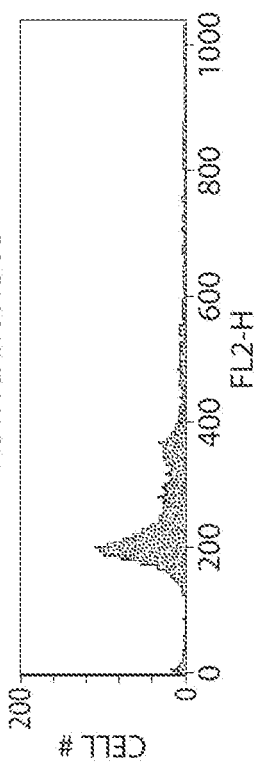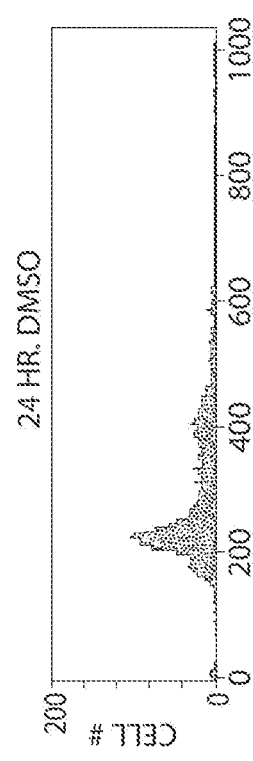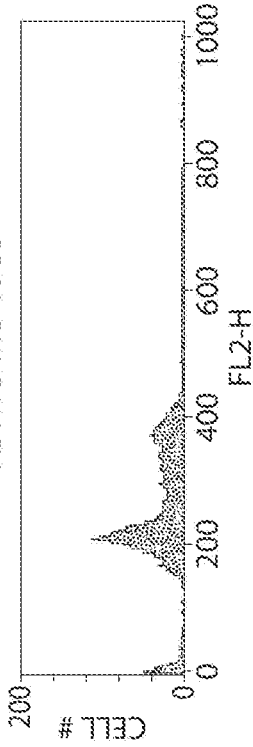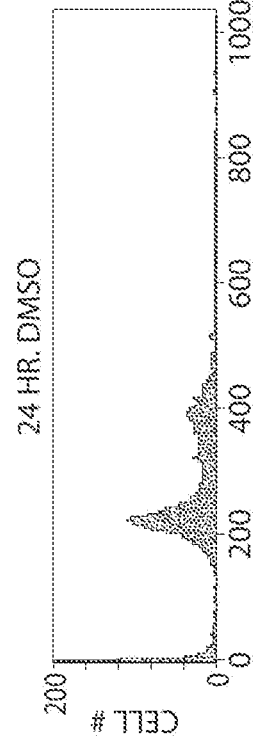
Fig. 23C

CDC7 KINASE INHIBITORS AND USES THEREOF

RELATED APPLICATIONS

The present application is a continuation of and claims priority under 35 U.S.C. § 120 to U.S. application Ser. No. 15/728,609, filed Oct. 10, 2017, now U.S. Pat. No. 10,123, 992, which is a continuation of and claims priority under 35 U.S.C. § 120 to U.S. application Ser. No. 15/349,905, filed Nov. 11, 2016, now U.S. Pat. No. 9,782,386, which is a continuation of and claims priority under 35 U.S.C. § 120 to U.S. application Ser. No. 14/936,472, filed Nov. 9, 2015, now U.S. Pat. No. 9,492,427, which is a continuation of and claims priority under 35 U.S.C. § 120 to U.S. application Ser. No. 13/583,170, filed Oct. 18, 2012, now U.S. Pat. No. 9,180,105, which is a national stage filing under 35 U.S.C. § 371 of international PCT application, PCT/US2011/027619, filed Mar. 8, 2011, which claims priority under 35 U.S.C. § 119(e) to U.S. provisional patent application Ser. No. 61/311,741, filed Mar. 8, 2010, each of which is incorporated herein by reference.

BACKGROUND OF THE INVENTION

Understanding how the genomes of eukaryotes are duplicated during each cell cycle is a fundamental problem of modern biology and is a critical aspect of the more general problem of understanding the mechanisms that control cellular proliferation. The transition from G1 into S phase is a major decision point for the cell and is subject to elaborate controls whose mechanisms are not yet understood at the molecular level. (Bell, S. P. and A. Dutta (2002) *Annu Rev Biochem* 71: 333-74; Dutta, A. and S. P. Bell (1997) *Annu Rev Cell Dev Biol* 13: 293-332; Jallepalli, P. V. and T. J. Kelly (1997) *Curr Opin Cell Biol* 9(3): 358-63; Kelly, T. J. and G. W. Brown (2000) *Annu Rev Biochem* 69: 829-80; Stillman, B. (1996) *Science* 274(5293):1659-64) The stability of the genome depends upon the precise operation of the DNA "replication switch," as well as upon the proper coupling of DNA replication to other events in the cell. It has become quite clear that perturbation of any of these mechanisms can contribute to cancer. (Sherr, C. J. (1996). *Science* 274(5293): 1672-7)

During the last decade, work in a number of laboratories has led to a dramatic advance in our understanding of cellular DNA replication (Bell, S. P. and A. Dutta, et al.; Kelly, T. J. and G. W. Brown, et al.). The analysis of simple model systems, particularly *Saccharomyces cerevisiae, Schizosaccharomyces pombe*, and *Xenopus laevis*, has resulted in the identification of proteins that act at origins of DNA replication to initiate DNA synthesis. A significant breakthrough was the discovery by Stillman and Bell of the six-subunit origin recognition complex (ORC), which binds to specific origins of DNA replication in *S. cerevisiae* and recruits additional initiation factors to form the pre-replication complex (pre-RC). The ORC has been conserved throughout eukaryotic evolution. (Chuang, R. Y., L. Chretien, et al. (2002) *J Biol Chem* 277(19): 16920-7; Gossen, M., D. T. Pak, et al. (1995) *Science* 270(5242): 1674-7; Moon, K. Y., D. Kong, et al. (1999) *Proc Natl Acad Sci USA* 96(22): 12367-12372; Rowles, A., J. P. Chong, et al. (1996) *Cell* 87(2): 287-96; Vashee, S., P. Simancek, et al. (2001) *J Biol Chem* 276(28): 26666-73) We now know that a common set of initiation proteins assemble at replication origins in all eukaryotes and that the activities of these proteins are regulated by specific protein kinases. However, despite this progress, our understanding of the biochemical mechanisms of initiation of eukaryotic DNA replication remains quite superficial.

Genetic studies in yeasts and biochemical studies in *Xenopus* have demonstrated that the initiation of eukaryotic DNA replication takes place in two stages. (Bell, S. P. and A. Dutta, et al.; Kelly, T. J. and G. W. Brown, et al.) In the first stage, which lasts from late M through the G1 phase of the cell cycle, pre-RCs are assembled at origins of DNA replication. At the beginning of S phase, pre-RCs are activated by the action of two heterodimeric protein kinases, Cdc7-Dbf4 and S phase cyclin-dependent kinase (S-CDK). This event marks the transition to the second stage of initiation, during which the origin is unwound and additional proteins are recruited to form active replication forks. The presence of cyclin dependent kinase activity (and perhaps other inhibitory factors) prevents further assembly of pre-RCs during the second stage of the initiation reaction. This mechanism constitutes a "replication switch" that ensures that origins of DNA replication fire only once each cell cycle, thus preserving genomic integrity.

As noted above, the activation of the pre-RC requires the activities of Cdc7-Dbf4 and S-CDK. Both kinases are activated at the G1/S boundary when their respective regulatory subunits accumulate to sufficient levels, and both appear to associate with the pre-RC. (Brown, G. W., P. V. Jallepalli, et al. (1997) *Proc. Natl. Acad. Sci., USA* 94: 6142-6147; Dowell, S. J., P. Romanowski, et al. (1994) *Science* 265 (5176): 1243-6; Jallepalli, P. V. and T. J. Kelly; Jares, P. and J. J. Blow (2000) *Genes Dev* 14(12): 528-40; Johnston, L. H., H. Masai, et al. (1999) *Trends Cell Biol* 9(7): 249-52; Leatherwood, J., A. Lopez-Girona, et al. (1996) *Nature* 379(6563): 360-3; Walter, J. C. (2000) *J. Biol. Chem.* 275(50): 39773-8) Although the regulation of S-CDK activity has been shown to be quite complex with multiple cyclin subunits pairing with multiple Cdk subunits, Cdc7 activity is strictly regulated by the expression of the Dbf4 subunit, which is very tightly cell cycle regulated with peak expression occurring at the G1/S boundary. (Bell, S. P. and A. Dutta, et al.) The activity of Cdc7 has been shown to be required for entry into S phase of the cell cycle. Studies in yeast have shown that cells depleted of this kinase activity progress from G1 to M phase without an intervening S phase, resulting in cell death (Bell, S. P. and A. Dutta, et al.; Kelly, T. J. and G. W. Brown, et al.), and conditional knockout mouse Embryonic stem (ES) cells for Dbf4 have recently been shown to undergo S phase arrest with resultant apoptosis when gene expression is silenced. (Yamashita, N., Kim, J-M, et al. (2005) *Genes to Cells* 10: 551-563) Genetic evidence has shown that the six subunit Minichromosome Maintenance complex (MCM2-7), the presumed helicase activity required for origin unwinding and the initiation of DNA replication (Bell, S. P. and A. Dutta, et al.; Kelly, T. J. and G. W. Brown, et al.), is a target of regulation by the Cdc7-Dbf4 kinase, and the Mcm2 protein is an excellent substrate for the Cdc7:Dbf4 kinase in vitro. (Sclafani, R. A. (2000) *J Cell Sci* 113(Pt 12): 2111-7) The MCM proteins and Cdc7 have been shown to be overexpressed in the majority of cancers including both solid tumors and hematologic malignancies. (Hess, G. F., Drong, R. F., et al. (1998) *Gene* 211 (1):133-40; Velculescu, V. E., Madden, S. L., et al. (1999) *Nature Genetics* 23: 387-88) Importantly, it has recently been shown that overexpression of Cdc7 in cutaneous melanoma samples was associated with poor risk disease and chemotherapy resistance. (Nambiar, S., Mirmohammadsadegh, A., et al. (2007) *Carcinogenesis* 12: 2501-2510) In addition, Cdc7 overexpression has also been shown in aggressive undifferentiated papillary thyroid carcinoma and in aggressive head and neck cancers that are positive for human papillomavirus (Fluge, O., Bruland, O., Akslen, L. A., et al. (2006) *Thyroid* 16 (2): 161-175; Slebos, R. J. C, Yi, Y., Ely, K., et al. (2006) *Clin Cancer Res* 12(3): 701-709). In fact, sensitive assay systems are being developed in Europe and the United States to detect the presence of MCM proteins in the urine of patients with genitourinary malignancies as well as breast cancer patients, and this seems to correlate with a more aggressive malignancy. Cdc7 activity is also conserved from yeast to man making it an attractive candidate for a therapeutic target. The logical interpretation of this data is that Cdc7:Dbf4 is a bonafide therapeutic target.

SUMMARY OF THE INVENTION

The present invention originates from an appreciation for the critical roles of protein kinases, such as Cdc7, and the discovery that a known class of compounds, the benzoisochromanequinones (BIQs), such as the granaticins, inhibit protein kinase activity. The granaticins, in particular, were discovered to inhibit Cdc kinase activity based upon hits identified from high-thoroughput screening (HTS) of over 300,000 compounds for their ability to inhibit a heterodimer of a kinase (Cdc7) and an activator (Dbf4) that phosphorylates serine and threonine residues. It was further discovered that the granaticins may exhibit properties useful in treating proliferative disorders, such as cancer.

The granaticins are members of a class of *Streptomyces* aromatic antibiotics known as benzoisochromanequinones (BIQs; Ichinose et al., *Actinomycetologica* (1998) 12: 99-109), which also includes medermycin (also known as lactoquinomycin A) and actinorhodin. Of particular interest are chemical modifications at C-10 via a C—C bond either by glycosylation (medermcyin and granaticin) or by dimerization (in actinorhodin) (see, e.g., Hopwood, *Chem Rev* (1997) 97: 2465-2497; Floss et al., *J Nat Prod.* (1986) 49:957-70, Toral-Barza et al., *Mol. Cancer Ther.* (2007) 6:3028-3038; and Salaski et al., *J. Med. Chem.* (2009) 23:2181-2184), or by chemical or enzymatic modification of the 8-diol of the 3-methyl-2-oxabicyclo[2.2.2]oct-5-ene-4, 8-diol group of granaticin A (e.g., coupling a carbohydrate or sugar moiety), e.g., to provide compounds such as granaticin B. The benzoisochromanequinones, granaticins, and related natural products are incorporated into the methods of use, pharmaceutical compositions, and kits described herein.

In one aspect, the present invention is directed to compounds of the Formula (A) or (B):

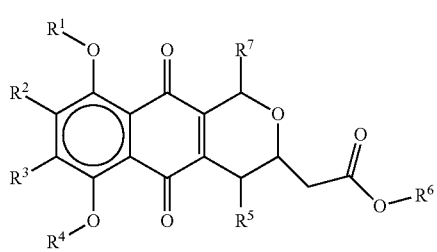

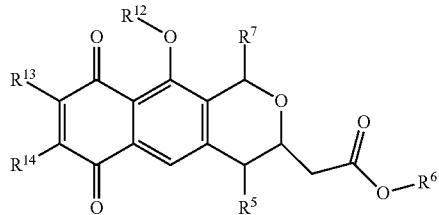

or a pharmaceutically acceptable salt thereof,
wherein:
each instance of $R^1$ and $R^4$ is independently selected from the group consisting of hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of $R^2$ and $R^3$ is independently selected from the group consisting of hydrogen, halogen, —OH, substituted hydroxyl, —SH, substituted thiol, —$NH_2$, substituted amino, —CN, —$NO_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^2$ and $R^3$ are joined to form an optionally substituted carbocyclyl, optionally substituted heterocyclyl, optionally substituted aryl, or optionally substituted heteroaryl group;

$R^5$ is hydrogen and $R^6$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl; or $R^5$ and $R^6$ are joined to form a direct bond;

$R^7$ is hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl;

$R^{12}$ is hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl; and each instance of $R^{13}$ and $R^{14}$ is independently selected from the group consisting of hydrogen, halogen, —OH, substituted hydroxyl, —SH, substituted thiol, —$NH_2$, substituted amino, —CN, —$NO_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^{13}$ and $R^{14}$ are joined to form an optionally substituted carbocyclyl, optionally substituted heterocyclyl, optionally substituted aryl, or optionally substituted heteroaryl group;
for use in treating or preventing a proliferative disorder.

In another aspect, the present invention provides use of a compound of Formula (A) or (B), or a pharmaceutically acceptable salt thereof, for the manufacture of a medicament for treating or preventing a proliferative disorder.

In yet another aspect, the present invention provides a method for treating or preventing a proliferative disorder in a subject in need thereof, wherein the subject is administered a therapeutically effective amount of a compound of the Formula (A) or (B), or a pharmaceutically acceptable salt thereof.

In certain embodiments, the compound is of the Formula (A-3):

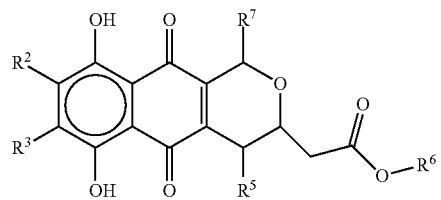
(A-1)

or a pharmaceutically acceptable salt thereof.

In certain embodiments, the compound is of the Formula (A-7):

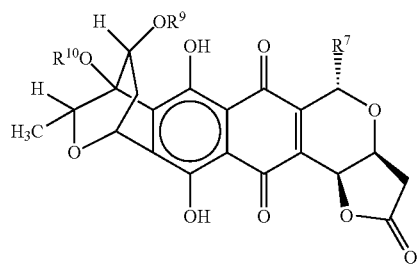
(A-7)

or a pharmaceutically acceptable salt thereof, wherein each instance of $R^9$ and $R^{10}$ is independently selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, sulfonyl, and sulfinyl.

In certain embodiments, the compound is of the Formula (B-1):

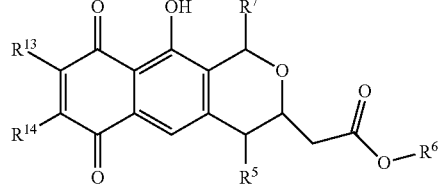
(B-1)

or a pharmaceutically acceptable salt thereof.

In certain embodiments, the compound is selected from the group consisting of:

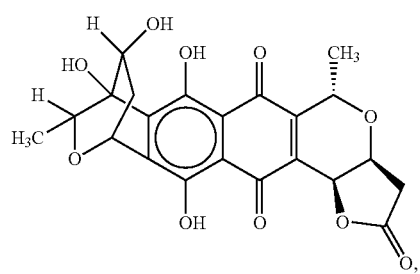
(I)

granaticin A

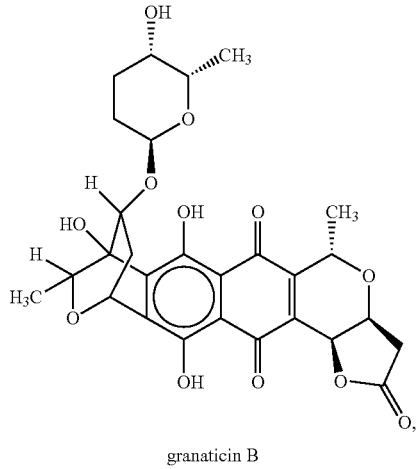
(II)

granaticin B,

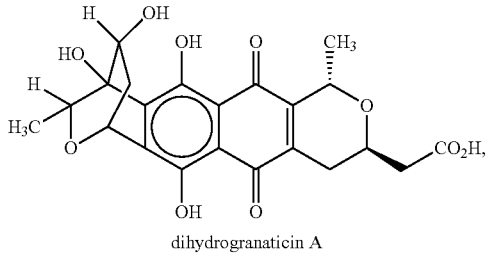
(III)

dihydrogranaticin A

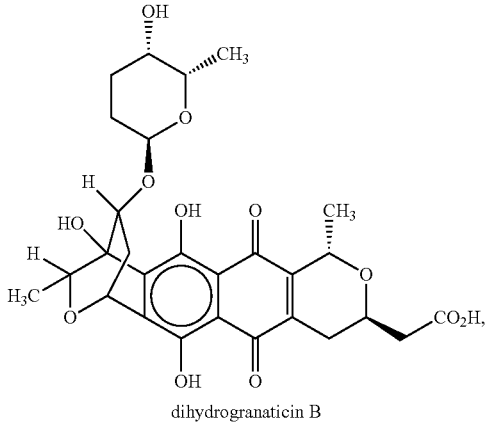
(IV)

dihydrogranaticin B

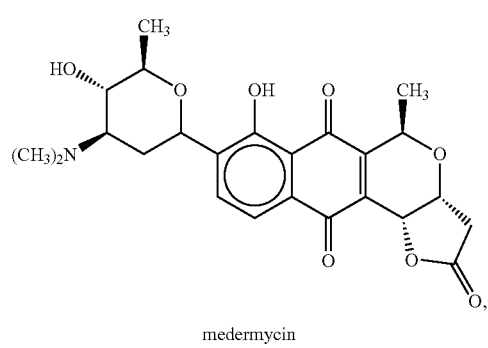
(V)

medermycin

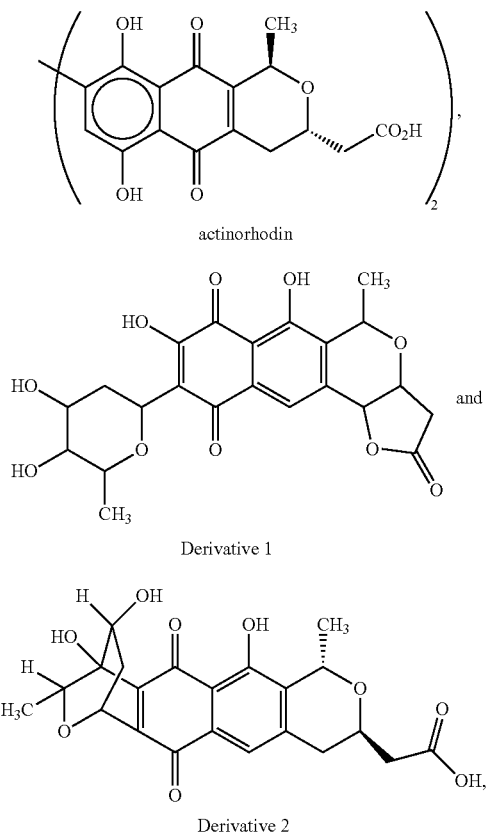

or a pharmaceutically acceptable salt thereof.

In certain embodiments, the compound is an inhibitor of a protein kinase; and wherein the inhibition of a protein kinase is useful for the treatment or prevention of the proliferative disorder. In certain embodiments, the protein kinase is Cdc7 kinase or the Dbf4 regulatory subunit of Cdc7 kinase, and wherein the inhibition of Cdc7 kinase or the Dbf4 regulatory subunit of Cdc7 kinase is useful for the treatment or prevention of the proliferative disorder.

In certain embodiments, the proliferative disorder is selected from the group consisting of cancer, myeloproliferative disorders, benign prostate hyperplasia, familial adenomatosis, polyposis, neuro-fibromatosis, psoriasis, vascular smooth cell proliferation associated with atherosclerosis, fibrotic disorders, pulmonary fibrosis, arthritis, rheumatoid arthritis, glomerulonephritis, and post-surgical stenosis, restenosis, disorders of proliferation of blood vessels, disorders of proliferation of mesangial cells, metabolic disorders, allergies, asthmas, thromboses, diseases of the nervous system, retinopathy, diabetes, and muscular degeneration. In certain embodiments, proliferative disorder is cancer.

In certain embodiments, the cancer is selected from the group consisting of bone, brain, connective tissue, endocrine glands, adrenal cortex, endometrium, germ cells, head and neck, larynx and hypopharynx, mesothelioma, muscle, rectum, renal, small intestine, soft tissue, testis, ureter, vagina, and vulva; bladder cancer; breast cancer; colon cancer; kidney cancer; liver cancer; lung cancer; esophagus cancer; gallbladder cancer; ovarian cancer; pancreatic cancer; stomach cancer; cervical cancer; thyroid cancer; prostate cancer; papillary thyroid carcinoma; genitourinary malignancies; retinoblastoma; Wilms tumor; myelodysplastic syndrome; plasma cell neoplasia; paraneoplastic syndromes; renal cell carcinoma; Ewing's sarcoma; desmoplastic small round cell tumors; mesothelioma; skin cancer, wherein said skin cancer is squamous cell carcinoma; hematologic cancers [e.g., hematopoietic cancers of lymphoid lineage, wherein said cancers are leukemia, acute lymphocytic leukemia (ALL), acute lymphoblastic leukemia, lymphoma, B-cell lymphoma, T-cell lymphoma, Hodgkin's lymphoma, non-Hodgkin's lymphoma (e.g., mantle cell lymphoma (MCL), hairy cell lymphoma, and Burkitt's lymphoma; chronic lymphocytic leukemia (CLL); hematopoietic cancers of myeloid lineage, wherein said cancers are multiple myeloma, chronic myeloid leukemia (CML) and acute myeloid leukemia (AML) (e.g., acute megakaryoblastic leukemia (AMKL); myelodysplastic syndrome and promyelocytic leukemia]; tumors of mesenchymal origin, wherein the tumors are fibrosarcoma and rhabdomyosarcoma; tumors of the central and peripheral nervous system, wherein said tumors are astrocytoma, neuroblastoma, glioma (e.g., glioblastoma) and schwannomas; and other tumors, wherein said tumors are melanoma, cutaneous melanoma, seminoma, teratocarcinoma, osteosarcoma, xeroderma pegmentosum, keratoxanthoma, thyroid follicular cancer, Kaposi's sarcoma, cancers of unknown primary site; solid tumors, hematologic cancers, and AIDS-related malignancies.

In certain embodiments, the cancer is a hematologic cancer, ovarian cancer, lung cancer, prostate cancer, renal cell carcinoma, cervical cancer, glioblastoma, retinoblastoma, rhabdomyosarcoma, desmoplastic small round cell tumor, breast cancer, mesothelioma, melanoma, thyroid carcinoma, Ewing's sarcoma, or a solid tumor.

In certain embodiments, the cancer comprises a genetic mutation. In certain embodiments, the genetic mutation comprises a RAS mutation, an EGFR mutation, a KRAS mutation, a p53 mutation, a BRAF mutation, a EVI1 mutation, a Flt-3 mutation, WT-1 mutation, cyclin D mutation, PTEN mutation, ABL kinase mutation, or a chromosomal abnormality.

In certain embodiments, the cancer is a multi-drug resistant (MDR) cancer.

In certain embodiments, the cancer is relapsed and/or refractory cancer.

In certain embodiments, the method further comprises administering at least one other therapy or therapeutic agent. In certain embodiments, the method further comprises administering radiation.

Also provided are pharmaceutical composition and kits useful in any of the methods.

The details of one or more embodiments of the invention are set forth in the accompanying Figures and the Detailed Description. Other features, objects, and advantages of the invention will be apparent from the description and from the claims.

DEFINITIONS

Compounds useful in the present invention include inhibitors of Cdc7 kinase and/or Dbf4. Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 10 carbon atoms and one or more carbon-carbon double bonds ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-10}$ cycloalkyl. In certain embodiments, the cycloalkyl group is a substituted $C_{3-10}$ cycloalkyl.

As used herein, "heterocyclyl" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, a "direct bond" refers to the direct attachment of a group via a single bond.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, NR$^{bb}$C(=NR$^{bb}$)N(R$^{bb}$)$_2$, —C(=O)NR$^{bb}$SO$_2$R$^{aa}$, NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-14}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(RC)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two RC groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, NR$^{ff}$CO$_2$R$^{ee}$, NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3{}^+$X$^-$, —NH(C$_{1-6}$ alkyl)$_2{}^+$X$^-$, —NH$_2$(C$_{1-6}$ alkyl)$^+$X$^-$, —NH$_3{}^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S;

wherein X$^-$ is a counterion.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino or a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, NR$^{bb}$ C(=O)R$^{aa}$, —NR$^{bb}$CO$_2$R$^{aa}$, —NR$^{bb}$C(=O)N(R$^{bb}$)$_2$, NR$^{bb}$C(=NR$^{bb}$)N(R$^{bb}$)$_2$, NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3{}^+$X$^-$, wherein R$^{bb}$ and X$^-$ are as defined herein.

As used herein, the term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

As used herein, the term "sulfinyl" refers to the group —S(=O)R$^{aa}$, wherein R$^{aa}$ is as defined herein.

As used herein, the term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$), —C(=NR$^{bb}$)N(R$^{bb}$)$_2$), wherein R$^{aa}$ and R$^{bb}$ are as defined herein.

As used herein, the term "silyl" refers to the group —Si(R$^{aa}$)$_3$, wherein R$^{aa}$ is as defined herein.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HSO$_4{}^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two RC groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an amino protecting group. Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Amino protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, the Examples and in the claims. The invention is not intended to be limited in any manner by the above exemplary listing of substituents.

The compounds useful in the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a particular enantiomer. In other embodiments the compound is made up of at least about 95%, 98%, or 99% by weight of a particular enantiomer. A desired enantiomer may be isolated from a racemic mixture by any method known to those skilled in the art, including chiral high pressure liquid chromatography (HPLC) or the formation and crystallization of chiral salts, or the enantiomer may be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

As used herein, the term "tautomer" includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds useful in this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Other pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds useful in the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds useful in the invention. The term "prodrug" refers to compounds that are rapidly transformed in vivo to yield the parent compound of the above formula, for example by hydrolysis in blood. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester or an ether which is cleaved in vivo to yield a compound of interest. Pro-drugs of a variety of compounds, and materials and methods for derivatizing the parent compounds to create the pro-drugs, are known and may be adapted to the present invention. The biological activity of pro-drugs and pro-drugs may also be altered by appending a functionality onto the compound, which may be catalyzed by an enzyme. Also, included are oxidation and reduction reactions, including enzyme-catalyzed oxidation and reduction reactions. A thorough discussion of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As used herein the term "inhibit" means to reduce the amount of kinase activity to a level or amount that is statistically significantly less than an initial level, which may be a baseline level of kinase activity.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

As used herein, unless otherwise specified, the terms "prevent," "preventing" and "prevention" contemplate an action that occurs before a subject begins to suffer from the specified disease or disorder, which inhibits or reduces the severity of the disease or disorder.

The terms "administer," "administering," or "administration," as used herein refers to implanting, absorbing, ingesting, injecting, or inhaling the compound.

The term "subject" refers to any animal. The subject may be at any stage of development. A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys. In some embodiments, the subject is a rodent. In certain embodiments, the subject is an experimental animal such as a mouse, rat, dog, or non-human primate. In certain embodiments, the subject is a transgenic animal.

The term "proliferative disorder" as used herein refers to any disease associated with an undesired and/or abnormal proliferation of cells. The cells may be any type of cell found in the subject. The proliferation may be due to any cause (e.g., any genetic mutation, any signal).

A therapeutically effective amount of a compound comprises administering an amount necessary to achieve a desired result. The exact amount required will vary from subject to subject, depending on the species, age, general condition of the subject, the severity of the disease, the particular anticancer agent, its mode of administration, the desired outcome, and the like. In certain embodiments of the present invention, a "therapeutically effective amount" of a compound or pharmaceutical composition is that amount effective for inhibiting cell proliferation in a subject or a biological sample (e.g., in cells). In certain embodiments, cell proliferation is inhibited by about 10%, about 20%, about 30%, about 40%, about 50%, about 60%, about 70%, about 80%, about 90%, about 95%, or about 99%. In certain embodiments, the compound inhibits cell proliferation by at least about 25%, at least about 50%, at least about 75%, or at least about 90%. In certain embodiments of the present invention, a "therapeutically effective amount" refers to an amount of a compound or composition sufficient to inhibit cell proliferation, or refers to an amount of a compound or composition sufficient to reduce the tumor burden in a subject. In certain embodiments, the tumor burden is reduced by about 1%, about 5%, about 10%, about 20%, about 30%, about 40%, about 50%, about 60%, about 70%, about 80%, about 90%, about 95%, or about 99%. In certain embodiments, the tumor burden is reduced by at least about 25%, at least about 50%, at least about 75%, or at least about 90%. In certain embodiments of the present invention a "therapeutically effective amount" of the compound or pharmaceutical composition is that amount effective for reducing or inhibiting the growth of tumor cells and/or killing tumor cells.

As used herein, a "prophylactically effective amount" of a compound is an amount sufficient to prevent a disease or disorder, or one or more symptoms associated with the disease or disorder, or prevent its recurrence. A prophylactically effective amount of a compound means an amount of therapeutic agent, alone or in combination with other agents, which provides a prophylactic benefit in the prevention of the disease or disorder. The term "prophylactically effective amount" can encompass an amount that improves overall prophylaxis or enhances the prophylactic efficacy of another prophylactic agent.

BRIEF DESCRIPTION OF THE DRAWINGS

FIG. 11. Cell cycle arrest in Hela S3 cells: Morphologic appearance of control (DMSO), granaticin A, and granaticin B treated HeLa S3 cells following 15 hours release from double thymidine block. While control cells look normal and healthy, granaticin A treated cells appear arrested with flattened morphology and peri-nuclear vacuolization consistent with induction of apoptosis. This phenotype is more pronounced in the granaticin B treated cells as one now sees nuclear blebbing and cell death. The corresponding FACS profiles are shown.

FIG. 12: HeLa cells alone; FIG. 13: Bcl-XL overexpressing HeLa cells; and FIG. 14: Bcl-XL overexpressing HeLa cells in the presence of 10 micromolar Ac-DEVD-CHO (a caspase-3 peptide aldehyde inhibitor) demonstrating activation of caspase-3 and apoptosis in granaticin A treated HeLa cells that is rescued by both overexpression of Bcl-XL and chemical inhibition of caspase-3 activity.

FIGS. 16A and 16B summarize the IC50 determinations for granaticin A and granaticin B, as well as Derivatives 1 and 2 (FIG. 16A) against multiple non-small cell lung cancer cell lines, ovarian cancer cell lines, mesothelioma, sarcoma, and melanoma cell lines including cells isolated from primary patient ocular melanoma samples (124859-A and -SB). These include ras and EGFR gatekeeper mutation containing cell lines in addition to p53 mutant cell lines and other known chemotherapy resistant cell lines. Specifically, this included multi-drug resistance phenotype (MDR-overexpressing) cell lines from multiple hematologic and solid tumor cell lines. Table 2 provided herein summarizes the data provided in FIG. 16B (see Examples). Table 1 highlights a series of primary patient leukemia samples-both acute and chronic and treatment naïve and refractory tested against granaticins A and B and Derivatives 1 and 2 (see Examples). FIGS. 16A and 16B, and Tables 1-2, together, show that granaticin A, Derivatives 1 and 2, and especially granaticin B, are pan-active against multiple tumor cell lines and in primary patient samples from patients with chronic and acute leukemias both treatment naïve and chemotherapy refractory.

FIG. 18A shows that this mouse model of human acute lymphoblastic leukemia faithfully duplicates the progression seen in human disease. FIG. 18B shows that when left untreated these mice meet criteria for euthanasia by day 41 indicating a rapid, progressive, and lethal leukemia.

FIGS. 19A-19B. Granaticin A Inhibits growth of PhALL3.1 in vivo: Using a SCID-Beige mouse intraperitoneal tumor model of PhALL3.1, mice were intraperitoneally treated with vehicle control (DMSO) or the indicated doses of granaticin A on days 3, 6, 9, and 12. Day 16 in vivo bioluminescence imaging (FIG. 19A) and quantitation of tumor volume are shown (FIG. 19B) and indicate 90% reduction in tumor volume by Day 16 in mice treated at the highest dose (3.0 mg/kg). Separate necropsy data revealed no significant (grade 2 or higher) organ toxicity in all mice examined at each dose level.

FIG. 23A-23C. Granaticin A and B are not cytotoxic to normal diploid cells: FIGS. 23A-23B: Granaticin B exposure is not cytotoxic to normal diploid cells. Either HeLa or RPE (retinal pigment epithelial cells, a normal human diploid cell line) cells were incubated in carrier control (DMSO) or granaticin B (1 microM) for 24 hours and samples were subjected to standard FACS analysis with the x-axis indicating DNA content (FIG. 23A). The cell cycle profile for the RPE cells is essentially unaffected by granaticin B exposure where the HeLa cell cycle profile indicates apoptotic cell death with an increase in sub-G1 DNA containing cells and loss of normal cell cycle progression. Extracts from cells at the indicated times, exposed to either DMSO or granaticin B (1 microM), were used in standard caspase-3 activity assays to monitor for induction of apoptosis and show that capsae-3 is only activated in HeLa cells exposed to granaticin B (FIG. 23B). Granaticin B exposure does not result in caspase-3 activation in RPE cells. FIG. 23C: Granaticin A exposure is not cytotoxic to normal diploid cells. Either HeLa or RPE (retinal pigment epithelial cells, a normal diploid cell line) cells were incubated in carrier control (DMSO) or granaticin A for 24 hours and samples were subjected to standard FACS analysis with FL2 indicating DNA content. The cell cycle profile for the RPE cells is unaffected by granaticin A exposure where the HeLa cell cycle profile indicates apoptotic cell death with an increase in sub-G1 DNA containing cells.

FIG. 24A: Joke-2 cells were grown in the presence of DMSO control or granaticin B (1 microM) for the indicated times and viability was measured after staining a cell sample in trypan blue (Sigma-Aldrich). FIG. 24B: Extracts from cells at the indicated times, exposed to either DMSO or granaticin B (1 microM), were used in standard caspase-3 activity assays to monitor for induction of apoptosis and show that capsae-3 is only activated in cells exposed to granaticin B.

DETAILED DESCRIPTION OF CERTAIN EMBODIMENTS OF THE INVENTION

Figure 1:
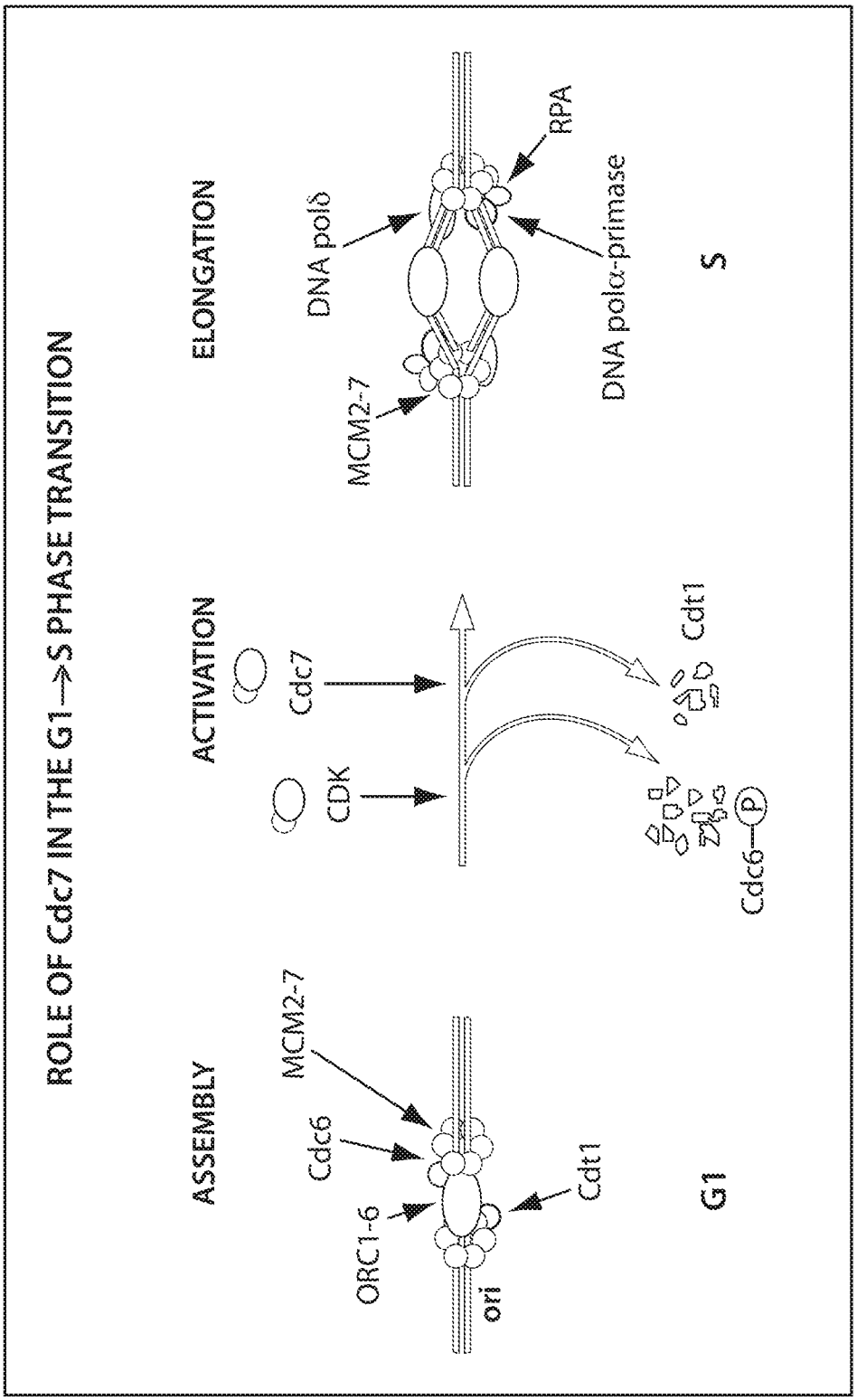
FIG. 1. Role of Cdc7 in the G1→S Phase Transition: Schematic diagram of the initiation of DNA replication in mammalian cells. The process can be divided into several distinct phases: assembly, activation, and elongation. During assembly, the origin of DNA replication (ori) is bound by ORC1-6, the origin recognition complex that serves as a platform for pre-replication complex (pre-RC) assembly during the G1 phase of the cell cycle. This includes binding of the accessory proteins Cdc6, Cdt1, and the MCM2-7 protein complex that serves as the replicative helicase. At the G1/S phase transition, the pre-RCs are activated by both cyclin dependent kinase (CDK) and Cdc7 kinase resulting in the establishment of the replication fork. Fork establishment includes recruitment of single strand DNA binding protein (RPA) and the DNA polymerases required for leading and lagging strand synthesis. Regulation of Cdc6 and Cdt1 via phosphorylation and protein complex assembly with geminin, respectively, inhibits further assembly of functional pre-RCs insuring genomic integrity.
Figure 2:
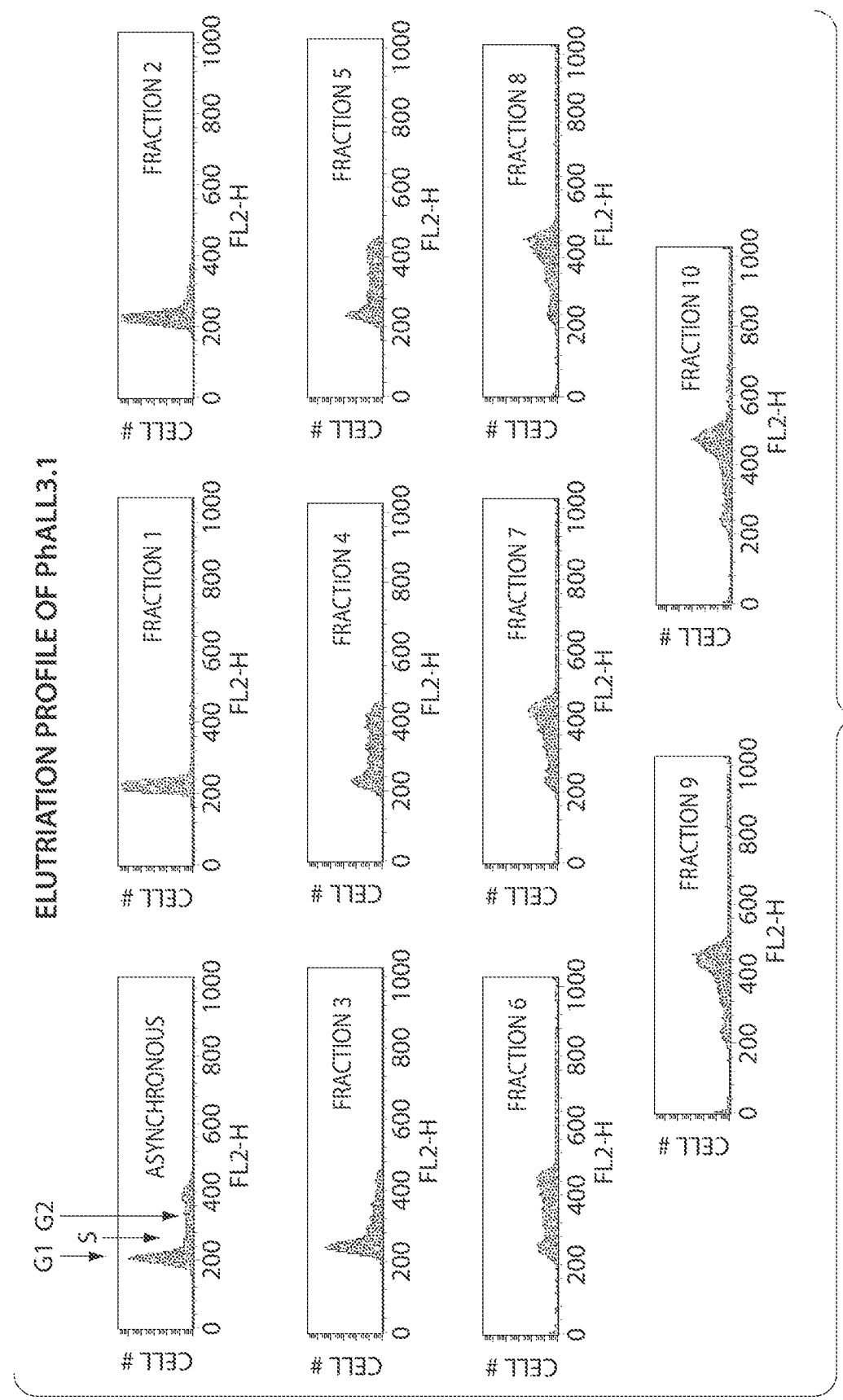
FIG. 2. Elutriation profile of PhALL3.1: Centrifugal elutriation was used to synchronize the recently established Philadelphia chromosome positive acute lymphoblastic leukemia cell line (PhALL3.1). An asynchronous culture (4 liters) was pelleted, resuspended in a small volume (20 ml), and loaded into the elutriation rotor as outlined by the manufacturer (Beckman). After equilibration and washing, cell samples were eluted from the rotor based on size with the smaller cells exiting the rotor first. Ten fractions (250 ml) were taken across the gradient and standard FACS analysis performed on 10 ml of each fraction looking at DNA content. G1, S, and G2 phase cell populations are indicated in the asynchronous profile. This method allows for isolation of phase specific cell populations.
Figure 3:
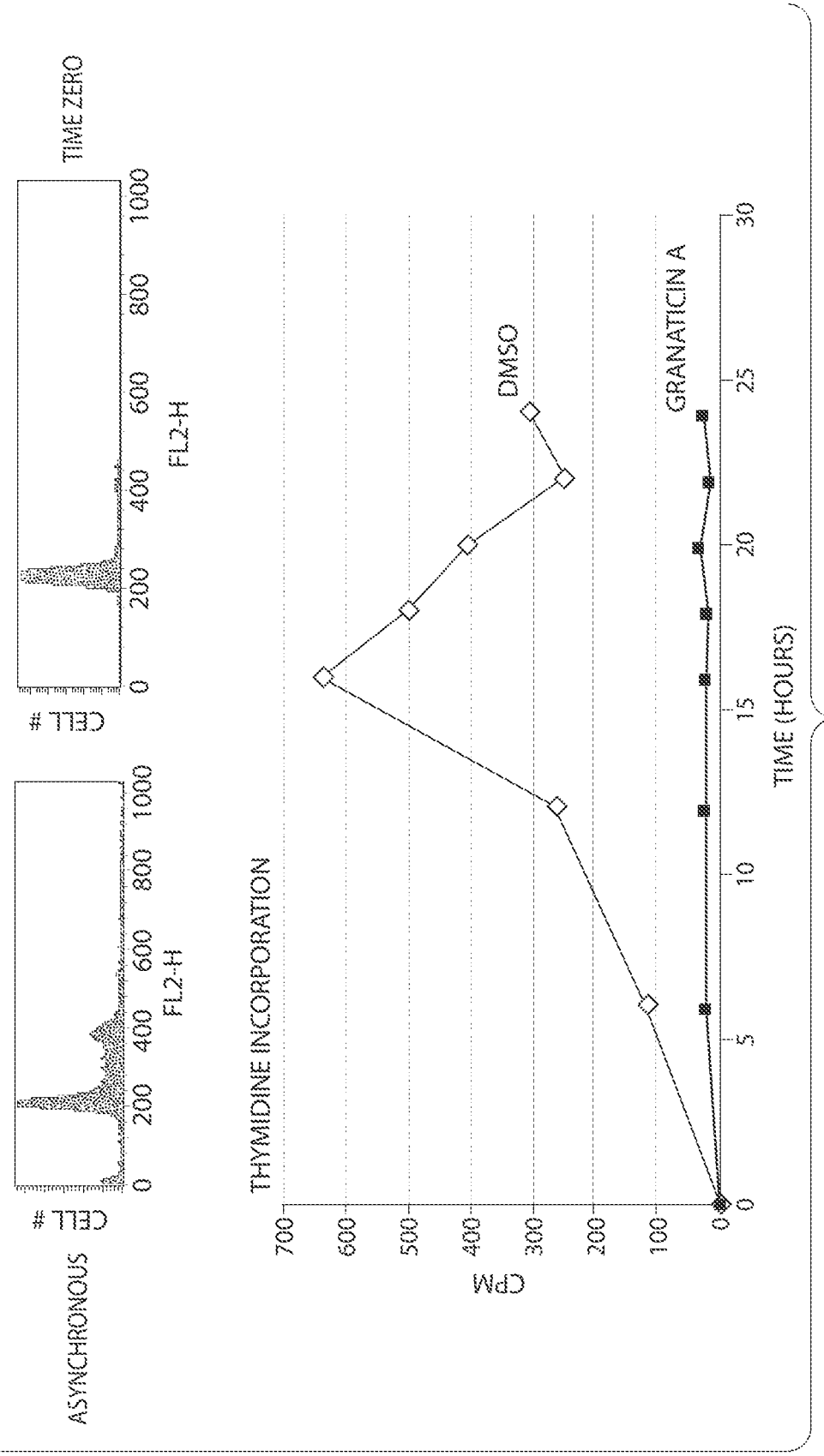
FIG. 3. Granaticin A Inhibits G1→S Transition: Granaticin A induces cell cycle arrest in G1 phase cells. Ph-ALL3.1 cells were subjected to standard centrifugal elutriation conditions and the G1 phase fraction, as determined by FACS analysis (Time Zero), was released into granaticin A (1 mM) or vehicle control (DMSO) for the indicated times. Cell samples post-release into granaticin A or vehicle control (DMSO) were pulsed for 2 hours with $^3$H-thymidine and samples were collected, washed, and acid precipitable counts were measured by scintillation counting. X-axis is time post-release into compound or control (in hours) and y-axis is counts per minute (CPM). The graph demonstrates that while the control cells progress through a normal S phase with a peak in incorporation as expected from the cell cycle profile observed, granaticin A treated samples stop incorporating $^3$H-thymidine with cell cycle profiles showing G1 phase arrest. This implies that there is a complete block to enter S phase (and activate origin firing) in the G1 population, corresponding to inhibition of Cdc7 kinase activity.
Figure 4:
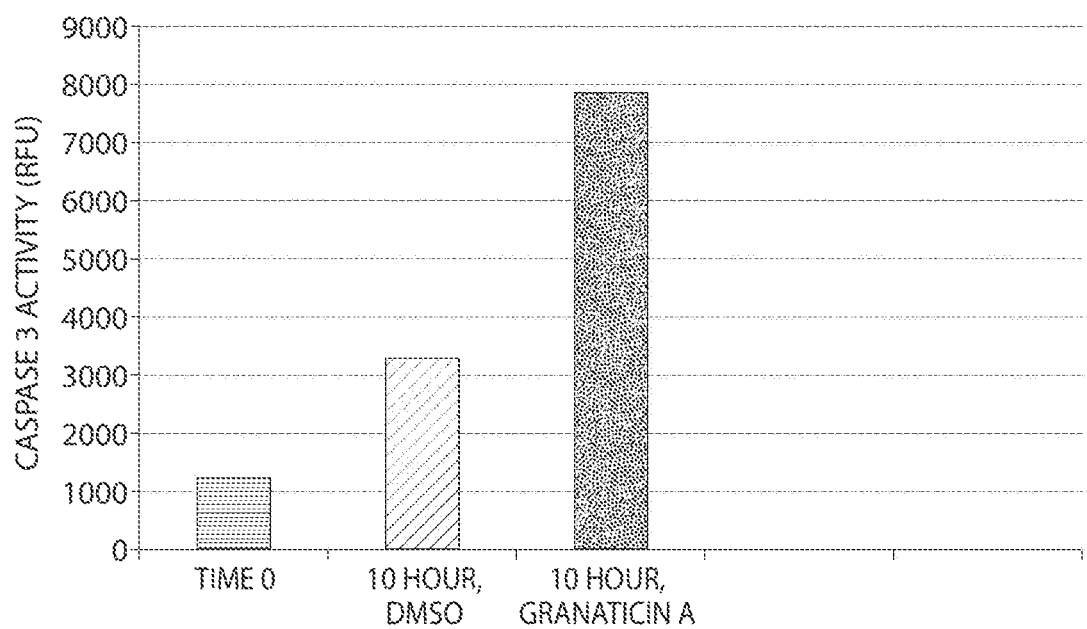
FIG. 4. Granaticin A induces Caspase 3-mediated apoptosis: 10 hours following release of G1 synchronized PhALL3.1 cells into either control (DMSO) or granaticin A, cell samples were taken and caspase 3 activity was measured using a standard fluorometric assay as described in Gao et al., "Dimeric Smac/Diablo Peptide Directly Relieves Caspase-3 Inhibition by XIAP" *Journal Biological Chemistry* (2007) 282:30718-30727.
Figure 5:
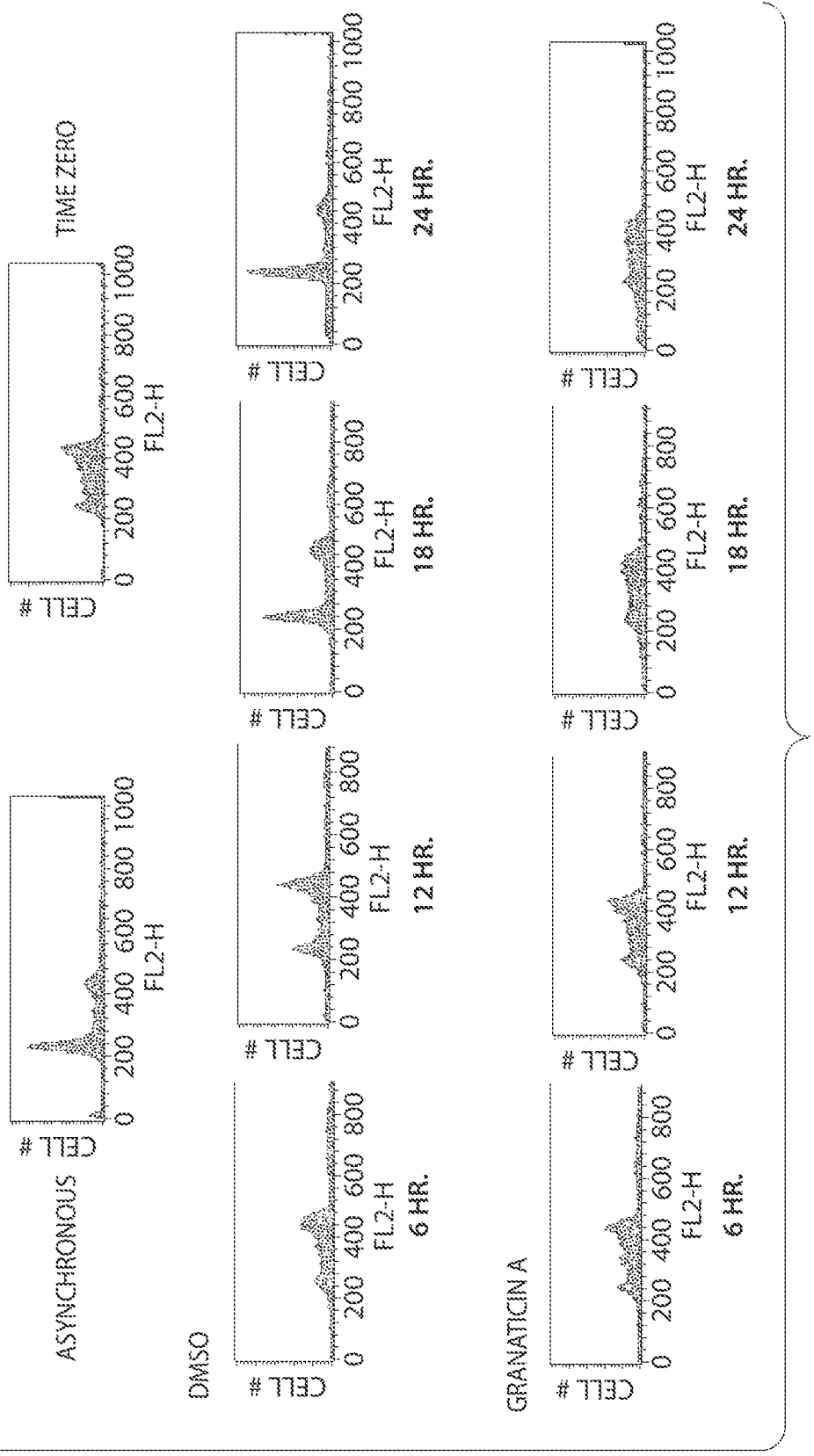
FIG. 5. Granaticin A Induces Arrest and Apoptosis in S Phase cells: Granaticin A induces cell cycle arrest and apoptosis in S phase cells. Ph-ALL3.1 cells were subjected to standard centrifugal elutriation conditions and the S phase fraction, as determined by FACS analysis, was released into granaticin A (1 μM) or vehicle control (DMSO) for the indicated times and FACS analysis was performed. Displayed are FACS profiles with DNA content on the x-axis and cell number on the y-axis demonstrating cell cycle progression in the control samples and arrest in the granaticin A treated samples with subsequent apoptosis as the sub-G1 fraction increases with time. Apoptosis was confirmed in additional independent experiments. Asynchronous and time zero correspond to an asynchronous cell sample and the elutriated S phase fraction prior to release, respectively.
Figure 6:
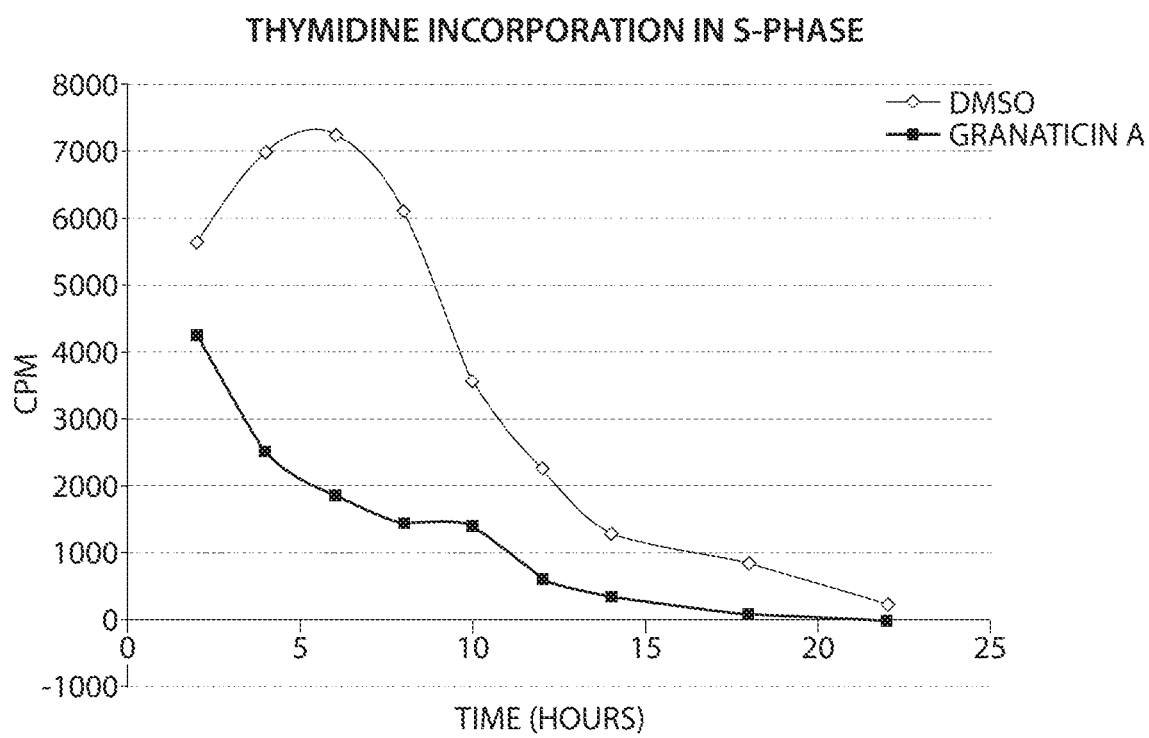
FIG. 6. Thymidine incorporation in S-phase. $^3$H-Thymidine incorporation during the release experiment outlined in the slide above. Cell samples post-release into granaticin A or vehicle control (DMSO) were pulsed for 2 hours with $^3$H-thymidine, and samples were collected, washed, and acid precipitable counts were measured by scintillation counting. X-axis is time post-release into compound or control (in hours) and y-axis is counts per minute (CPM). The graph demonstrates that while the control cells progress through a normal S phase with a peak in incorporation as expected from the cell cycle profile observed, granaticin A treated samples display markedly reduced incorporation early and eventually stop incorporating $^3$H-thymidine with cell cycle profiles showing S phase arrest. This implies that not only is late origin firing inhibited, but that replication fork progression is also inhibited by granaticin A.
Figure 7:
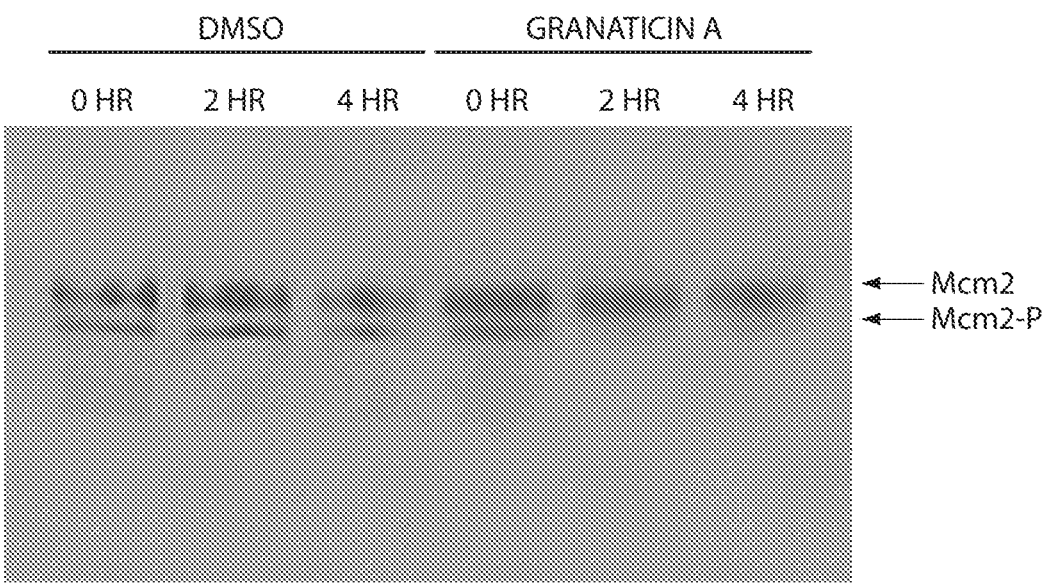
FIG. 7. Granaticin A Inhibits Mcm2 phosphorylation: Following synchronization in S phase and release, PhALL3.1 cells from the experiments of FIG. 5 and FIG. 6 were collected at the indicated times post release into either control (DMSO) or granaticin A and extracts were subjected to Western blotting to detect total Mcm2 protein. This blot shows inhibition of Mcm2 phosphorylation as early as 2 hours post release into granaticin A and confirms target inhibition by granaticin A within the cell.
Figure 8:
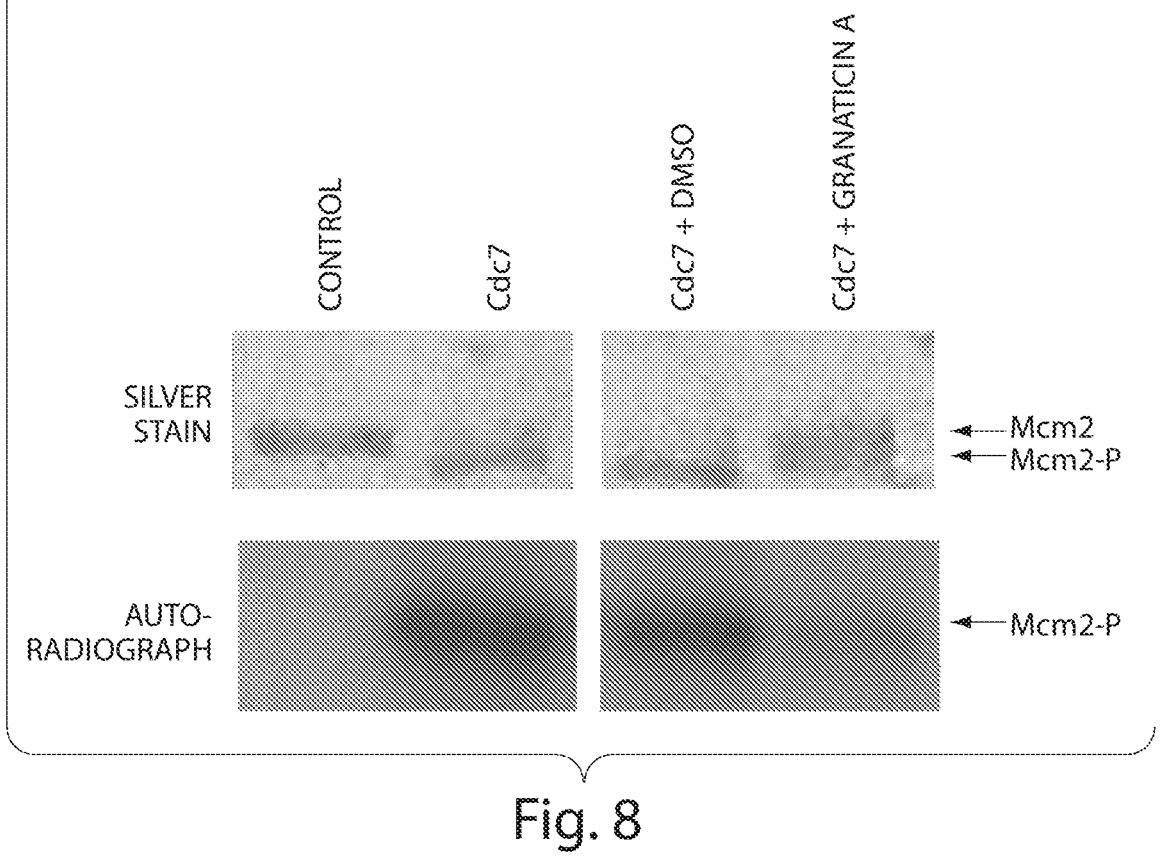
FIG. 8. Mcm2 phosphorylation by Cdc7: Phosphorylated forms of Mcm2 migrate faster in SDS-PAGE gels. Using highly purified human recombinant Cdc7 and Mcm2, standard in vitro kinase reactions were performed in the presence of radioactive ATP and products were separated on SDS-PAGE gels, stained with silver, and autoradiography was performed to detect phosphorylated forms of Mcm2. Control is a negative control for kinase activity, DMSO is a positive control for kinase activity, granaticin A is a small molecule inhibitor of Cdc7 kinase activity.
Figure 9:
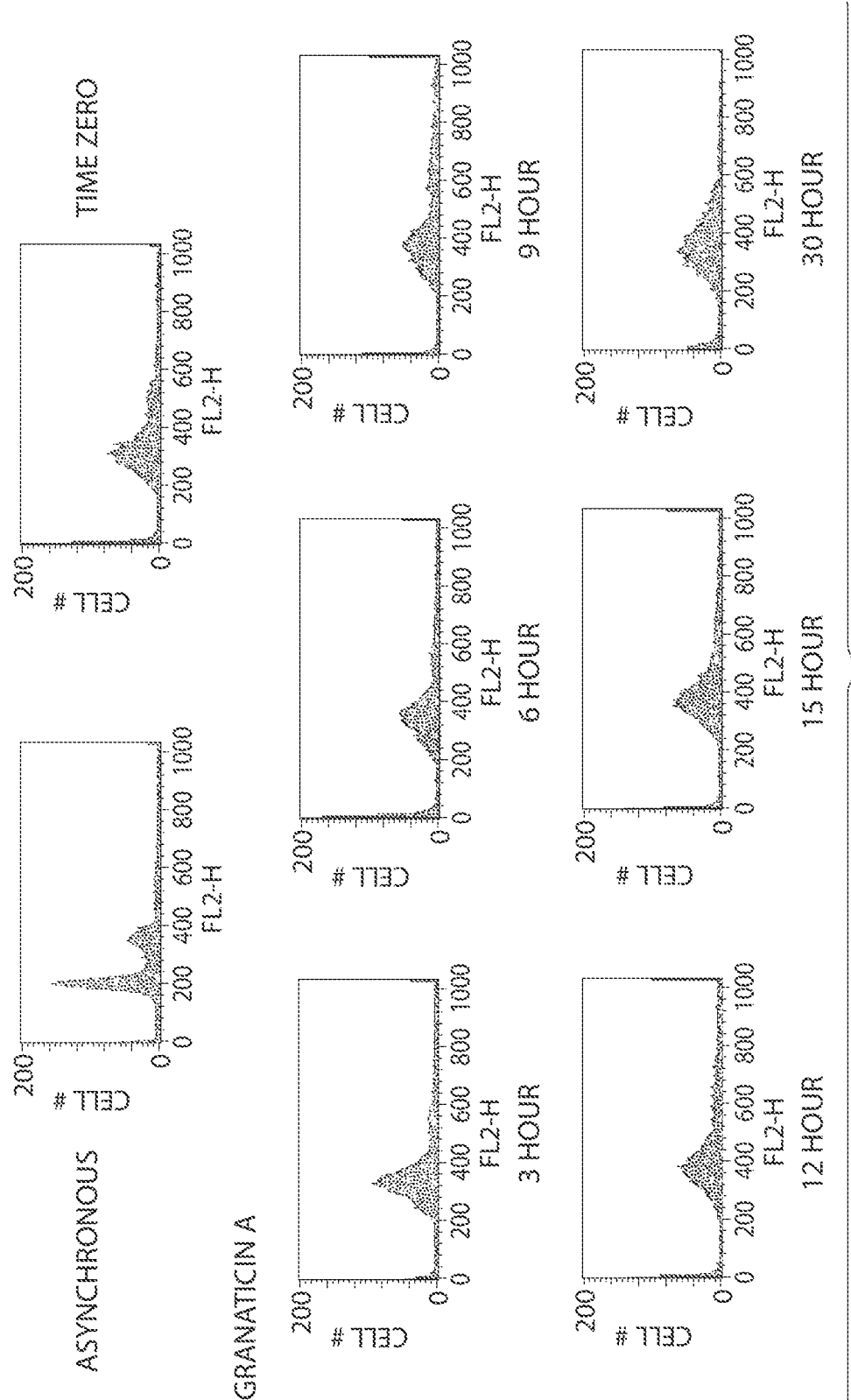
FIG. 9. Granaticin A Induces Cell Cycle Arrest in Hela S3 Cells: HeLa S3 cells (cervical carcinoma) were synchronized at the G1/S transition using standard double thymidine block and release. Synchronized cells (time zero) were released into media containing granaticin A for the indicated times and standard FACS analysis performed looking at DNA content. This study shows that in HeLa cells S phase progression is also blocked by exposure to granaticin A.
Figure 10:
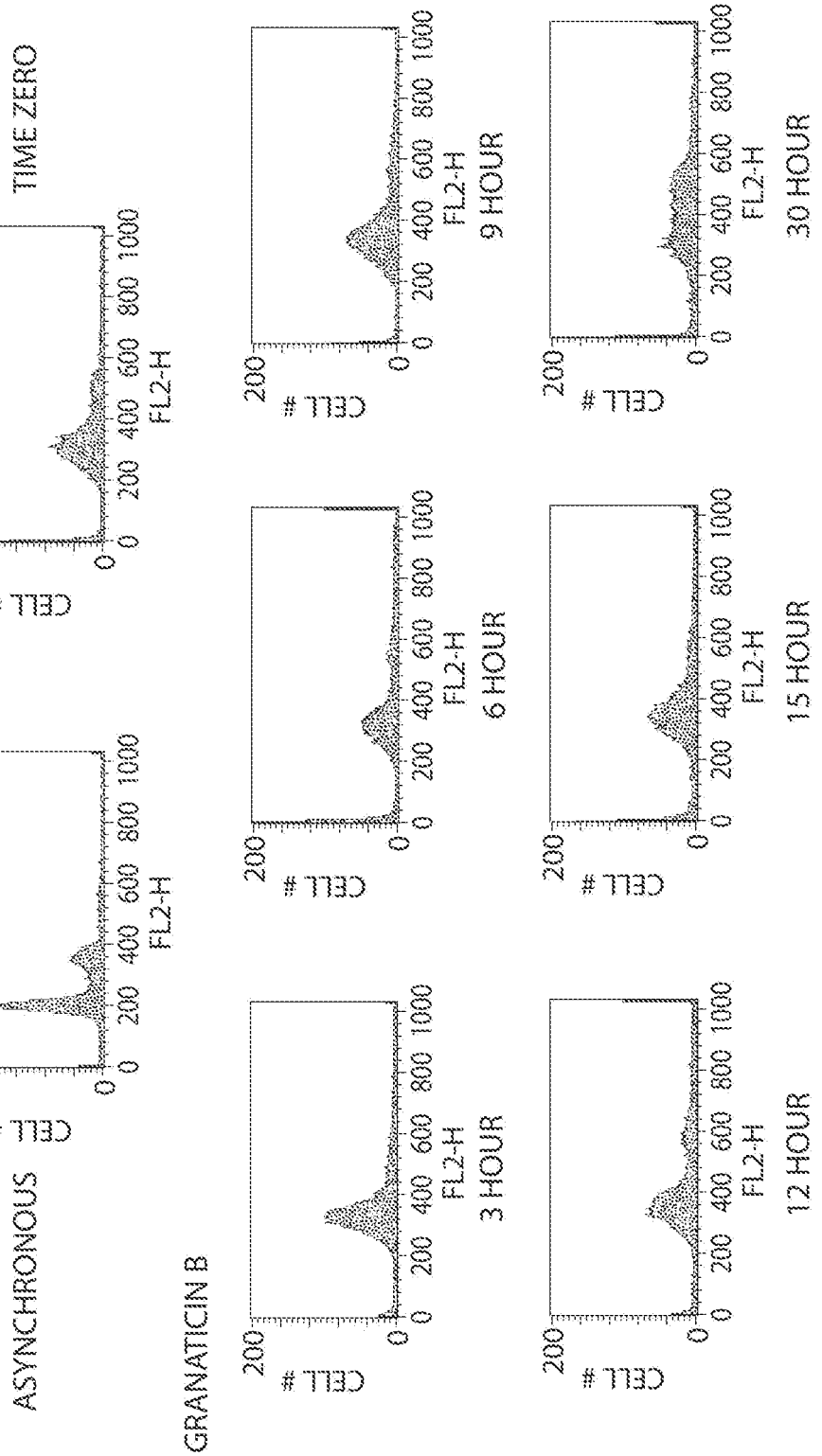
FIG. 10. Granaticin B Induces Cell Cycle Arrest of Hela S3 Cells: An identical experiment to that described in FIG. 9 was performed using granaticin B and revealed similar results.
Figure 12:
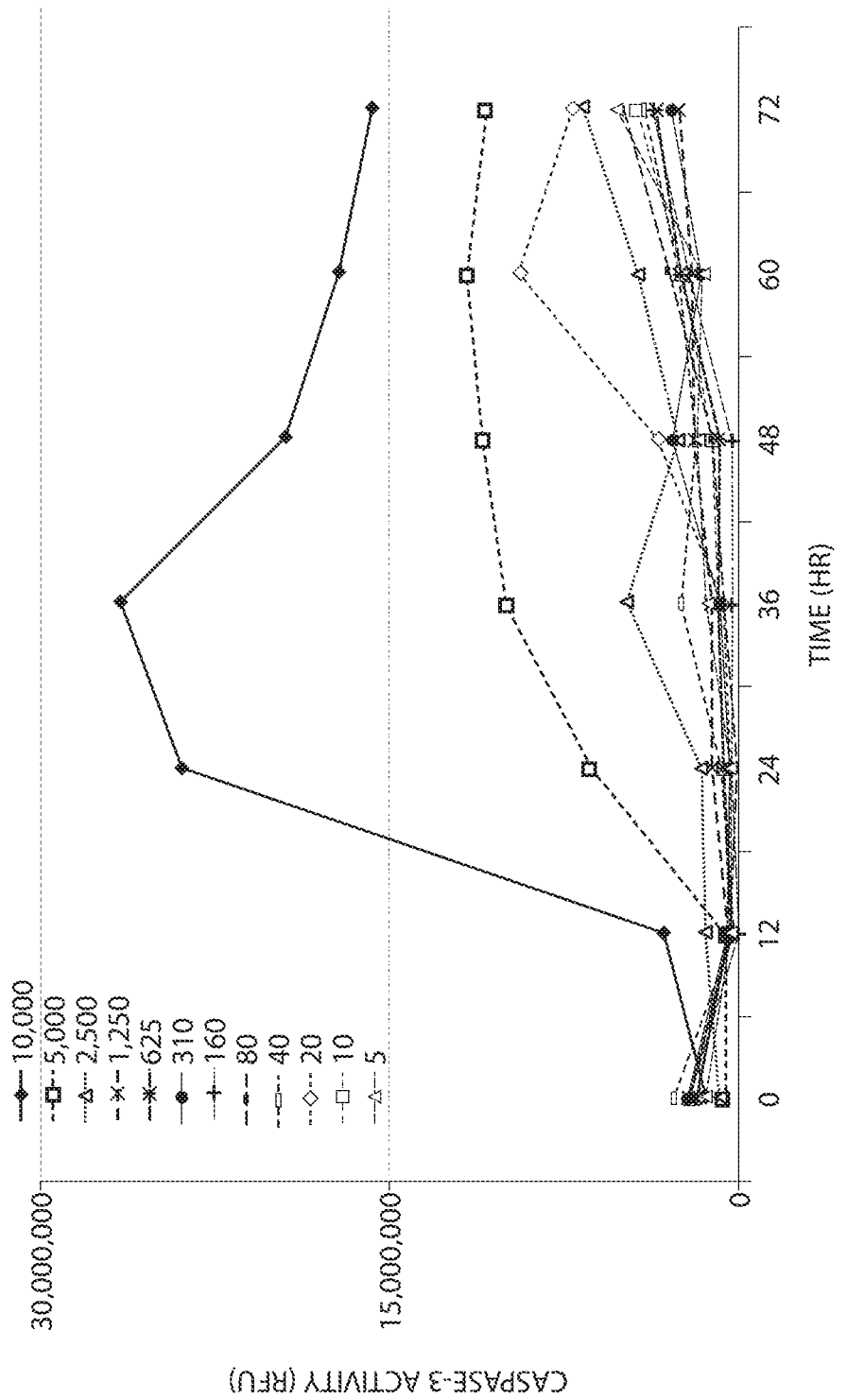
FIGS. 12-14. Inhibition of Granaticin A Induced Caspase-3 Activity in HeLa cells. Growth curves in the presence of the indicated micromolar concentrations of granaticin A were performed and caspase-3 activity was measured following addition of a substrate that when cleaved by caspase-3 results in light emission which is quantitated by a fluorimeter (y-axis) as a function of time (x-axis).
Figure 13:
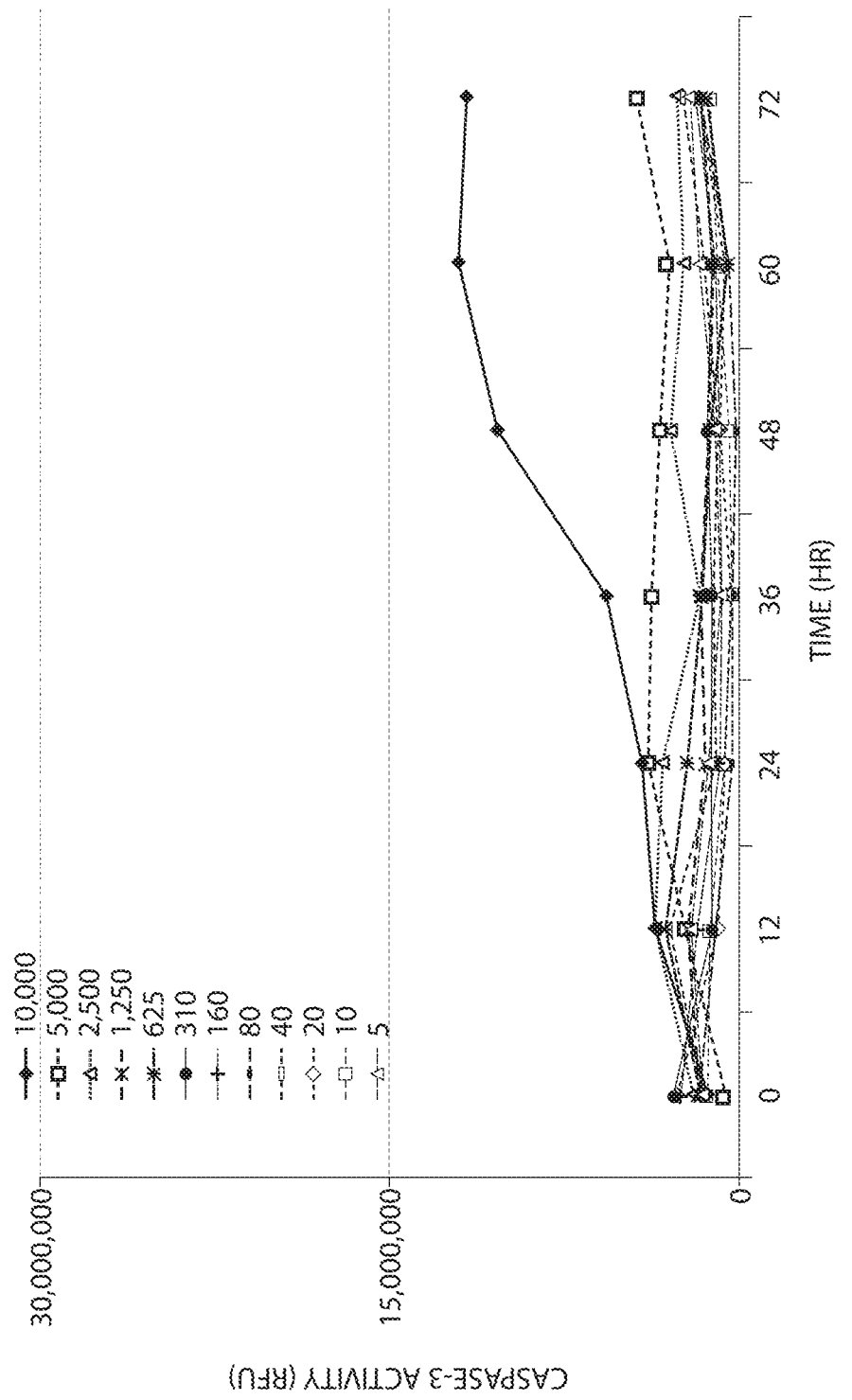
Figure 14:
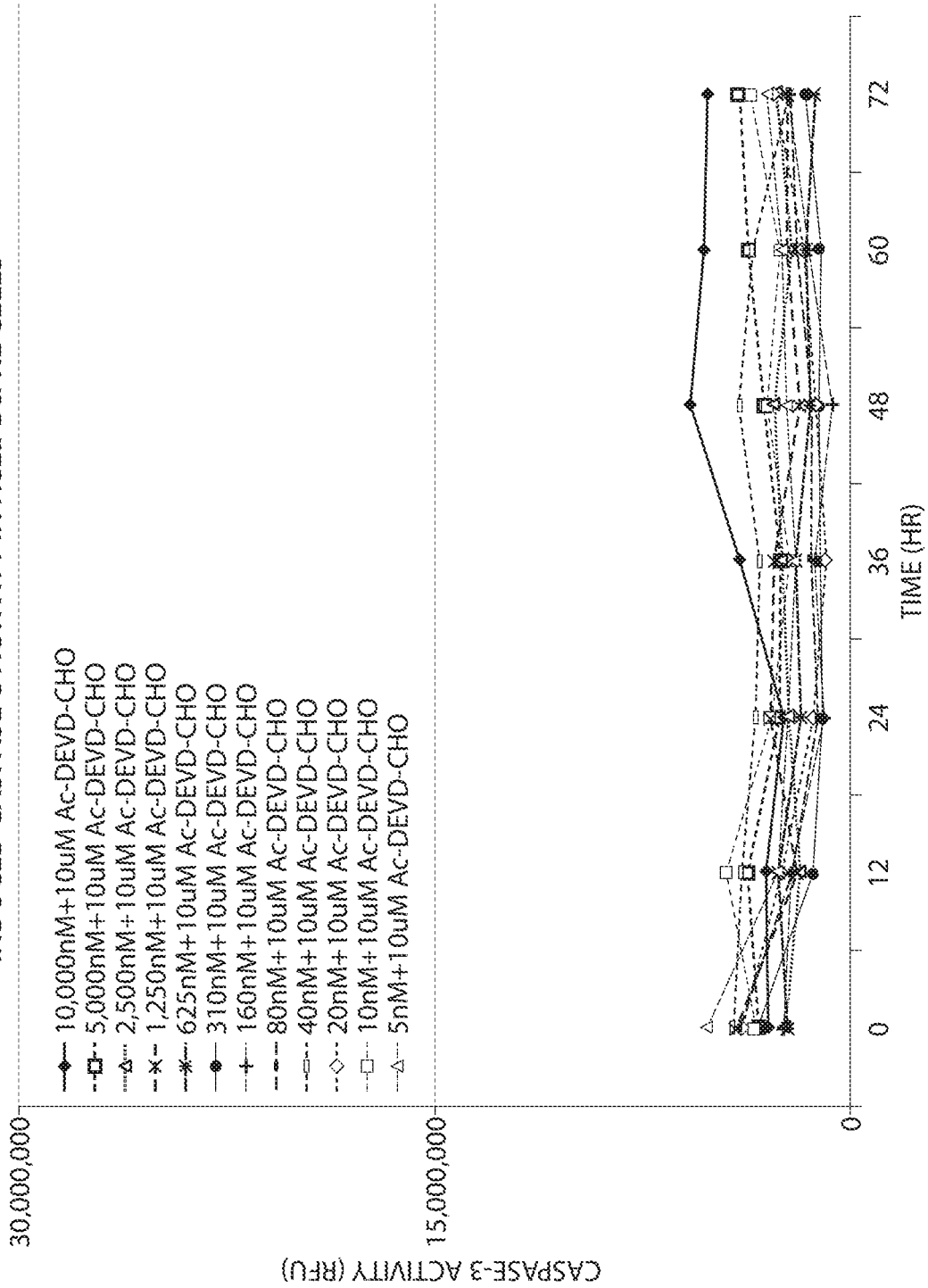
Figure 15:
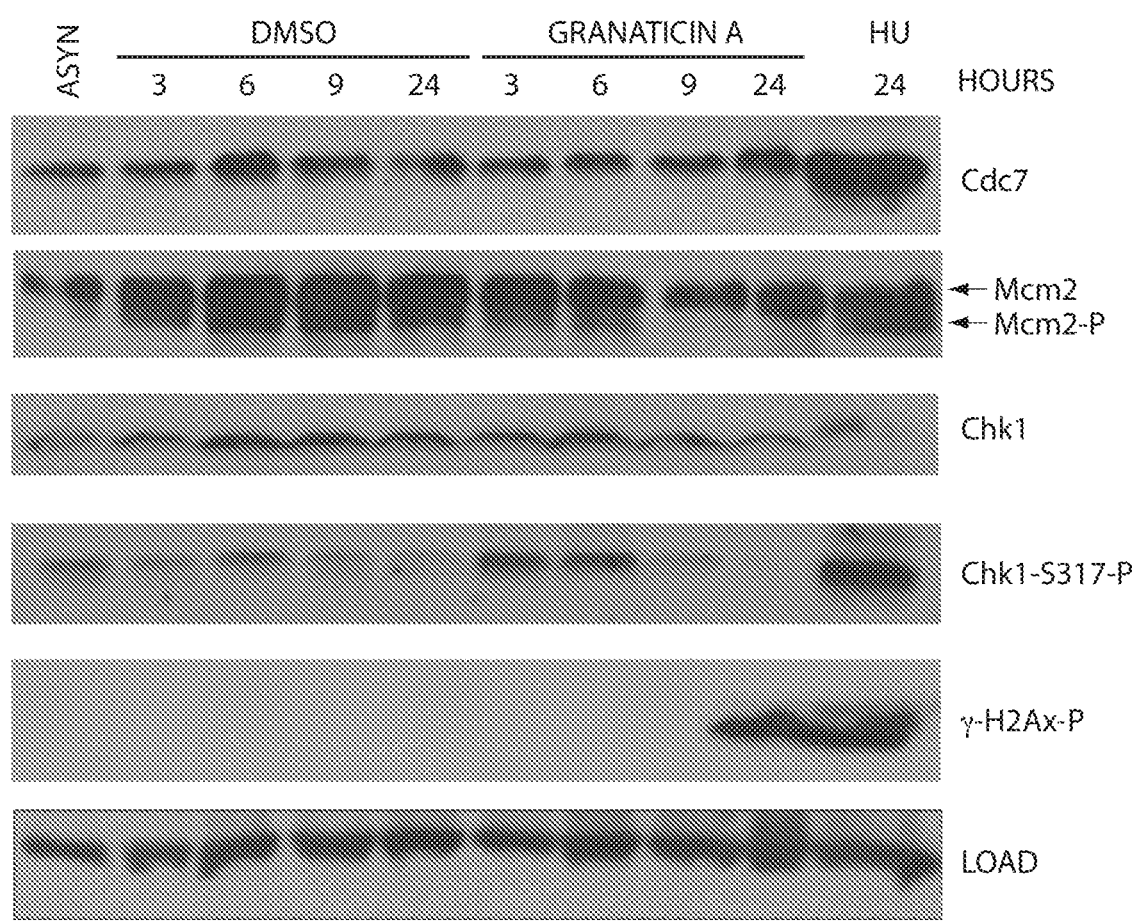
FIG. 15. Granaticin A Does Not Activate the S Phase Checkpoint in HeLa Cells: Exposure of HeLa cells to granaticin A does not activate the S phase checkpoint and results in increased double strand DNA breaks. HeLa cells were incubated in the presence of granaticin A or carrier control (DMSO) for the indicated times and whole cell extracts were subjected to SDS-PAGE and western blot analysis. Asyn=asynchronously growing HeLa cells. HU=HeLa cells exposed to hydroxyurea for the indicated time. HU was used as a control for DNA damaging agent that is known to inhibit the DNA damage checkpoint response. Again, we observed that Mcm2 mobility is shifted in the cells treated with granaticin A. MCM2 mobility is not affected by HU. Activation of the DNA damage/replication checkpoint correlates with ATM/ATR dependent phosphorylation of Chk1 at Ser345. ChK1 Ser345 levels are below detection limits, suggesting that with Cdc7 inhibition, a DNA replication checkpoint is either not efficiently activated or maintained and that inhibitory signals preventing cells from progressing in the cell cycle might not be generated.

The current invention derives from the discovery that the benzoisochromane quinones (BIQs), such as the granaticins, inhibit protein kinase activity. The granaticins, in particular, were found to inhibit Cdc kinase activity based upon hits identified from high-thoroughput screening (HTS) of over 300,000 compounds for their ability to inhibit a heterodimer of a kinase (Cdc7) and an activator (Dbf4) that phosphorylates serine and threonine residues.

The present invention provides methods for the inhibition of protein kinase activity, such as Cdc kinase activity, and particularly, Cdc7 kinase activity. The inhibitory compounds useful in the methods include, but are not limited to, granaticin A, granaticin B, dihydrogranaticin A, dihydrogranaticin B, medermycin, actinorhodin, benzoisochromanequinones, as shown herein. The methods of the present invention are useful in the treatment of kinase-related diseases or disorders. Specifically, the methods are useful in the treatment of proliferative disorders, such as cancer, benign tumors, inflammatory disorders, and complications thereof. The present invention also provides pharmaceutical compositions and kits for the treatment of various diseases.

Compounds Useful in the Invention

The present invention utilizes compounds of the Formula (A):

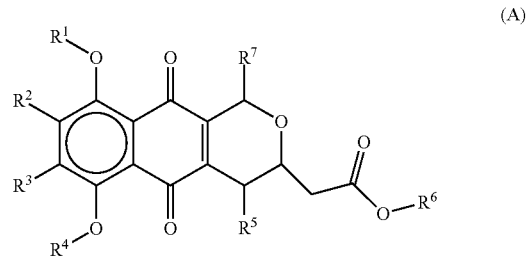

(A)

or pharmaceutically acceptable salts thereof,
wherein:

each instance of $R^1$ and $R^4$ is independently selected from the group consisting of hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of $R^2$ and $R^3$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^2$ and $R^3$ are joined to form an optionally substituted carbocyclyl, optionally substituted heterocyclyl, optionally substituted aryl, or optionally substituted heteroaryl group;

$R^5$ is hydrogen and $R^6$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl; or $R^5$ and $R^6$ are joined to form a direct bond; and $R^7$ is hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^1$ is hydrogen. In certain embodiments, $R^1$ is carbonyl, silyl, optionally substituted carbocyclyl, optionally substituted heterocyclyl, optionally substituted aryl, or optionally substituted heteroaryl.

In certain embodiments, $R^4$ is hydrogen. In certain embodiments, $R^4$ is optionally substituted carbocyclyl, optionally substituted heterocyclyl, optionally substituted aryl, or optionally substituted heteroaryl.

In certain embodiments, both $R^1$ and $R^4$ are hydrogen, e.g., to provide a compound of the Formula (A-1):

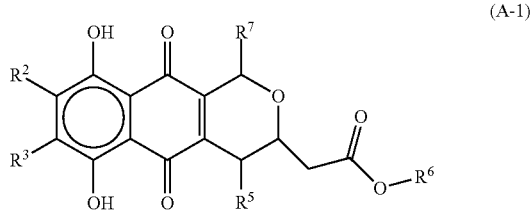

(A-1)

or a pharmaceutically acceptable salt thereof,
wherein $R^3$, $R^4$, $R^5$, $R^6$, and $R^7$ are as defined herein.

In certain embodiments, $R^2$ is hydrogen. In certain embodiments, $R^2$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^2$ is optionally substituted carbocyclyl, optionally substituted heterocyclyl, optionally substituted aryl, or optionally substituted heteroaryl. In certain embodiments, $R^2$ is optionally substituted heterocyclyl (e.g., optionally substituted tetrahydropyranyl).

In certain embodiments, $R^2$ is an optionally substituted tetrahydropyranyl group of the formula (i):

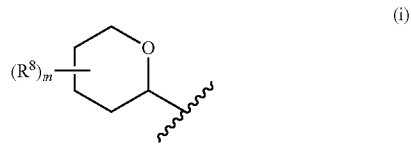

(i)

wherein:
each instance of $R^8$ is independently selected from optionally substituted alkyl, optionally substituted alkenyl, optionally substituted alkynyl, optionally substituted carbocyclyl, optionally substituted heterocyclyl, optionally substituted aryl, optionally substituted heteroaryl, —OH, substituted hydroxyl, —SH, substituted thiol, —NH$_2$, substituted amino, —CN, —NO$_2$, —N$_2$, carbonyl, silyl, sulfonyl, and sulfinyl; and m is 0 or an integer of between 1 and 5, inclusive.

In certain embodiments, each instance of $R^8$ is independently selected from optionally substituted alkyl, —OH, substituted hydroxyl, —SH, substituted thiol, —NH$_2$, substituted amino, carbonyl, and silyl. In certain embodiments, each instance of $R^7$ is independently selected from optionally substituted alkyl, —OH, substituted hydroxyl, —NH$_2$, and substituted amino. In certain embodiments, each instance of $R^8$ is independently selected from optionally substituted alkyl, —OH, and substituted amino (e.g., disubstituted amino). In certain embodiments, each instance of $R^8$ is independently selected from —CH$_3$, —OH, and —N(CH$_3$)$_2$.

In certain embodiments, m is an integer of between 1 and 4, inclusive. In certain embodiments, m is an integer of between 1 and 3, inclusive. In certain embodiments, m is an integer of between 1 and 2, inclusive. In certain embodiments, m is 3.

In certain embodiments, each instance of $R^8$ is independently selected from —CH$_3$, —OH, and —N(CH$_3$)$_2$, and m is an integer of between 1 and 3, inclusive. For example, in this instance, in certain embodiments, $R^2$ is a substituted tetrahydropyranyl group of the formula (ii):

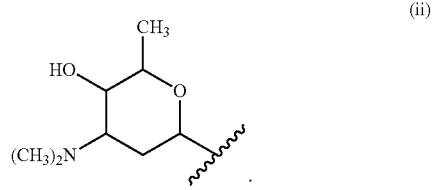

(ii)

In certain embodiments, the substituted tetrahydropyranyl group of the formula (ii) is of the formula (iii):

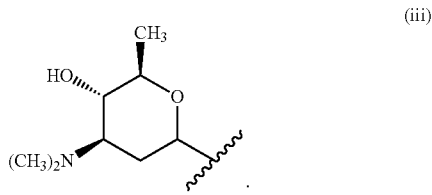

(iii)

Alternatively, in certain embodiments, $R^2$ is an optionally substituted aryl or optionally substituted heteroaryl. In certain embodiments, $R^2$ is an optionally substituted aryl (e.g., a benzoisochromanequinone).

In certain embodiments $R^2$ is substituted benzoisochromanequinone of the formula (iv):

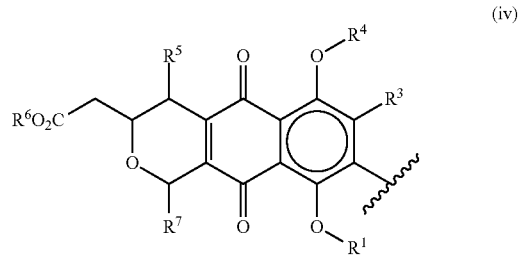

(iv)

wherein $R^1$, $R^3$, $R^4$, $R^5$, $R^6$, and $R^7$ are as defined herein.

In certain embodiments, the substituted benzoisochromanequinone of formula (iv) is of the formula (v):

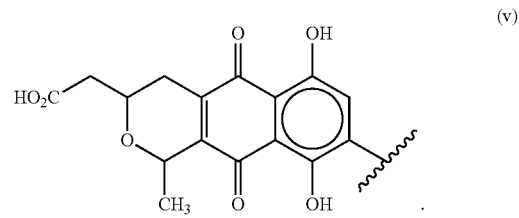

(v)

Alternatively, in certain embodiments, $R^2$ and $R^3$ are joined to form an optionally substituted carbocyclyl, optionally substituted heterocyclyl, optionally substituted aryl, or optionally substituted heteroaryl group. In certain embodiments, $R^2$ and $R^3$ are joined to form an optionally substituted carbocyclyl or optionally substituted heterocyclyl group. In certain embodiments, $R^2$ and $R^3$ are joined to form an optionally substituted heterocyclyl group (e.g., an optionally substituted 2-oxabicyclo[2.2.2]octenyl group).

In certain embodiments, $R^2$ and $R^3$ are joined to form a substituted 2-oxabicyclo[2.2.2]octenyl group of the formula (vi):

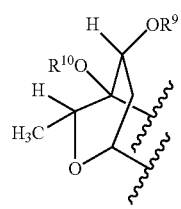

(vi)

wherein each instance of $R^9$ and $R^{10}$ is independently selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, sulfonyl, and sulfinyl.

In certain embodiments, $R^9$ is hydrogen. In certain embodiments, $R^9$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^9$ is optionally substituted carbocyclyl or optionally substituted heterocyclyl. In certain embodiments, $R^9$ is optionally substituted heterocyclyl (e.g., optionally substituted tetrahydropyranyl).

In certain embodiments, $R^9$ is optionally substituted tetrahydropyranyl group of the formula (vii):

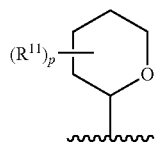

(vii)

wherein:
each instance of $R^{11}$ is independently selected from optionally substituted alkyl, optionally substituted alkenyl, optionally substituted alkynyl, optionally substituted carbocyclyl, optionally substituted heterocyclyl, optionally substituted aryl, optionally substituted heteroaryl, —OH, substituted hydroxyl, —SH, substituted thiol, —NH$_2$, substituted amino, —CN, —NO$_2$, —N$_3$, carbonyl, silyl, sulfonyl, and sulfinyl; and
p is 0 or an integer of between 1 and 5, inclusive.

In this instance, in certain embodiments, the $R^2$ and $R^3$ are joined to form a substituted 2-oxabicyclo[2.2.2]octenyl group of the formula (viii):

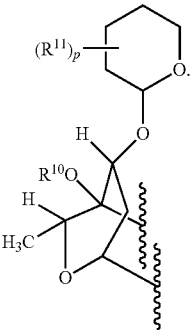

(viii)

In certain embodiments, each instance of $R^{11}$ is independently selected from optionally substituted alkyl, —OH, substituted hydroxyl, —SH, substituted thiol, —NH$_2$, substituted amino, carbonyl, and silyl. In certain embodiments, each instance of $R^{10}$ is independently selected from optionally substituted alkyl, —OH, and substituted hydroxyl. In certain embodiments, each instance of $R^{11}$ is independently selected from optionally substituted alkyl and —OH. In certain embodiments, each instance of $R^{11}$ is independently selected from —CH$_3$ and —OH.

In certain embodiments, p is an integer of between 1 and 4, inclusive. In certain embodiments, p is an integer of between 1 and 3, inclusive. In certain embodiments, p is an integer of between 1 and 2, inclusive. In certain embodiments, p is 2.

In certain embodiments, each instance of $R^{11}$ is independently selected from —CH$_3$ and —OH, and p is an integer of between 1 and 2, inclusive. For example, in this instance, in certain embodiments, $R^{11}$ is a substituted tetrahydropyranyl group of the formula (ix):

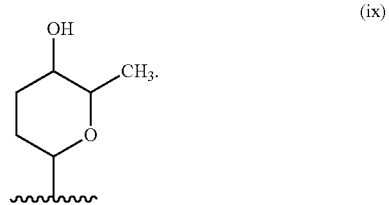 [SMILES: *C1CCC(O)C(C)O1]

(ix)

In certain embodiments, the substituted tetrahydropyranyl group of the formula (ix) is of the formula (x):

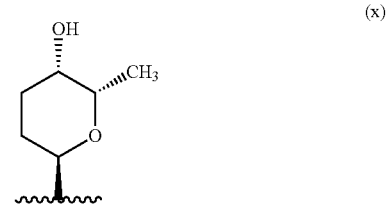 [SMILES: *[C@H]1CC[C@H](O)[C@H](C)O1]

(x)

In this instance, in certain embodiments, the $R^2$ and $R^3$ are joined to form a substituted 2-oxabicyclo[2.2.2]octenyl group of the formula (xi):

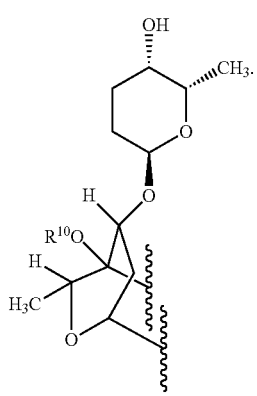

(xi)

In certain embodiments, $R^{10}$ is optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, sulfonyl, or sulfinyl.

However, in certain embodiments, $R^{10}$ is hydrogen. In this instance, in certain embodiments, the $R^2$ and $R^3$ are joined to form a substituted 2-oxabicyclo[2.2.2]octenyl group of the formula (xii):

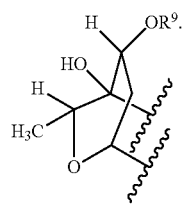

(xii)

In certain embodiments, both $R^9$ and $R^{10}$ are hydrogen. In this instance, in certain embodiments, the $R^2$ and $R^3$ are joined to form a substituted 2-oxabicyclo[2.2.2]octenyl group of the formula (xiii):

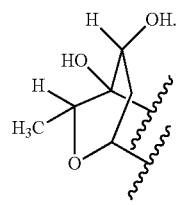

(xiii)

In certain embodiments, $R^5$ is hydrogen and $R^6$ is selected from the group consisting of selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl.

In certain embodiments, both $R^5$ and $R^6$ are hydrogen. However, in certain embodiments, $R^5$ is hydrogen and $R^6$ is optionally substituted alkyl, optionally substituted alkenyl, optionally substituted alkynyl, optionally substituted carbocyclyl, optionally substituted heterocyclyl, optionally substituted aryl, optionally substituted heteroaryl.

Alternatively, in certain embodiments, $R^5$ and $R^6$ are joined to form a direct bond, e.g., to provide a dihydrofuran-2-one of the formula (xiv):

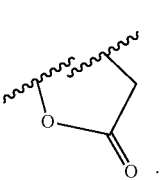

(xiv)

In certain embodiments, the dihydrofuran-2-one of the formula (xiv) is of the formula (xv):

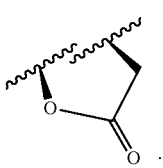

(xv)

In certain embodiments, the dihydrofuran-2-one of the formula (xiv) is of the formula (xvi):

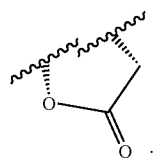

(xvi)

In certain embodiments, $R^7$ is hydrogen. In certain embodiments, $R^7$ is optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^7$ is optionally substituted alkyl (e.g., —$CH_3$, —$CH_2CH_3$, —$CH_2CH_2CH_3$, —$CH(CH_3)_2$, and the like). In certain embodiments, $R^7$ is —$CH_3$.

In certain embodiments, wherein $R^5$ and $R^6$ are joined to form a direct bond, i.e., to provide a dihydrofuran-2-one of the formula (xiv), the compound of Formula (A) is of the Formula (A-2):

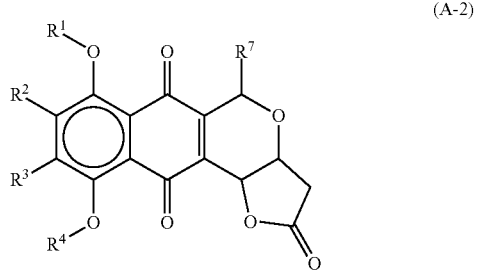

(A-2)

or a pharmaceutically acceptable salt thereof. In certain embodiments, $R^7$ is —$CH_3$. In certain embodiments, $R^1$ and $R^4$ are hydrogen.

In certain embodiments, wherein $R^5$ and $R^6$ are joined to form a dihydrofuran-2-one of the formula (xv), the compound of Formula (A-2) is of the Formula (A-3):

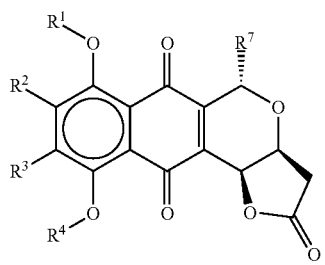

(A-3)

or a pharmaceutically acceptable salt thereof. In certain embodiments, $R^7$ is —$CH_3$. In certain embodiments, $R^1$ and $R^4$ are hydrogen.

In certain embodiments, wherein $R^5$ and $R^6$ are joined to form a dihydrofuran-2-one of the formula (xvi), the compound of Formula (A-2) is of the Formula (A-4):

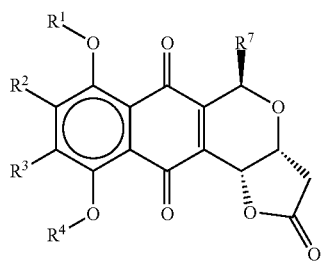

(A-4)

or a pharmaceutically acceptable salt thereof. In certain embodiments, $R^7$ is —$CH_3$. In certain embodiments, $R^1$ and $R^4$ are hydrogen.

In certain embodiments, wherein $R^1$ and $R^4$ are hydrogen, the compound of Formula (A-3) is of the Formula (A-5):

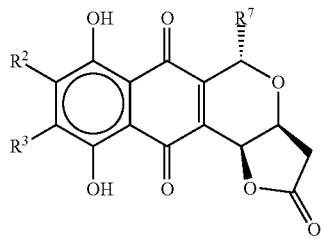

(A-5)

or a pharmaceutically acceptable salt thereof. In certain embodiments, $R^7$ is —$CH_3$.

In certain embodiments, wherein $R^1$ and $R^4$ are hydrogen, the compound of Formula (A-4) is of the Formula (A-6):

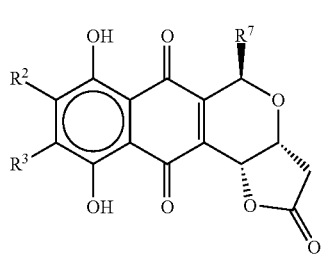

(A-6)

or a pharmaceutically acceptable salt thereof. In certain embodiments, $R^7$ is —$CH_3$.

In certain embodiments, wherein $R^2$ and $R^3$ are joined to form a substituted oxabicyclo[2.2.2]octenyl group of the formula (vi), the compound of Formula (A-5) is of the Formula (A-7):

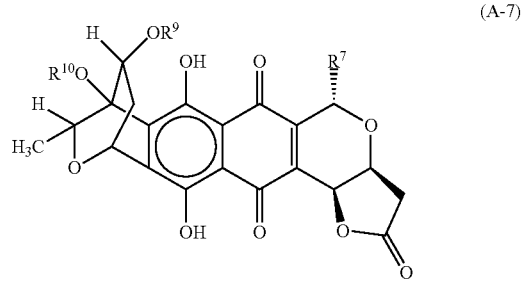

(A-7)

or a pharmaceutically acceptable salt thereof. In certain embodiments, $R^7$ is —$CH_3$.

Exemplary compounds of the Formula (A) include, but are not limited to:

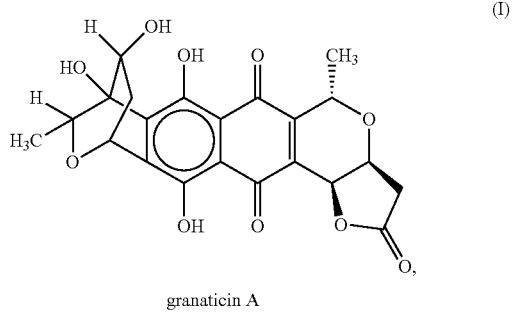

(I)

granaticin A

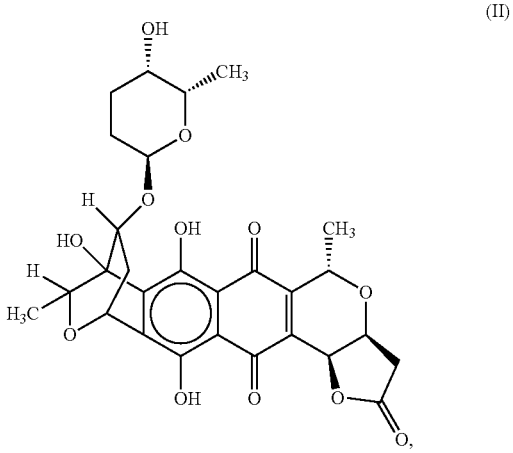

(II)

granaticin B

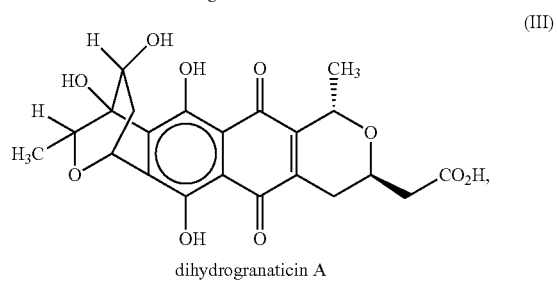

(III)

dihydrogranaticin A

-continued

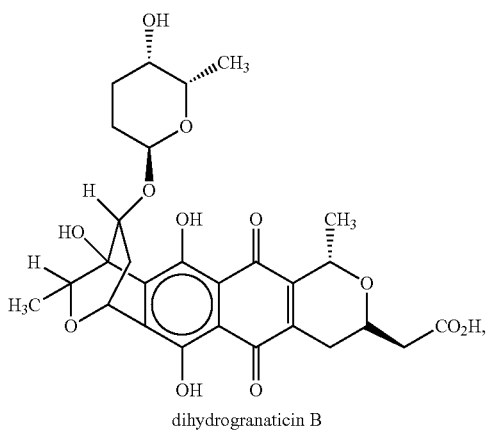

dihydrogranaticin B

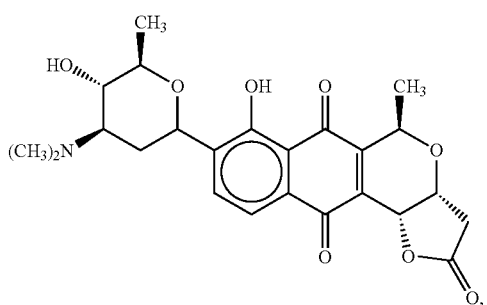

medermycin

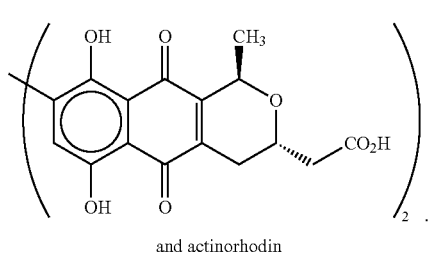

and actinorhodin or pharmaceutically acceptable salts thereof.

The present invention also utilizes compounds of the Formula (B):

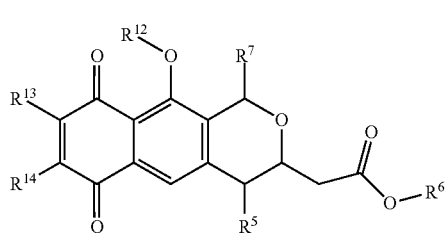

or pharmaceutically acceptable salts thereof,
wherein:
$R^{12}$ is hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl;
each instance of $R^{13}$ and $R^{14}$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^{13}$ and $R^{14}$ are joined to form an optionally substituted carbocyclyl, optionally substituted heterocyclyl, optionally substituted aryl, or optionally substituted heteroaryl group;
$R^5$ is hydrogen and $R^6$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl; or $R^5$ and $R^6$ are joined to form a direct bond; and
$R^7$ is hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl.

In certain embodiments, $R^{12}$ is hydrogen. In certain embodiments, $R^{12}$ is carbonyl, silyl, optionally substituted carbocyclyl, optionally substituted heterocyclyl, optionally substituted aryl, or optionally substituted heteroaryl.

In certain embodiments, $R^{13}$ is hydrogen. In certain embodiments, $R^{13}$ is halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^{13}$ is —OH, substituted hydroxyl, —SH, substituted thiol, —NH$_2$, substituted amino. In certain embodiments, $R^{13}$ is —OH or substituted hydroxyl. In certain embodiments, $R^{13}$ is —OH.

In certain embodiments, $R^{14}$ is hydrogen. In certain embodiments, $R^{14}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{14}$ is optionally substituted carbocyclyl, optionally substituted heterocyclyl, optionally substituted aryl, or optionally substituted heteroaryl. In certain embodiments, $R^{14}$ is optionally substituted heterocyclyl (e.g., optionally substituted tetrahydropyranyl).

In certain embodiments, $R^{14}$ is an optionally substituted tetrahydropyranyl group of the formula (xvii):

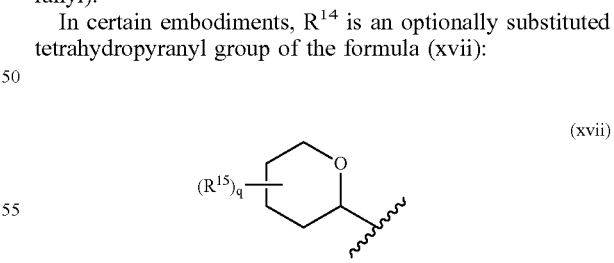

wherein:
each instance of $R^{15}$ is independently selected from optionally substituted alkyl, optionally substituted alkenyl, optionally substituted alkynyl, optionally substituted carbocyclyl, optionally substituted heterocyclyl, optionally substituted aryl, optionally substituted heteroaryl, —OH, substituted hydroxyl, —SH, substituted thiol, —NH$_2$, substituted amino, —CN, —NO$_2$, carbonyl, silyl, sulfonyl, and sulfinyl; and q is 0 or an integer of between 1 and 5, inclusive.

In certain embodiments, each instance of $R^{15}$ is independently selected from optionally substituted alkyl, —OH, substituted hydroxyl, —SH, substituted thiol, —NH$_2$, substituted amino, carbonyl, and silyl. In certain embodiments, each instance of $R^{15}$ is independently selected from optionally substituted alkyl, —OH, substituted hydroxyl, —NH$_2$, and substituted amino. In certain embodiments, each instance of $R^{15}$ is independently selected from optionally substituted alkyl, —OH, and substituted hydroxyl. In certain embodiments, each instance of $R^{15}$ is independently selected from —CH$_3$ and —OH.

In certain embodiments, q is an integer of between 1 and 4, inclusive. In certain embodiments, q is an integer of between 1 and 3, inclusive. In certain embodiments, q is an integer of between 1 and 2, inclusive. In certain embodiments, q is 3.

In certain embodiments, each instance of $R^{15}$ is independently selected from —CH$_3$, —OH, and m is an integer of between 1 and 3, inclusive. For example, in this instance, in certain embodiments, $R^{15}$ is a substituted tetrahydropyranyl group of the formula (xviii):

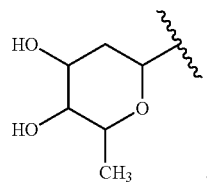

(xviii)

Alternatively, in certain embodiments, $R^{13}$ and $R^{14}$ are joined to form an optionally substituted carbocyclyl, optionally substituted heterocyclyl, optionally substituted aryl, or optionally substituted heteroaryl group. In certain embodiments, $R^{13}$ and $R^{14}$ are joined to form an optionally substituted carbocyclyl or optionally substituted heterocyclyl group. In certain embodiments, $R^{13}$ and $R^{14}$ are joined to form an optionally substituted heterocyclyl group (e.g., an optionally substituted 2-oxabicyclo[2.2.2]octenyl group).

In certain embodiments, $R^{13}$ and $R^{14}$ are joined to form a substituted 2-oxabicyclo[2.2.2]octenyl group of the formula (xix):

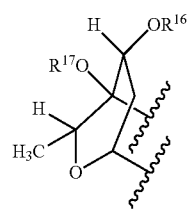

(xix)

wherein each instance of $R^{16}$ and $R^{17}$ is independently selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, carbonyl, silyl, sulfonyl, and sulfinyl.

In certain embodiments, $R^{16}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{16}$ is optionally substituted carbocyclyl or optionally substituted heterocyclyl. However, in certain embodiments, $R^{16}$ is hydrogen, e.g., and $R^{13}$ and $R^{14}$ are joined to form a substituted 2-oxabicyclo[2.2.2]octenyl group of the formula (xx):

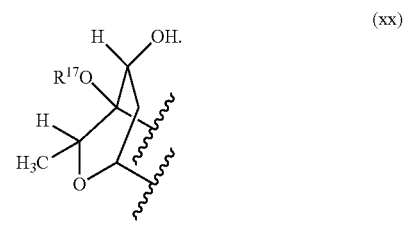

(xx)

In certain embodiments, $R^{17}$ is optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^{17}$ is optionally substituted carbocyclyl or optionally substituted heterocyclyl. However, in certain embodiments, $R^{17}$ is hydrogen, e.g., and $R^{13}$ and $R^{14}$ are joined to form a substituted 2-oxabicyclo[2.2.2]octenyl group of the formula (xxi):

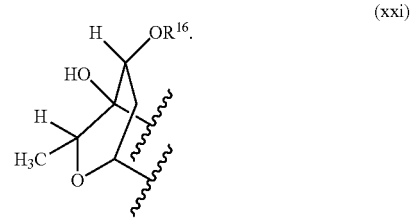

(xxi)

In certain embodiments, both $R^{16}$ and $R^{17}$ are hydrogen. In this instance, in certain embodiments, the $R^{13}$ and $R^{14}$ are joined to form a substituted 2-oxabicyclo[2.2.2]octenyl group of the formula (xxii):

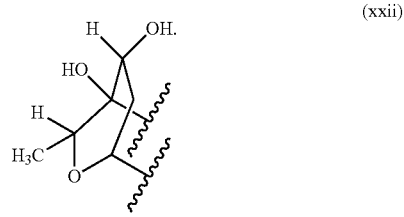

(xxii)

In certain embodiments, $R^5$ is hydrogen and $R^6$ is selected from the group consisting of selected from hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl.

In certain embodiments, both $R^5$ and $R^6$ are hydrogen. However, in certain embodiments, $R^5$ is hydrogen and $R^6$ is optionally substituted alkyl, optionally substituted alkenyl, optionally substituted alkynyl, optionally substituted carbocyclyl, optionally substituted heterocyclyl, optionally substituted aryl, optionally substituted heteroaryl.

Alternatively, in certain embodiments, $R^5$ and $R^6$ are joined to form a direct bond, e.g., to provide a dihydrofuran-2-one of the formula (xiv):

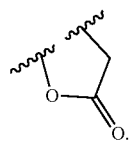
(xiv)

In certain embodiments, the dihydrofuran-2-one of the formula (xiv) is of the formula (xv):

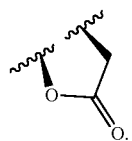
(xv)

In certain embodiments, the dihydrofuran-2-one of the formula (xiv) is of the formula (xvi):

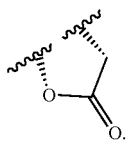
(xvi)

In certain embodiments, $R^7$ is hydrogen. In certain embodiments, $R^7$ is optionally substituted alkyl, optionally substituted alkenyl, optionally substituted alkynyl, optionally substituted carbocyclyl, optionally substituted heterocyclyl, optionally substituted aryl, and optionally substituted heteroaryl. In certain embodiments, $R^7$ is optionally substituted alkyl (e.g., —$CH_3$, —$CH_2CH_3$, —$CH_2CH_2CH_3$, —$CH(CH_3)_2$, and the like). In certain embodiments, $R^7$ is —$CH_3$.

In certain embodiments, wherein $R^{12}$ is hydrogen, the compound of Formula (B) is of the Formula (B-1):

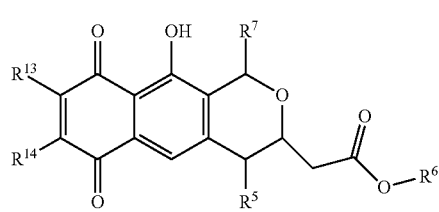
(B-1)

or a pharmaceutically acceptable salt thereof. In certain embodiments, $R^7$ is —$CH_3$.

In certain embodiments, wherein $R^5$ and $R^6$ are joined to form a direct bond, the compound of Formula (B-1) is of the Formula (B-2):

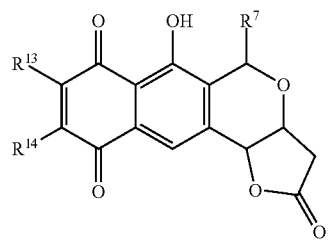
(B-2)

or a pharmaceutically acceptable salt thereof. In certain embodiments, $R^7$ is —$CH_3$.

In certain embodiments, wherein $R^{13}$ and $R^{14}$ are joined to form a substituted 2-oxabicyclo[2.2.2]octenyl group of the formula (xix), the compound of Formula (B-1) is of the Formula (B-3):

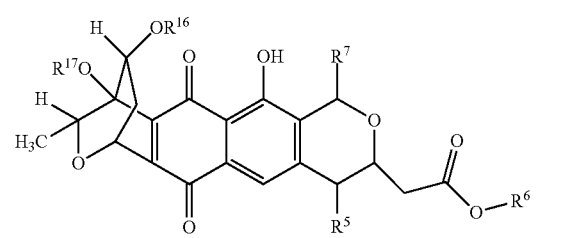
(B-3)

or a pharmaceutically acceptable salt thereof. In certain embodiments, $R^7$ is —$CH_3$.

In certain embodiments, wherein $R^{13}$ is —OH and $R^{14}$ is an optionally substituted tetrahydropyranyl group of the formula (xvii), the compound of Formula (B-1) is of the Formula (B-4):

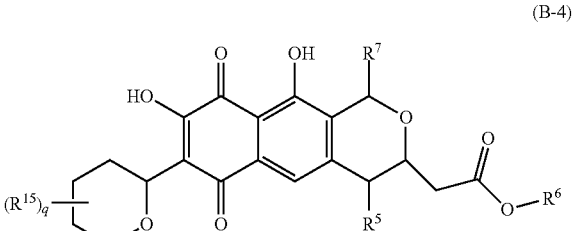
(B-4)

or a pharmaceutically acceptable salt thereof. In certain embodiments, $R^7$ is —$CH_3$.

Exemplary compounds of the Formula (B) include, but are not limited to:

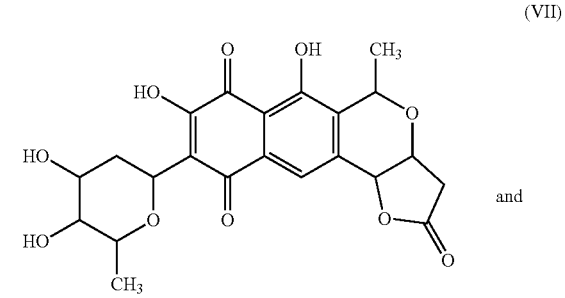
(VII)

and

Derivative 1

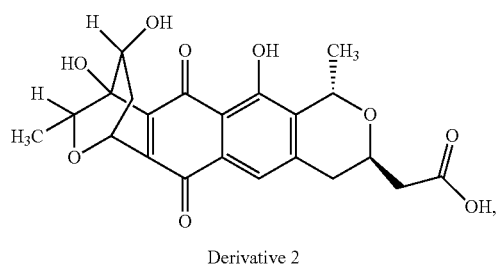

Derivative 2 or pharmaceutically acceptable salts thereof.

In certain embodiments, the compounds of Formula (A) and (B) have an $IC_{50}$ of less than approximately 100 μM, e.g., less than approximately 10 μM, e.g., less than approximately 1 μM, e.g., less than approximately 0.1 μM, or e.g., less than approximately 0.01 μM.

The compounds described herein may be useful in methods, pharmaceutical compositions, and kits, for example, in the treatment and prevention of proliferative disorders, such as cancer, benign tumors, inflammatory disorders, and complications thereof.

Protein Kinases, Cdc7, and Dbf4

Compounds useful in the present invention are protein kinase inhibitors. The protein kinases constitute a group of enzymes that catalyse the phosphorylation of hydroxy groups of specific protein residues such as tyrosine, serine or threonine residues. Said phosphorylations can extensively modify the function of proteins; thus, the protein kinases play an important role in the regulation of a great variety of cellular processes, notably including metabolism, cellular proliferation, cell differentiation or cell survival. Among the various cellular functions in which the activity of a protein kinase is involved, certain processes represent attractive targets for treating certain diseases. As an example, we may notably mention angiogenesis and control of the cell cycle, in which the protein kinases can play an essential role. These processes are essential for the growth of solid tumours as well as for the development of other diseases.

The protein kinases participate in signalling events that control the activation, growth and differentiation of cells in response either to extracellular mediators, or to changes in the environment. In general, these kinases belong to two groups: those which phosphorylate serine and/or threonine residues preferentially, and those which phosphorylate tyrosine residues preferentially (S. K. Hanks and T. Hunter, FASEB. J., 1995, 9, pages 576-596). The serine/threonine kinases, for example, are isoforms of protein kinases C (A. C. Newton, J. Biol. Chem., 1995, 270, pages 28495-28498) and a group of cyclin-dependent kinases, such as Cdc2 (Cdk1) (J. Pines, Trends in Biochemical Sciences, 1995, 18, pages 195-197). The tyrosine kinases include growth factor receptors, such as the epidermal growth factor (EGF) receptor (S. Iwashita and M. Kobayashi, Cellular Signalling, 1992, 4, pages 123-132), and cytosolic kinases such as p56tck, p59fYn, ZAP-70 and the csk kinases (C. Chan et al., Ann. Rev. Immunol., 1994, 12, pages 555-592).

Abnormally high levels of protein kinase activity have been associated with many diseases, resulting in abnormal cellular functions. This can occur either directly or indirectly, from a malfunction in the control mechanisms of kinase activity, connected for example with a mutation, overexpression or inappropriate activation of the enzyme, or with overproduction or underproduction of cytokines or of growth factors, which are also involved in signal transduction upstream or downstream of the kinases. In all these cases, selective inhibition of the action of the kinases offers hope of a beneficial effect. Among these protein kinases, we may mention quite particularly protein kinase Cdc7. Cdc7 is a serine/threonine kinase that has been characterized at the molecular level as a factor that is essential for initiating DNA replication.

The catalytic activity of Cdc7, which is conserved throughout the eukaryotes, is dependent on its Dbf4 regulatory subunit. Although the expression of Cdc7 (at the level of messenger and protein RNA) is constant throughout the cell cycle, the level of expression of Dbf4 is in contrast dependent on the cell cycle, which induces an increase in Cdc7 kinase activity during the G1-S transition. For this reason, Cdc7 is given the designation DDK (Dbf-4-dependent kinase).

The principal activity of the Cdc7/Dbf4 complex occurs on initiation of DNA replication during the S phase. It phosphorylates MCM2 which thus activates the MCM (MiniChromosome Maintenance) complex, which is an essential component of DNA-helicase activity.

Cdc7 also plays an important role in mutagenesis, mainly induced by action at the level of the DNA-damage pathways and checkpoints, in particular at the ATR-dependent checkpoint, which prevents the initiation of DNA replication in response to damage of the single-stranded type caused by chemical agents such as etoposide.

Cdc7 and Dbf4 are overexpressed in human tumour cell lines and in many tumour samples (lung, breast, thyroid, colon-rectum, oesophagus, uterus, testicle, liver) in comparison with the corresponding normal tissues (Hess, G. F., Drong, R. F., et al. 1998).

Experiments in suppressing Cdc7 expression using RNA interference (RNAi) technology show that inhibition of Cdc7 expression induces arrest of the cell cycle and prevents cellular proliferation of the human tumour cell lines HeLa and HCT116, but has a limited effect on normal cells (normal human skin fibroblasts). This is reflected in a prolonged stoppage in G1 that induces apoptosis in cells lacking p53 (>50% of tumours) but is reversible in normal cells [A. Montagnoli et al., CANCER RESEARCH 64, 7110-7116, Oct. 1, 2004].

The inhibitors of Cdc7 kinase activity can constitute a novel category of targeted cytotoxic therapy as well as of inhibitors of DNA replication. Such inhibitors would inhibit replication before the replication forks are established, thus blocking replication without damaging the DNA. The present application thus relates in particular to novel inhibitors of protein kinase Cdc7 that can be used notably for the treatment of abnormal cellular proliferation and more particularly in oncology.

Methods of Treatment

The methods involve uses of a compound of Formula (A) or (B), or pharmaceutically acceptable salt or pharmaceutical composition thereof.

In one aspect, the present invention provides a compound of Formula (A) or (B), or a pharmaceutically acceptable salt thereof, for use in the treatment or prevention of a proliferative disorder.

In another aspect, the present invention provides use of a compound of Formula (A) or (B), or a pharmaceutically acceptable salt thereof, for the manufacture of a medicament for treating or preventing a proliferative disorder.

In yet another aspect, the present invention provides a method for treating or preventing a proliferative disorder in a subject in need thereof, wherein the subject is administered a therapeutically effective amount of a compound of the Formula (A) or (B), or a pharmaceutically acceptable salt thereof.

In certain embodiments, the subject is human.

In certain embodiments, the compound induces apoptosis. In certain embodiments, compound induces S-phase arrest.

In certain embodiments, the compound is an inhibitor of a protein kinase; and wherein the inhibition of a protein kinase is useful for the treatment or prevention of the proliferative disorder. In certain embodiments, the protein kinase is Cdc7 kinase or the Dbf4 regulatory subunit of Cdc7 kinase, and wherein the inhibition of Cdc7 kinase or the Dbf4 regulatory subunit of Cdc7 kinase is useful for the treatment or prevention of the proliferative disorder. In some embodiments, the protein kinase inhibitor is a Cdc7 kinase inhibitor or the Dbf4 regulatory subunit of Cdc7 kinase.

In certain embodiments, the proliferative disorder is selected from the group consisting of cancer, myeloproliferative disorders (e.g., polycythemia vera, essential thrombocytosis, meylofibrosis, and chronic myelogenous leukemia (CML)), benign prostate hyperplasia, familial adenomatosis, polyposis, neuro-fibromatosis, psoriasis, vascular smooth cell proliferation associated with atherosclerosis, fibrotic disorders, pulmonary fibrosis, arthritis, rheumatoid arthritis, glomerulonephritis, and post-surgical stenosis, restenosis, disorders of proliferation of blood vessels, disorders of proliferation of mesangial cells, metabolic disorders, allergies, asthmas, thromboses, diseases of the nervous system, retinopathy, diabetes, and muscular degeneration. In certain embodiments, the proliferative disorder is cancer.

In certain embodiments, the cancer is selected from the group consisting of cancer of the bone, brain, connective tissue, endocrine glands, adrenal cortex, endometrium, germ cells, head and neck, larynx and hypopharynx, mesothelioma, muscle, rectum, renal, small intestine, soft tissue, testis, ureter, vagina, and vulva; bladder cancer; breast cancer; colon cancer; kidney cancer; liver cancer; lung cancer; esophagus cancer; gallbladder cancer; ovarian cancer; pancreatic cancer; stomach cancer; cervical cancer; thyroid cancer; prostate cancer; papillary thyroid carcinoma; genitourinary malignancies; retinoblastoma; Wilms tumor; myelodysplastic syndrome; plasma cell neoplasia; paraneoplastic syndromes; renal cell carcinoma; Ewing's sarcoma; desmoplastic small round cell tumors; mesothelioma; skin cancer, wherein said skin cancer is squamous cell carcinoma; hematologic cancers [e.g., hematopoietic cancers of lymphoid lineage, wherein said cancers are leukemia, acute lymphocytic leukemia (ALL), acute lymphoblastic leukemia, lymphoma, B-cell lymphoma, T-cell lymphoma, Hodgkin's lymphoma, non-Hodgkin's lymphoma (e.g., mantle cell lymphoma (MCL), hairy cell lymphoma, and Burkitt's lymphoma; chronic lymphocytic leukemia (CLL); hematopoietic cancers of myeloid lineage, wherein said cancers are multiple myeloma, chronic myeloid leukemia (CML) and acute myeloid leukemia (AML) (e.g., acute megakaryoblastic leukemia (AMKL); myelodysplastic syndrome and promyelocytic leukemia]; tumors of mesenchymal origin, wherein the tumors are fibrosarcoma and rhabdomyosarcoma; tumors of the central and peripheral nervous system, wherein said tumors are astrocytoma, neuroblastoma, glioma (e.g., glioblastoma) and schwannomas; and other tumors, wherein said tumors are melanoma, cutaneous melanoma, seminoma, teratocarcinoma, osteosarcoma, xeroderma pegmentosum, keratoxanthoma, thyroid follicular cancer, Kaposi's sarcoma, cancers of unknown primary site; solid tumors, hematologic cancers, and AIDS-related malignancies.

In certain embodiments, the cancer is a multi-drug resistant (MDR) cancer.

In certain embodiments, the cancer is relapsed and/or refractory cancer. Relapsed cancer refers to a cancer which has returned after a patient has enjoyed a remission. Refractory cancer refers to a cancer which does not respond to other therapies or therapeutic agents. In certain embodiments, the cancer is resistant to (i.e., does not respond to) therapies or chemotherapeutic agents. In certain embodiments, the hematologic cancer is resistant to therapies or chemotherapeutic agents.

In certain embodiments, the cancer is leukemia, lymphoma, melanoma, cancer of the breast, stomach, ovaries, colon, rectum, lung, brain, larynx, lymphatic system, thyroid, oesophagus, liver, uterus, testis, bladder, prostate, bones or pancreas. In certain embodiments, the cancer is leukemia, cancer of the breast, the colon or the lung.

In certain embodiments, the cancer is a hematologic cancer. In certain embodiments, the compound inhibits the growth of hematologic cancers. In certain embodiments, the compound inhibits the growth of hematologic cancers with IC50s in the nanomolar range. In certain embodiments, the hematologic cancer is a hematopoietic cancer of lymphoid lineage. In certain embodiments, the hematologic cancer is a relapsed and/or refractory hematopoietic cancer of lymphoid lineage. In certain embodiments, the cancer is refractory to multiple cycles of cancer therapy (e.g., including allogenic bone marrow transplantation). In certain embodiments, the hematologic cancer is relapsed and/or refractory ALL, CLL, AML, or CML.

In certain embodiments, the cancer is ovarian cancer. In certain embodiments, the ovarian cancer is ovarian carcinoma.

In certain embodiments, the cancer is lung cancer. In certain embodiments, the lung cancer is non-small cell lung cancer. In certain embodiments, the lung cancer is small cell lung cancer. In certain embodiments, the lung cancer is lung adenocarcinoma.

In certain embodiments, the cancer is prostate cancer.

In certain embodiments, the cancer is renal cell carcinoma.

In certain embodiments, the cancer is cervical cancer. In certain embodiments, the cervical cancer is cervical adenocarcinoma. In certain embodiments, the cervical cancer is positive for human papillomavirus (HPV) infection.

In certain embodiments, the cancer is glioblastoma.

In certain embodiments, the cancer is retinoblastoma.

In certain embodiments, the cancer is rhabdomyosarcoma.

In certain embodiments, the cancer is a desmoplastic small round cell tumor.

In certain embodiments, the cancer is breast cancer. In certain embodiments, the breast cancer is breast ductal carcinoma. In certain embodiments, the breast cancer is breast adenocarcinoma. In certain embodiments, the breast cancer is metastatic breast adenocarcinoma. In certain embodiments, the breast cancer is HER2 negative. In certain embodiments, the breast cancer is HER2 positive. In certain embodiments, the breast cancer is NEU receptor negative.

In certain embodiments, the cancer is mesothelioma.

In certain embodiments, the cancer is melanoma.

In certain embodiments, the cancer is thyroid carcinoma.

In certain embodiments, the cancer is Ewing's sarcoma.

In certain embodiments, the cancer is a solid tumor. In certain embodiments, the compound inhibits the growth of solid tumors. In certain embodiments, the compound inhibits the growth of solid tumors with IC50s in the nanomolar range.

In certain embodiments, the cancer comprises a genetic mutation.

In certain embodiments, the cancer comprises a RAS mutation. In certain embodiments, the cancer comprises wild-type RAS.

In certain embodiments, cancer comprises an EGFR mutation. In certain embodiments, the EGFR mutation is an L858R EGFR mutation. In certain embodiments, the EGFR mutation is an DelE746 EGFR mutation. In certain embodiments, the EGFR mutation is an DelE746-A750 EGFR mutation. In certain embodiments, the EGFR mutation is an DelE746-E749 EGFR mutation. In certain embodiments, the EGFR mutation is an T790M EGFR mutation. In certain embodiments, the EGFR mutation is an T790ML858R EGFR mutation. In certain embodiments, the cancer comprises wild-type EGFR.

In certain embodiments, the cancer comprises a KRAS mutation. In certain embodiments, the cancer comprises a G13C KRAS mutation. In certain embodiments, the cancer comprises a G12C KRAS mutation. In certain embodiments, the cancer comprises a G12C KRAS mutation. In certain embodiments, the cancer comprises a Q61H KRAS mutation. In certain embodiments, the cancer comprises wild-type KRAS.

In certain embodiments, the cancer comprises a p53 mutation. In certain embodiments, the p53 mutation is a R273H p53 mutation. In certain embodiments, the p53 mutation is a G262V p53 mutation. In certain embodiments, the p53 mutation is a G16L p53 mutation. In certain embodiments, the p53 mutation is a C176F p53 mutation. In certain embodiments, the p53 mutation is a M246I p53 mutation. In certain embodiments, the cancer comprises wild-type p53.

In certain embodiments, the cancer comprises a BRAF mutation. In certain embodiments, the BRAF mutation is a BRAF V600E mutation.

In certain embodiments, the cancer comprises a EVI1 mutation.

In certain embodiments, the cancer comprises a Flt-3 mutation.

In certain embodiments, the cancer comprises a WT-1 mutation.

In certain embodiments, the cancer comprises a cyclin D mutation.

In certain embodiments, the cancer comprises a PTEN mutation.

In certain embodiments, the cancer comprises a ABL kinase mutation.

In certain embodiments, the mutation comprises a chromosomal abnormality. In certain embodiments, the chromosomal abnormality is a chromosome deletion or inversion. In certaine embodiments, the cancer comprises a chromosome 17p deletion. In certain embodiments, the cancer comprises an inversion of chromosome 16. In certain embodiments, the cancer comprises a trisomy of chromosome 8. In certain embodiments, the cancer comprises a monosomy of chromosome 7. In certain embodiments, the cancer comprises a chromosome 11q23 abnormality. In certain embodiments, the cancer comprises a Philadelphia chromosome positive abnormality.

In certain embodiments, the cancer comprises a fusion transcript. In certain embodiments, the fusion transcript is a reciprocal ASPL-TFE3 fusion transcript.

Assays

In some embodiments, the present invention provides a method of determining dose response using a cytotoxicity assay. In some embodiments, the present invention includes a method of performing dose response studies comprising the steps of providing a test compound, contacting the test compound with a cell, and incubating the cell with the compound under suitable conditions to determine the cytotoxicity of the compound. The antiproliferative activity of the test compound can then be assessed using a method known to those of ordinary skill in the art. This process can then be repeated using different concentrations of a test compound in order to calculate the $IC_{50}$. In certain embodiments, the test compound is an compound. In certain embodiments, the cells are retinoblastoma cells.

In certain embodiments, the cells are incubated with a test compound (e.g., an compound) for approximately 1 minute to approximately 1 week. In certain embodiments, the cells are incubated with a test compound for approximately 1 hour to approximately 1 week. In certain embodiments, the cells are incubated with a test compound for approximately 12 hours to approximately 1 week. In certain embodiments, the cells are incubated with a test compound for approximately 24 hours to approximately 1 week. In certain embodiments, the cells are incubated with a test compound for approximately 36 hours to approximately 1 week. In certain embodiments, the cells are incubated with a test compound for approximately 48 hours to approximately 1 week. In certain embodiments, the cells are incubated with a test compound for approximately 48 hours to approximately 120 hours. In certain embodiments, the cells are incubated with a test compound for approximately 48 hours to approximately 96 hours. In certain embodiments, the cells are incubated with a test compound for approximately 62 hours to approximately 82 hours. In certain embodiments, the cells are incubated with a test compound for approximately 72 hours. In certain embodiments, the cells are incubated with a test compound for approximately 1, 2, 3, 4, 5, 6, or 7 days.

In certain embodiments, after a specified amount of time (e.g., 72 hours) an indicator of cell viability (e.g., Alamar Blue) is added, and the mixture is incubated for an additional period of time. In some embodiments, this additional period of time ranges from approximately 1 hour to approximately 48 hours. In some embodiments, this additional period of time ranges from approximately 12 hour to approximately 36 hours. In some embodiments, this additional period of time is approximately 24 hours.

The inhibition of cell proliferation may be measured using methods or technology known in the art. In some embodiments, inhibition of cell proliferation is measured using a substance which produces a detectable signal that is proportional to the amount of inhibition of cell proliferation. In some embodiments, inhibition of cell proliferation is quantified using one of any indicators known to those of ordinary skill in the art that produces a quantifiable signal, the intensity of which is detectable and proportional to the amount of inhibition. In some embodiments, inhibition of cell proliferation is quantified using an indicator which fluoresces. Exemplary indicators include Tyramide-Alexa Fluor 488, Alamar Blue, etc.

In some embodiments, the efficacy of a compound is measured by measuring tumor size over a period of time before, during, and/or after treatment with said compound. In some embodiments, tumor size is measured once a week. In some embodiments, tumor size is measured twice a week. In some embodiments, tumor size is measured daily. In some embodiments, tumor size is measured once a day. In some embodiments, tumor size is measured twice a day. In some embodiments, tumor size is measured once every other day. In some embodiments, tumor size is measured once every three days. In certain embodiments, tumor size is measured at intervals as required by any one of the methods known to those of skill in the art. In some embodiments, tumor size is measured externally twice a week with a caliper. In certain embodiments, tumor size is measured once a week using an imaging technique (e.g., MRI, X-ray, CT). In some embodiments, the imaging technique is bioluminescent imaging. In certain embodiments, bioluminescent imaging comprises anesthetization of the host animal, injection of a bioluminescent compound, and subsequent measurement of photonic emission. In some embodiments, imaging of the tumor is achieved using any of the methods known in the medical arts.

As detailed herein, in assays to determine the ability of a compound (e.g., an compound) to inhibit cancer cell growth certain compounds may exhibit $IC_{50}$ values ≤100 µM. In certain other embodiments, the compound exhibits $IC_{50}$ values ≤50 µM. In certain other embodiments, the compound exhibits $IC_{50}$ values ≤40 µM. In certain other embodiments, the compound exhibits $IC_{50}$ values ≤30 µM. In certain other embodiments, the compound exhibits $IC_{50}$ values ≤20 µM. In certain other embodiments, the compound exhibits $IC_{50}$ values ≤10 µM. In certain other embodiments, the compound exhibits $IC_{50}$ values ≤7.5 µM. In certain embodiments, the compound exhibits $IC_{50}$ values ≤5 µM. In certain other embodiments, the compound exhibits $IC_{50}$ values ≤2.5 µM. In certain embodiments, the compound exhibits $IC_{50}$ values ≤1 µM. In certain embodiments, the compound exhibits $IC_{50}$ values ≤0.75 µM. In certain embodiments, the compound exhibits $IC_{50}$ values ≤0.5 µM. In certain embodiments, the compound exhibits $IC_{50}$ values ≤0.25 µM. In certain embodiments, the compound exhibits $IC_{50}$ values ≤0.1 µM. In certain other embodiments, the compound exhibits $IC_{50}$ values ≤75 nM. In certain other embodiments, the compound exhibits $IC_{50}$ values ≤50 nM. In certain other embodiments, the compound exhibits $IC_{50}$ values ≤25 nM. In certain other embodiments, the compound exhibits $IC_{50}$ values ≤10 nM. In other embodiments, the compound exhibits $IC_{50}$ values ≤7.5 nM. In other embodiments, the compound exhibits $IC_{50}$ values ≤5 nM.

Pharmaceutical Compositions

Certain aspects of the invention include use of a pharmaceutical composition in any of the above methods, comprising a compound of Formula (A) or (B) or a pharmaceutically acceptable salt thereof and a pharmaceutically acceptable excipient.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the active ingredient into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation suitable for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* $21^{st}$ ed., Lippincott Williams & Wilkins, 2005.

Provided compounds can be administered using any amount and any route of administration effective for treatment. The exact amount required will vary from subject to subject, depending on the species, age, and general condition of the subject, the severity of the infection, the particular composition, its mode of administration, its mode of activity, and the like.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site, in a bolus or continuous infusion regimen. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of a compound required to achieve a therapeutically effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, a therapeutically effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, about 0.001 mg to about 100 mg, from about 0.01 mg to about 50 mg, from about 0.1 mg to about 40 mg, from about 0.5 mg to about 30 mg, from about 0.01 mg to about 10 mg, from about 0.1 mg to about 10 mg, and from about 1 mg to about 25 mg, per kilogram, of a compound. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

The method comprises administration of a compound in a therapeutically effective dose to a host subject. In some embodiments, the subject is an animal. In some embodiments, a therapeutically effective dose comprises an amount ranging from approximately 0.1 mg/kg to approximately 50.0 mg/kg. In some embodiments, a therapeutically effective dose comprises an amount ranging from approximately 0.5 mg/kg to approximately 50.0 mg/kg. In some embodiments, a therapeutically effective dose comprises an amount ranging from approximately 0.5 mg/kg to approximately 40.0 mg/kg. In some embodiments, a therapeutically effective dose comprises an amount ranging from approximately 0.5 mg/kg to approximately 30.0 mg/kg. In some embodiments, a therapeutically effective dose comprises an amount ranging from approximately 1.0 mg/kg to approximately 25.0 mg/kg. In some embodiments, a therapeutically effective dose comprises an amount ranging from approximately 1.5 mg/kg to approximately 15.0 mg/kg. In some embodiments, treatment is administered locally. In some embodiments, treatment is administered by continuous infusion over a certain period of time. In certain embodiments, administration is via intraarterial infusion. In certain embodiments, administration is via intraarterial infusion via an artery feeding the tumor being treated.

Some embodiments of the invention further comprise the administration of at least one other therapy or therapeutic agents. The compound or composition can be administered concurrently with, prior to, or subsequent to, the other therapy or therapeutic agents. In general, each therapy or agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the compound with the therapy or therapeutic agent and/or the desired therapeutic effect to be achieved. In general, it is expected that additional therapy or therapeutic agent utilized in combination be utilized at levels that do not exceed the levels at which they are utilized individually. In some embodiments, the levels utilized in combination will be lower than those utilized individually.

The compounds or compositions can be administered in combination with a therapy or therapeutic agent that improves their bioavailability, reduce and/or modify their metabolism, inhibit their excretion, and/or modify their distribution within the body. It will also be appreciated that the therapy or therapeutic agent employed may achieve a desired effect for the same disease or disorder, and/or it may achieve different effects (e.g., control of adverse side-effects).

Cancer therapies include, but are not limited to, surgery and surgical treatments, radiation therapy, and therapeutic agents (e.g., biotherapeutic agents and chemotherapeutic agents). In certain embodiments, the method comprises administration of radiation.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), antimetabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN@), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

Kits

In still another aspect, the present invention also provides kits (e.g., pharmaceutical packs) for treating a proliferative disorder comprising a compound of the Formula (A) or (B) and instructions for administration to a subject for treating a proliferative disorder. Kits may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

EXAMPLES

In order that the invention described herein may be more fully understood, the following examples are set forth. It should be understood that these examples are for illustrative purposes only and are not to be construed as limiting this invention in any manner.

Example 1. Inhibition of Primary Patient Samples

Table 1 highlights a series of primary patient leukemia samples-both acute and chronic and treatment naïve and refractory and the effect of granaticin A, granaticin B, derivative 1, and derivative 2 to inhibit cellular proliferation. The $IC_{50}$ data reveals that granaticin B is approximately one log more active than granaticin A against all the samples tested and inhibits cellular proliferation in the low nanomolar range. The two starred samples represent serial samples taken from the same patients after they received 2-3 cycles of additional high dose salvage chemotherapy and indicate that although refractory to salvage chemotherapy, the Cdc7 pathway remains a potentially efficacious target as the sensitivity to these compounds remains unchanged. Importantly, each patient sample was resistant to the prior therapy received using this assay.

TABLE 1

Inhibition of patient leukemia samples

| Leukemia sample | $IC_{50}$ (microM) | | | |
|---|---|---|---|---|
| | Granaticin A | Deriv. 1 | Deriv. 2 | Granaticin B |
| AML, de novo | 0.72 | 0.62 | 2.01 | 0.18 |
| AML, primary refractory 1 | 0.75 | 0.62 | 1.55 | 0.11 |
| AML, primary refractory 1* | 0.63 | 0.47 | 1.44 | 0.10 |
| AML, primary refractory | 0.77 | 0.84 | 1.45 | 0.14 |
| AML, relapsed | 1.20 | 0.70 | 2.23 | 0.10 |
| AML, relapsed | 0.21 | 0.23 | 0.35 | 0.05 |
| AML, relapsed s/p HSCT | 1.88 | 1.86 | 8.10 | 0.62 |
| AMMoL | 0.99 | 0.79 | 5.88 | 0.49 |
| ALL, Ph+ | 0.56 | 0.47 | 2.57 | 0.19 |
| Biphenotypic acute leukemia 1 | 0.30 | 0.69 | 0.90 | 0.04 |
| Biphenotypic acute leukemia 1* | 0.54 | 0.76 | 1.02 | 0.10 |
| CML, untreated | 0.26 | 0.33 | 1.24 | 0.08 |
| CLL, untreated, chromosome 17p del. | 0.46 | 0.36 | 1.21 | 0.31 |
| PhALL3.1 | 0.14 | 0.12 | 0.47 | 0.03 |

Figure 16A:
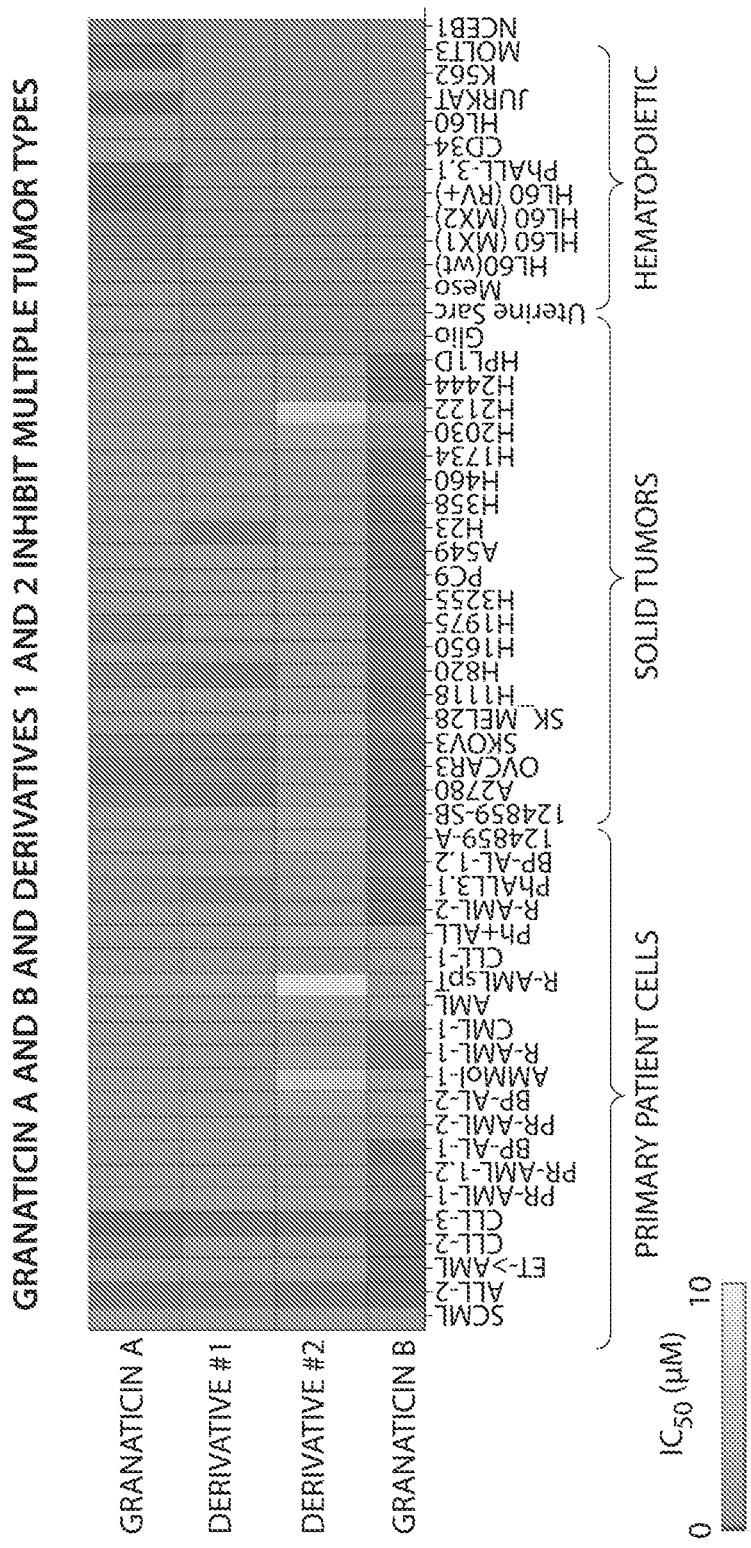
FIGS. 16A-16B. Granaticin A and Granaticin B inhibit multiple tumor types: The indicated cell lines and primary patient samples were tested against the compounds listed in standard cytotoxicity assays (12 point dose response using Alamar blue reduction as an indicator of cell viability). Assays were done in triplicate and IC50 determinations were run in 12-point serial dilutions from 10 mM to 5 nM. IC50 values are displayed with darker shades indicating low nanomolar values and lighter shades high micromolar values, respectively.
Figure 16B:
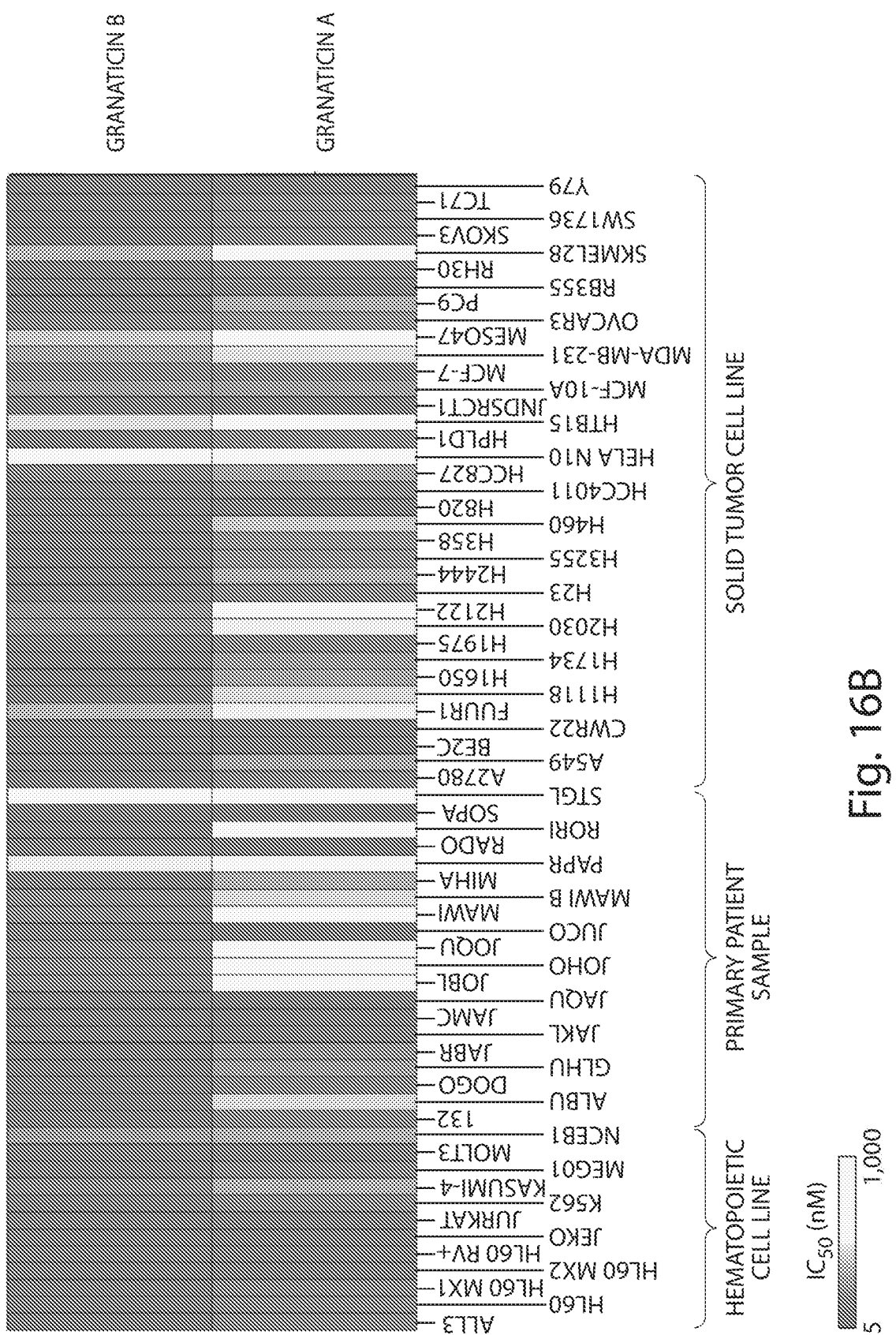
Figure 17:
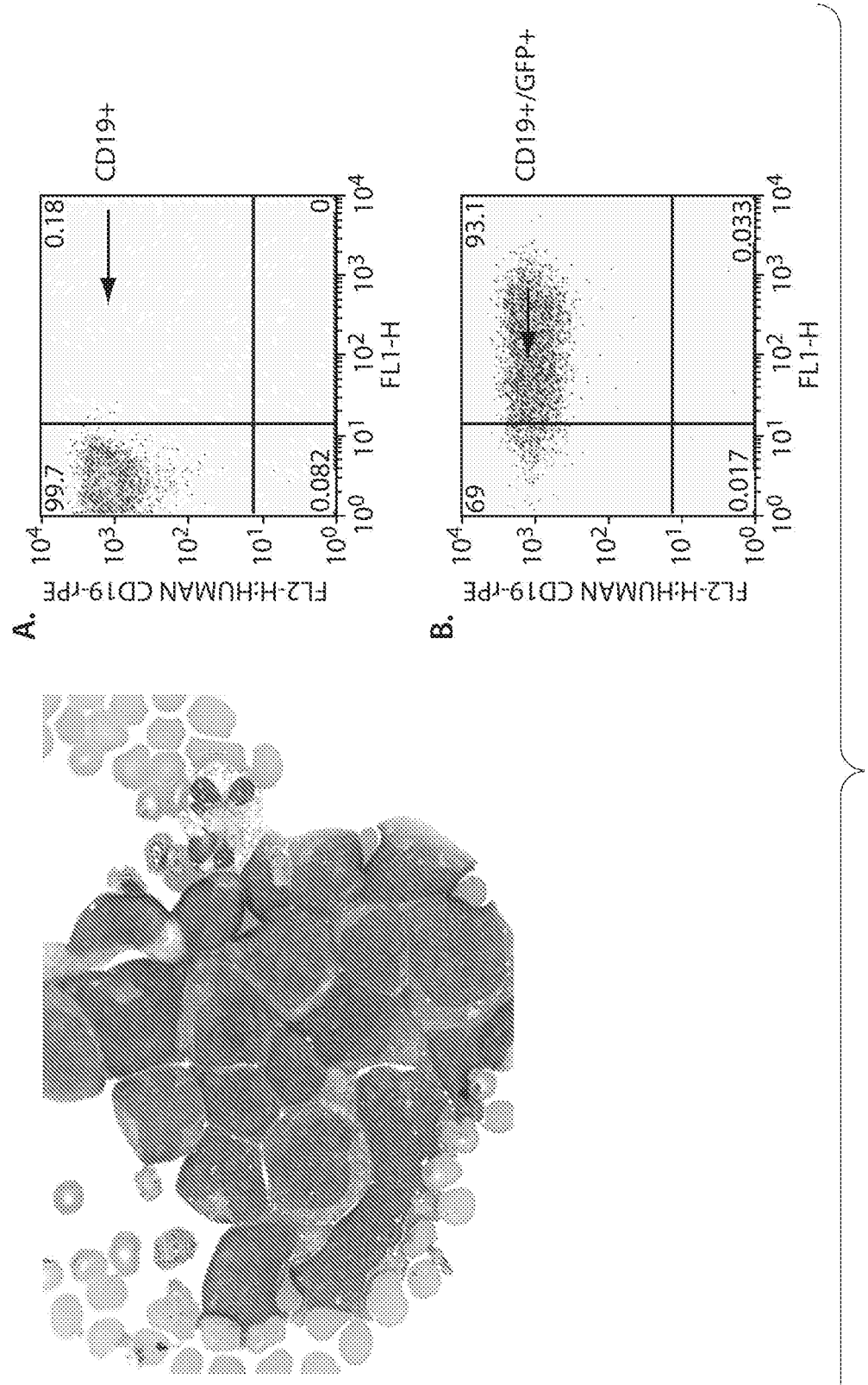
FIG. 17. t(9:22)(q34;q11) Acute Lymphocytic Leukemia cell line: Based on the results of the cytotoxicity assays, granaticin A and granaticin B were chosen to pursue studies in mice using the Ph-ALL3.1 mouse model. The PhALL3.1 cell line was retrovirally transduced with a GFP-firefly luciferase expressing construct using standard techniques. The infected cells were sorted by FACS for CD19 and GFP co-expression. Panel A is the FACS profile of the cells before transduction and Panel B is the FACS profile of the cells after transduction demonstrating CD19-GFP double positive cells which were then used to inject immunocompromised SCID-Beige mice. Ph+ ALL cells were isolated from the pleural fluid of a patient treated on the Leukemia Service, and used to create a cell line that grows readily in culture. The cytogenetics were confirmed by karyotype, FISH, RT-PCR, and Western blot analysis for p190 bcr-abl. The cell line was then transduced with a retrovirus GFP-firefly luciferase construct. Granaticin A has been shown to be very active against this cell line in the cell based assays.
Figure 18A:
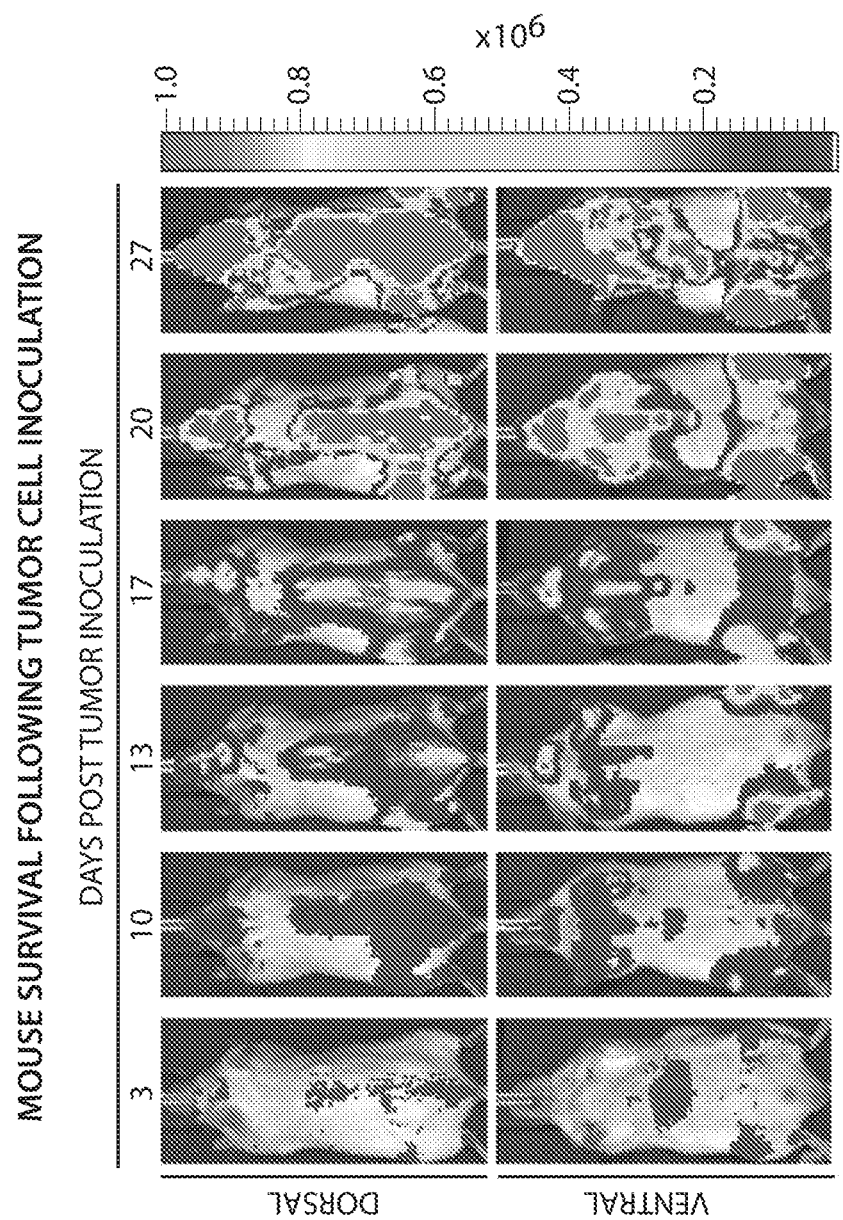
FIGS. 18A-18B. Mouse survival following tumor cell inoculation: 5 million PhALL3.1 tumor cells were injected into the tail veins of a cohort of eight SCID-Beige immunocompromised mice and disease progression was monitored on the indicated days using in vivo bioluminescence imaging.
Figure 18B:
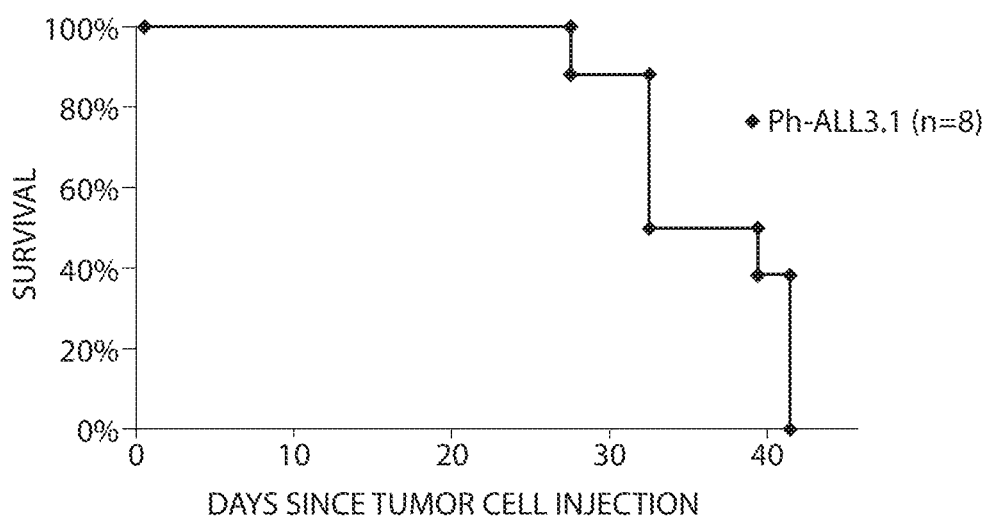
Figure 19B:
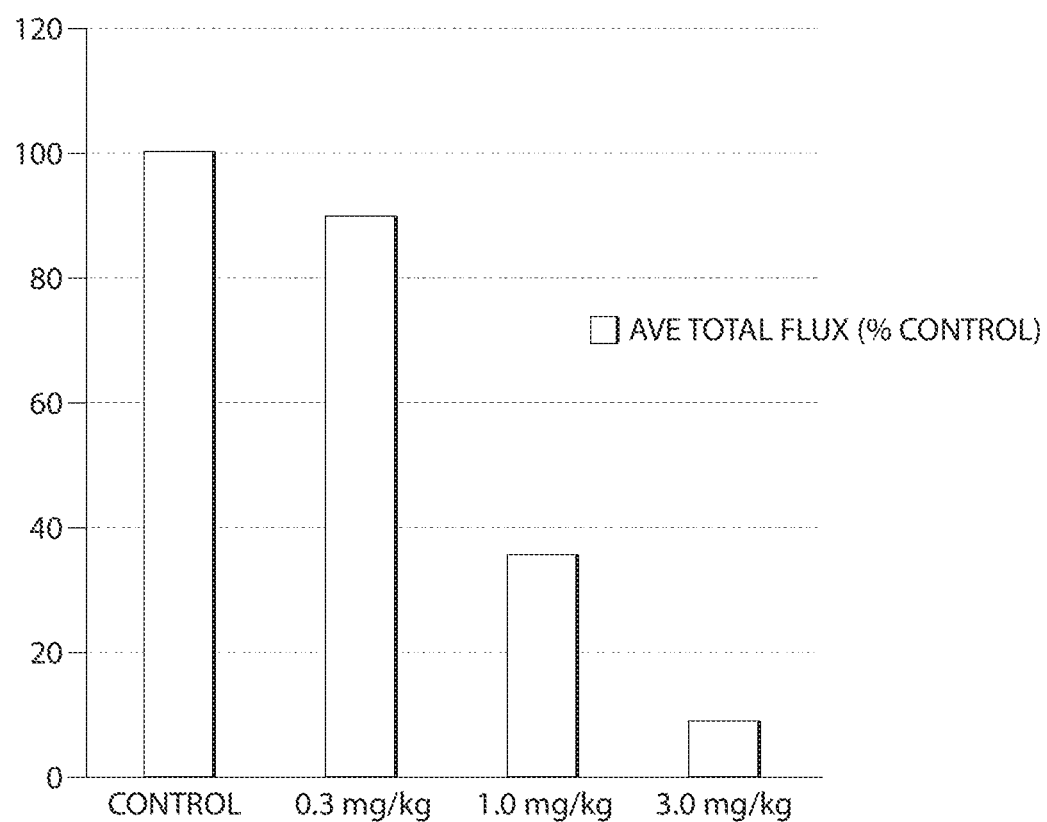
Figure 20A:
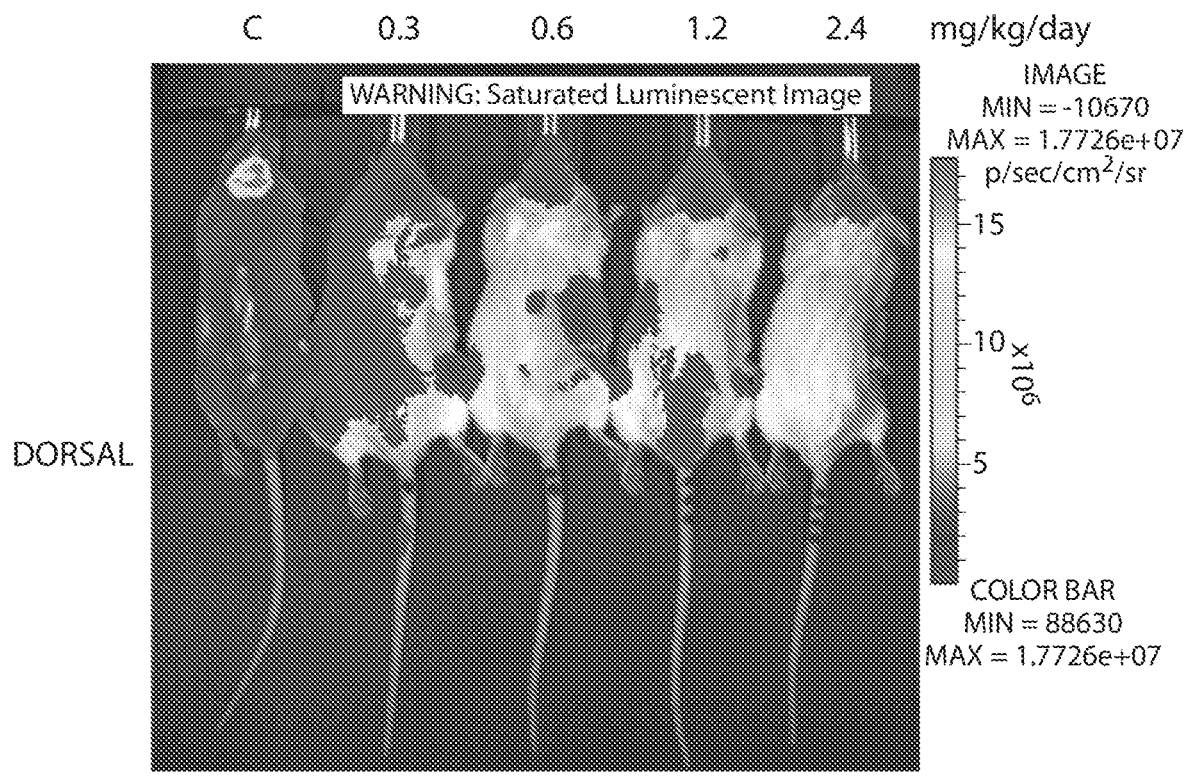
FIGS. 20A-20C. Granaticin B Inhibits Ph-ALL3.1 growth in vivo: Given the rapid intravenous clearance of granaticin A by the liver, granaticin B was used in a continuous infusion experiment with the PhALL3.1 animal model. Diffusion pumps containing granaticin B were surgically implanted in the flanks of 5 cohorts of mice on day +3 after injection of 5 million cells via the tail veins, and the drug (or control—C-DMSO) at the indicated concentration was allowed to diffuse for seven days before pump removal. The mice were imaged on day 12 (FIGS. 20A-20B) and tumor volume remaining was calculated (FIG. 20C). 95% tumor reduction was seen at the highest dose. The mice tolerated the procedure without obvious organ toxicity as seen on necropsy and indicate that granaticin B is stable enough when given intravenously to achieve efficacy against this lethal tumor model.
Figure 20B:
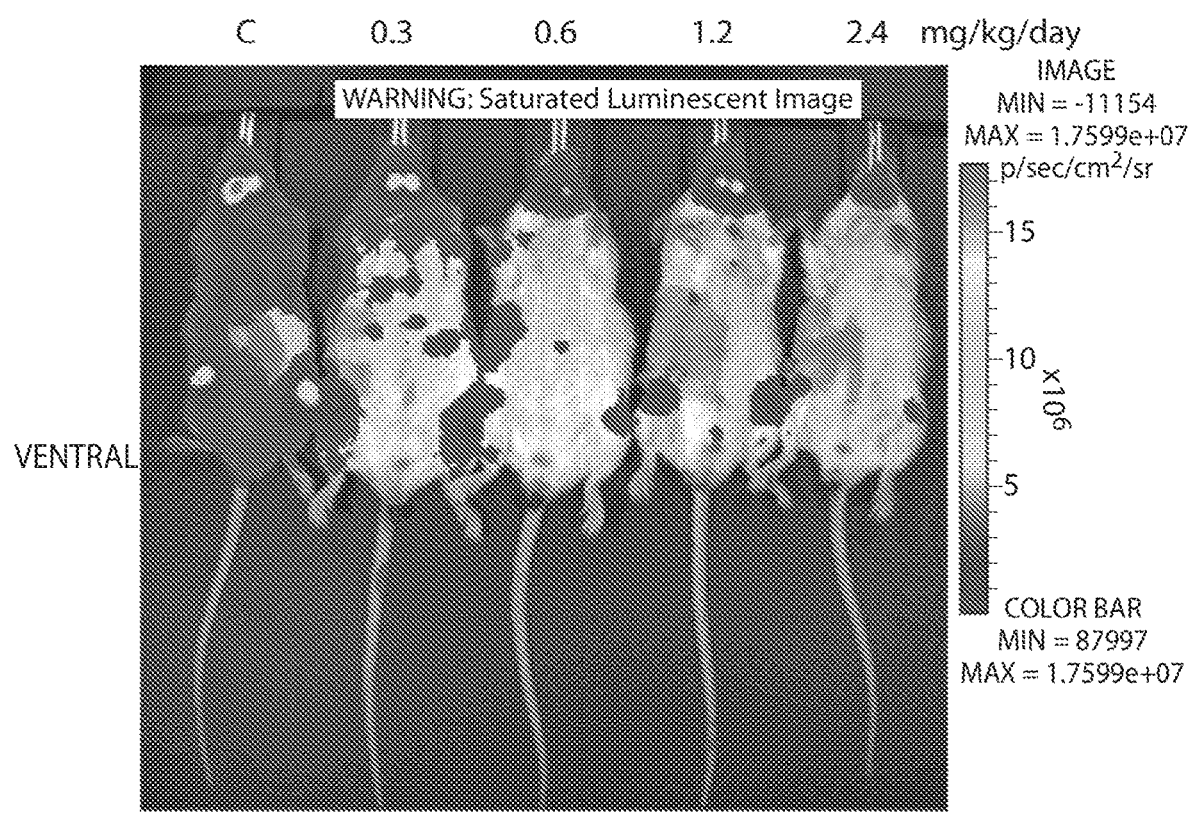
Figure 20C:
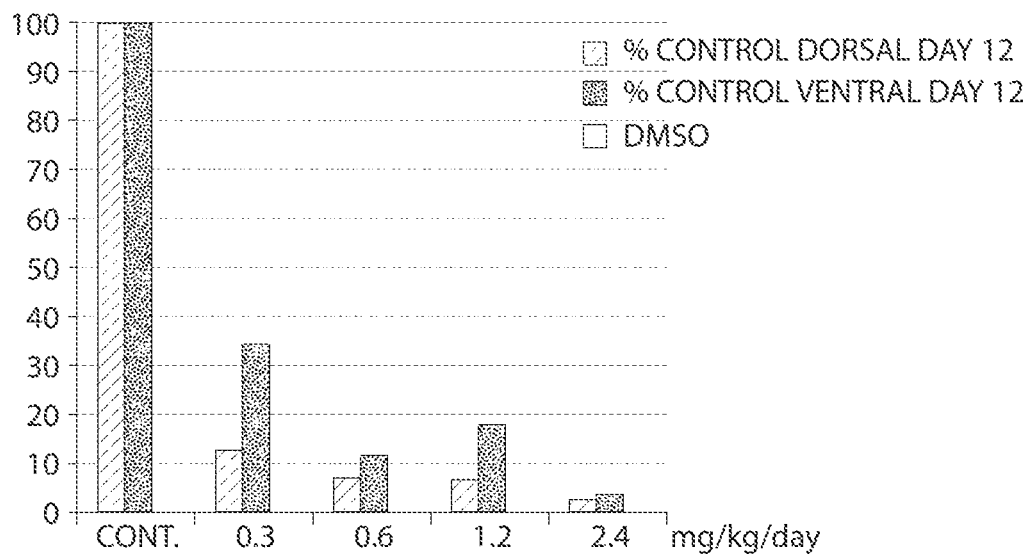
Figure 21:
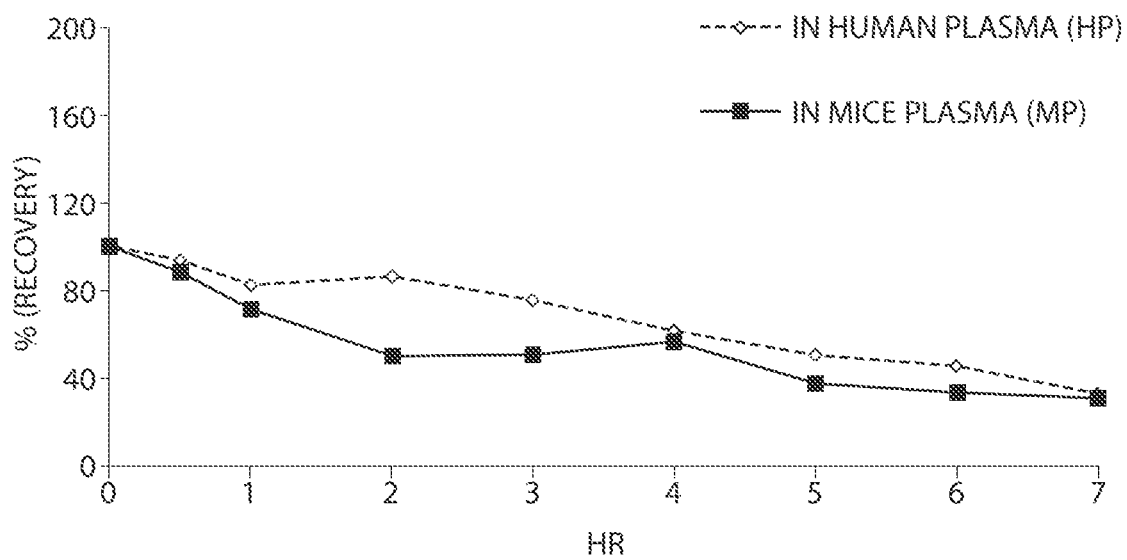
FIG. 21. Granaticin B stability study comparison in HP/MP: Standard plasma stability studies were conducted with Granaticin B. The recovery of Granaticin B was measured by mass spectrometry.
Figure 22A:
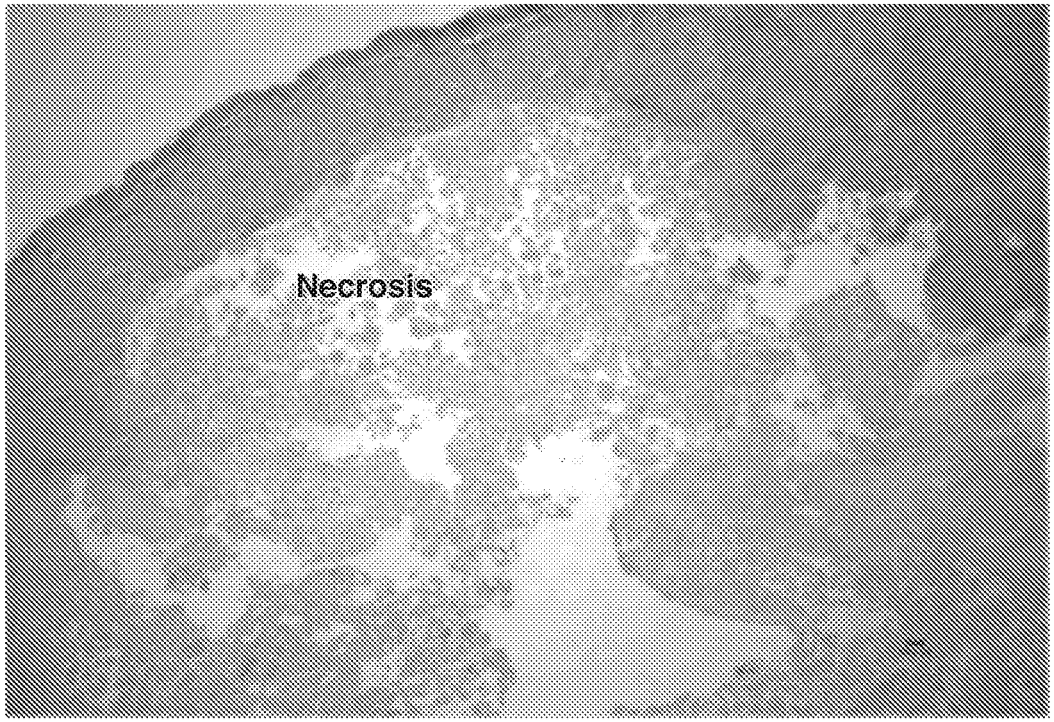
FIG. 22A-22C. Granaticin B is Effective Against Multiple Solid Tumors: granaticin B is efficacious against mouse models of melanoma (FIG. 22A), non-small cell lung cancer (FIG. 22B), and ovarian cancer (FIG. 22C). For the ovarian cancer experiments, SCID-Beige mice were injected with 5 million OVCAR3 cells that had been transduced with a GFP-firefly luciferase expressing plasmid (Frattini, M. G. and Brentjens, R. J., unpublished data). These cells were then injected intraperitoneally into 4 cohorts of mice on Day 1. From days 7-14 the mice were injected daily with the indicated concentrations of granaticin B in the intraperitoneal space. Imaging (luciferase activity) was acquired on day 42 and revealed essentially no disease in the mice treated at 3 mg/kg granaticin B. For the melanoma and non small-cell lung cancer models, SKMEL-28 and A459 cells, respectively were used in standard nude mouse xenograft experiments. Nude mice were treated with 2.5 mg/kg/day granaticin B in a continuous fashion using osmotic diffusion pumps. Sections of the treated xenografts are shown after euthanasia at day 28 and H&E staining. Control sections revealed no evidence of necrosis or cell death (not shown).
Figure 22B:
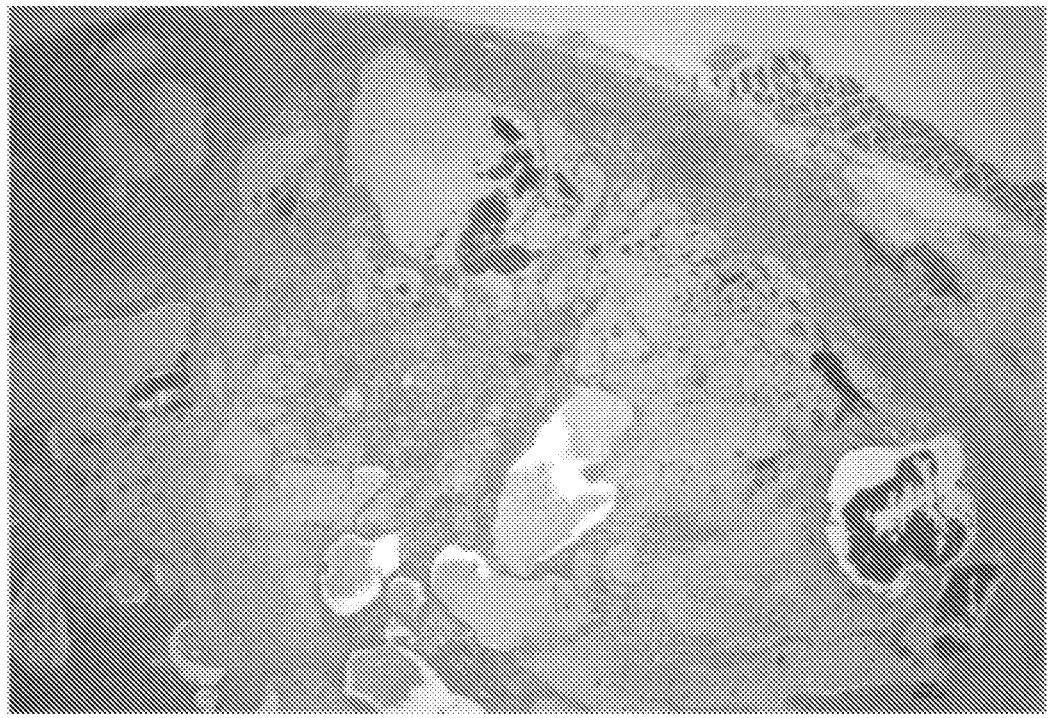
Figure 22C:
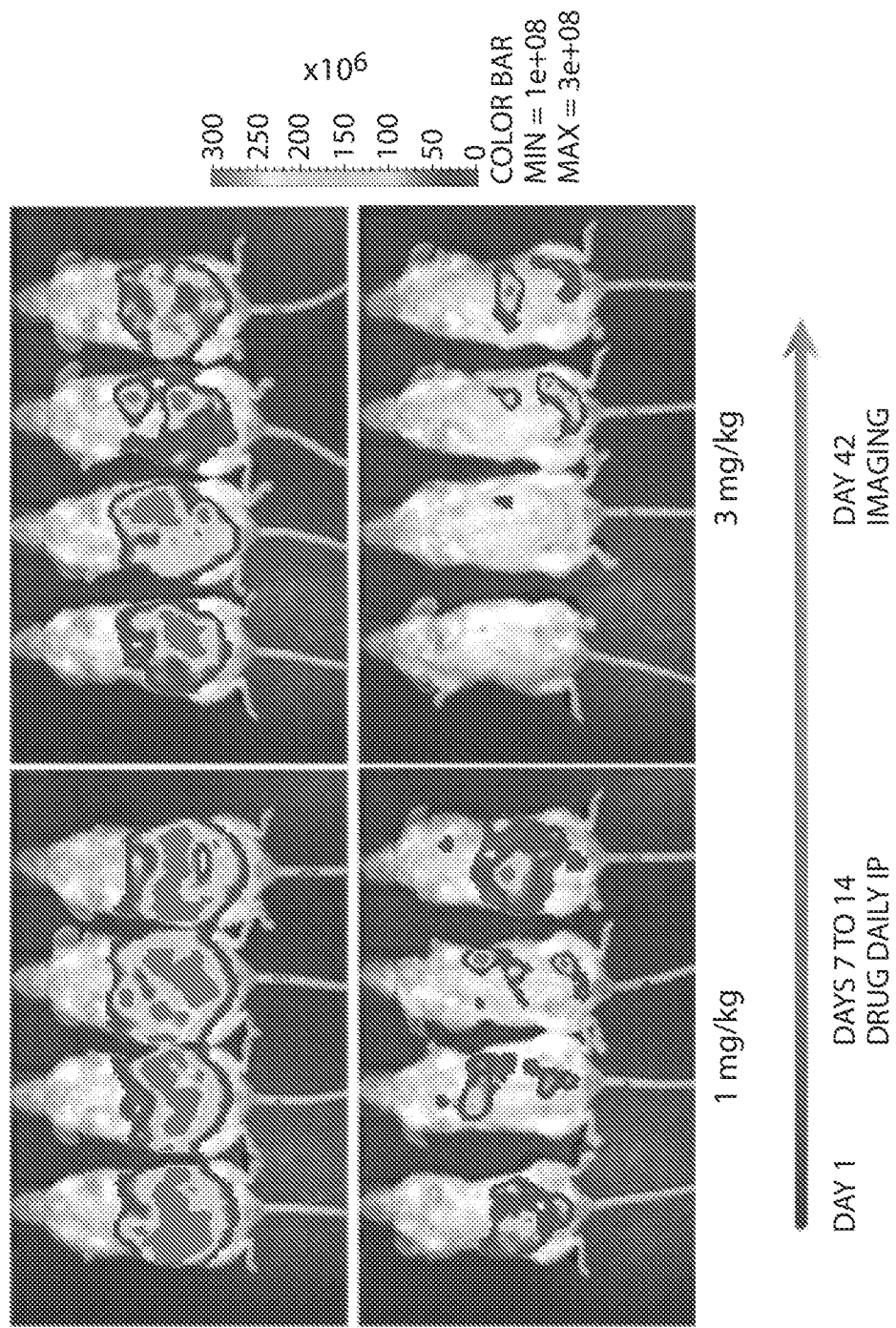
Figure 23B:
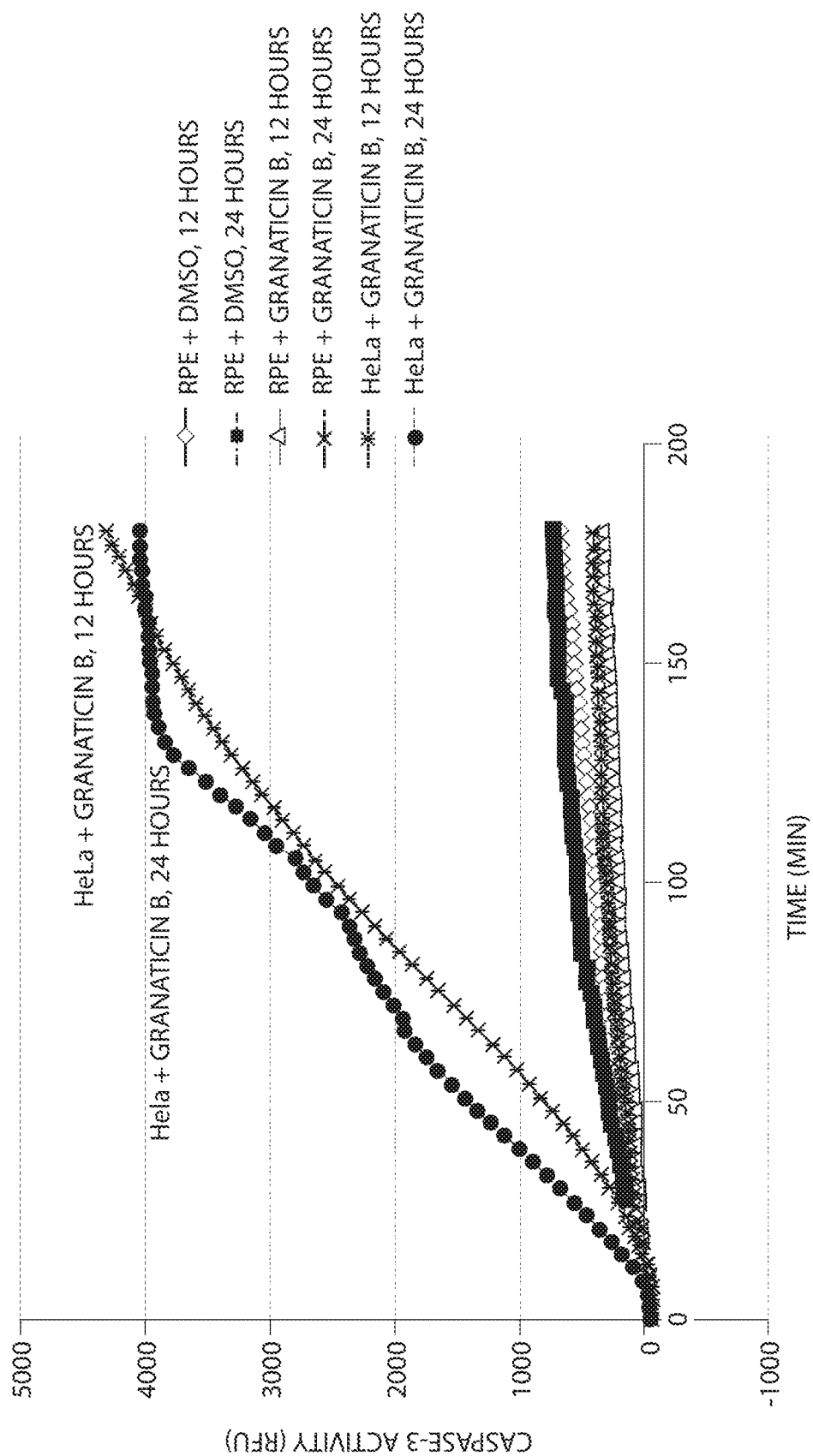
Figure 24A:
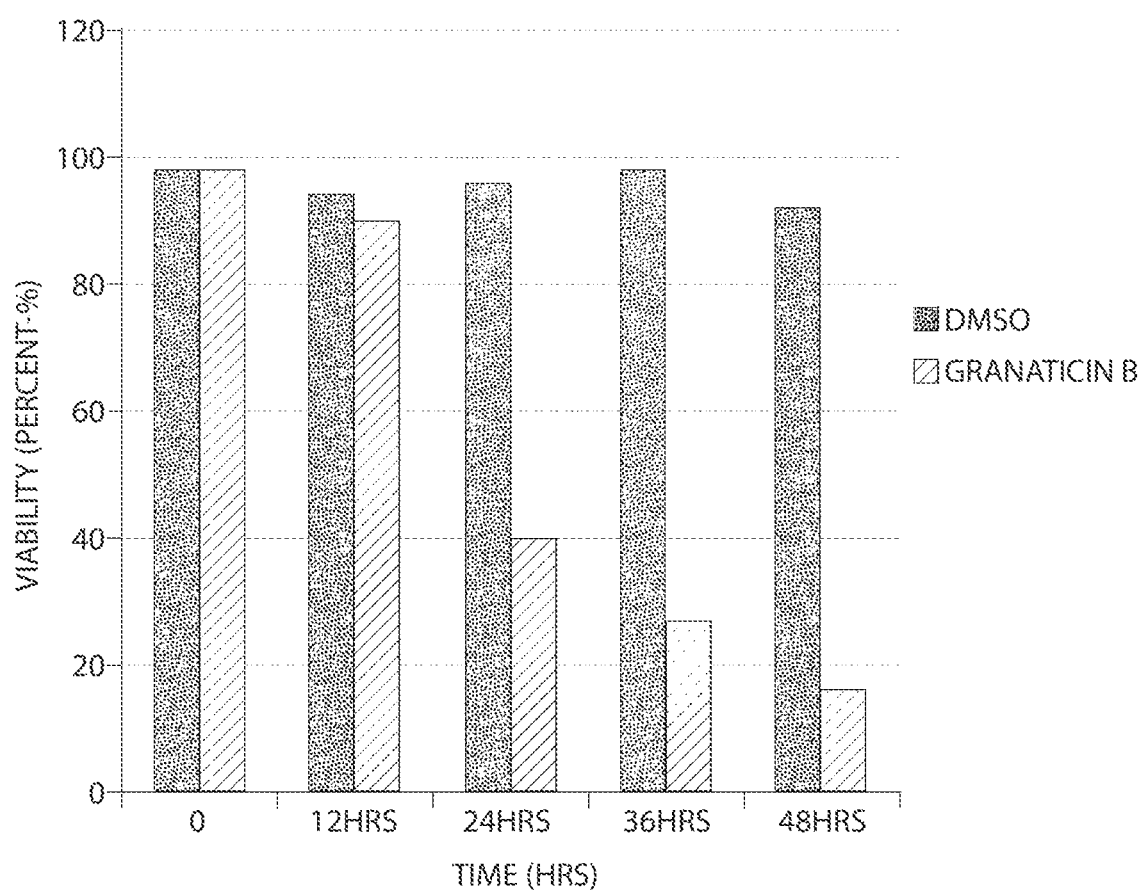
FIGS. 24A-24B. Granaticin B is very effective against JOKE-2 cells. The JOKE-2 cell line was derived from a patient with Philadelphia chromosome positive Acute Lymphoblastic Leukemia (Ph-ALL). The patient was clinically resistant to imatinib mesylate and the Bcr-Abl kinase was found to have the following high-risk resistance mutations in the Abl kinase domain (F317L, F359V, T315I, and E255K).
Figure 24B:
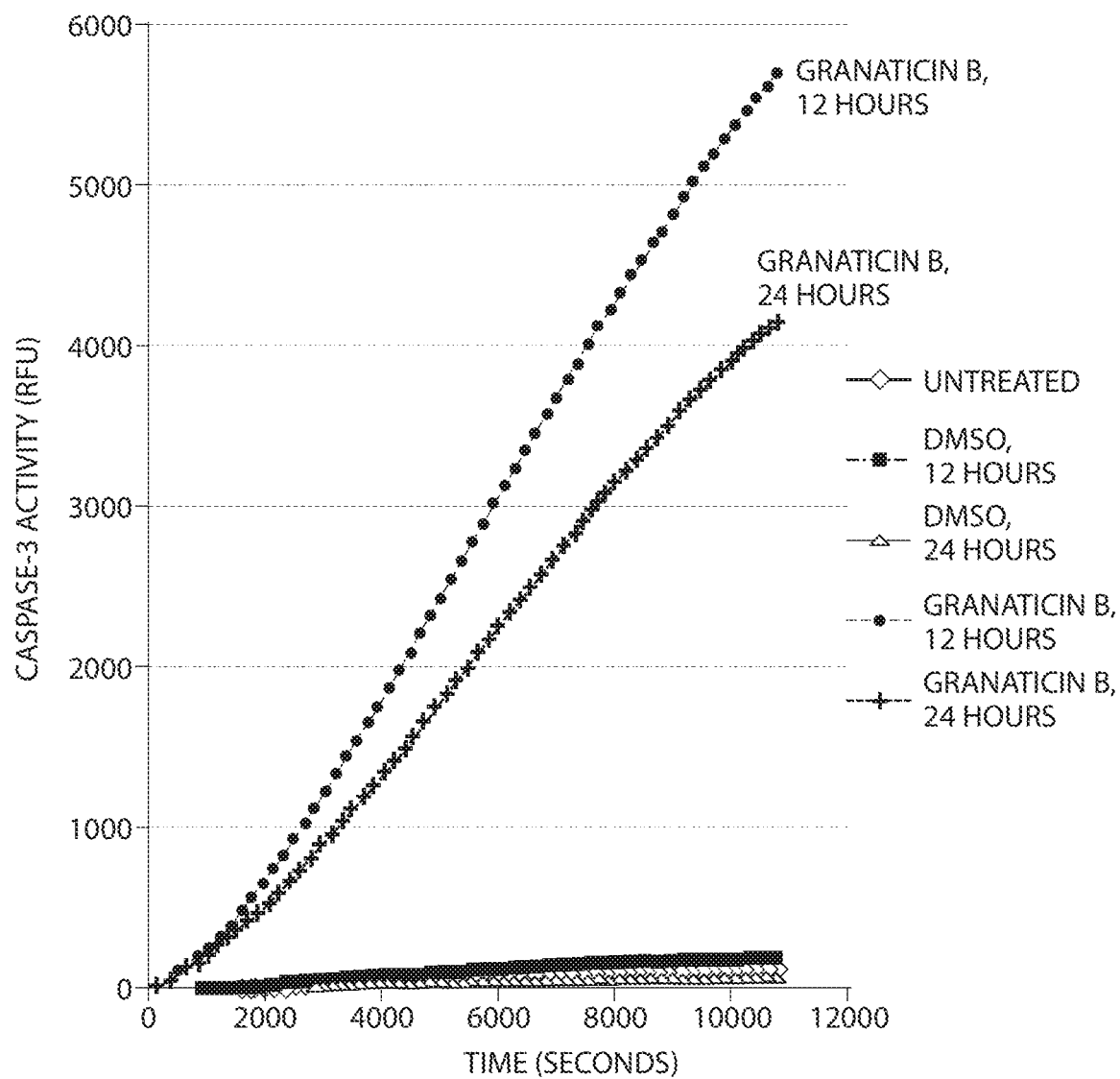

*Indicates a second sample from the same patient following high-dose chemotherapy Table 2 highlights cell lines and primary patient samples tested for granaticin A and granaticin B to inhibit cellular proliferation (summarized from FIGS. 16A and 16B).

TABLE 2

| Cell Line | Description | $IC_{50}$ (microM) | |
|---|---|---|---|
| | | Granaticin A | Granaticin B |
| ALL3 | Hematopoietic-Human Acute Lymphoblastic leukemia; Philadelphia chromosome positive | 0.14 | 0.03 |
| HL60 | Hematopoietic-Human Acute Promyelocytic leukemia | 0.14 | 0.09 |
| HL60 MX1 | Hematopoietic-Human Acute Promyelocytic leukemia; MDR variant of HL60 selected with mitoxantrone-clone 1 | 0.17 | 0.08 |
| HL60 MX2 | Hematopoietic-Human Acute Promyelocytic leukemia; MDR variant of HL60 selected with mitoxantrone-clone 2 | 0.11 | 0.07 |
| HL60 RV | Hematopoietic-Human Acute Promyelocytic leukemia: MDR variant of HL60 selected with vincristine | 0.09 | 0.07 |
| JEKO | Hematopoietic-Human Mantle Cell Lymphoma | 0.04 | 0.02 |
| JURKAT E61 | Hematopoietic-Human Acute Lymphoblastic T-cell leukemia | 0.05 | 0.02 |

TABLE 2-continued

| Cell Line | Description | $IC_{50}$ (microM) | |
|---|---|---|---|
| | | Granaticin A | Granaticin B |
| K562 | Hematopoietic-Human Chronic Myelogenous leukemia transformed to acute erythroleukemia | 0.12 | 0.08 |
| KASUMI4 | Hematopoietic-Human Chronic Myelogenous leukemia transformed to acute myeloid leukemia-overexpression of EVI1 | 0.30 | 0.18 |
| MEG01 | Hematopoietic-Human Chronic Myelogenous leukemia transformed to acute Megakaryoblastic leukemia | 0.17 | 0.08 |
| MOLT3 | Hematopoietic-Human Acute Lympholastic T-cell Leukemia | 0.03 | 0.01 |
| NCEB1 | Hematopoietic-Human Mantle Cell Lymphoma | 0.33 | 0.26 |
| 132 | Primary-Patient sample of Chronic Lymphocytic Leukemia | 0.13 | 0.01 |
| ALBU | Primary-Patient sample of essential thrombocythemia transformed to refractory acute myelogenous leukemia | 0.43 | 0.03 |
| DOGO | Primary-Patient sample of Chronic Lymphocytic Leukemia with trisomy of chromosome 12 and unmutated Ig heavy chain locus | 0.15 | 0.07 |
| GLHU | Primary-Patient sample of Chronic Myelogenous leukemia | 0.26 | 0.08 |
| JABR | Primary-Patient sample of relpased/refractory acute myelogenous leukemia with normal cytogenetics and Flt-3 ITD | 0.21 | 0.05 |
| JAKL | Primary-Patient sample of Chronic Lymphocytic Leukemia with trisomy of chromosome 12 and unmutated Ig heavy chain locus | 0.05 | 0.01 |
| JAMC | Primary-Patient sample of acute myelogenous leukemia with inversion of chromosome 16 | 0.06 | 0.04 |
| JAQU | Primary-Patient sample of relapsed/refractory pre-B cell acute lymphoblastic leukemia | 0.05 | 0.01 |
| JOBL | Primary-Patient sample of relapsed/refractory acute myelogenous leukemia | 0.56 | 0.19 |
| JOHO | Primary-Patient sample of primary refractory acute myelogenous leukemia with inv3 and monosomy 7 (refractory to allogeneic BMT) | 0.88 | 0.17 |
| JOQU | Primary-Patient sample of relapsed/refractory acute myelogenous leukemia with trisomy of chromosome #8 and Flt-3 ITD | 0.77 | 0.14 |

TABLE 2-continued

| Cell Line | Description | IC$_{50}$ (microM) | |
|---|---|---|---|
| | | Granaticin A | Granaticin B |
| JUCO | Primary-Patient sample of pre-B cell acute lymphoblastic leukemia with t(4;11) involving the MLL gene | 0.08 | 0.01 |
| MAWI | Primary-Patient sample of relpased/refractory acute myelogenous leukemia with normal cytogenetics | 0.72 | 0.18 |
| MAWI B | Primary-Patient sample of secondary chronic myelogenous leukemia | 0.42 | 0.16 |
| MIHA | Primary-Patient sample of relapsed/refractory acute biphenotypic leukemia (patient was refractory to allogeneic bone marrow transplant) | 0.30 | 0.04 |
| PAPR | Primary-Patient sample of relapsed acute myelomonocytic leukemia | 0.99 | 0.49 |
| RADO | Primary-Patient sample of primary refractory acute myelogenous leukemia with multiple chromosomal abnormalities (−5,−7) | 0.06 | 0.03 |
| RORI | Primary-Patient sample of relapsed/refractory acute myelogenous leukemia with trisomy of chromosome #8 | 1.20 | 0.10 |
| SOPA | Primary-Patient sample of secondary acute myelogenous leukemia with chromsome 11q23 abnormality | 0.10 | 0.09 |
| STGL | Primary-Patient sample of refractory acute myelogenous leukemia with multiple chromosomal abnormalities(refractory to allogeneic BMT) | 1.88 | 0.62 |
| A2780 | Solid-Human ovarian carcinoma | 0.12 | 0.02 |
| A549 | Solid-Human lung adenocarcinoma; G12S KRAS mutation | 0.28 | 0.09 |
| BE(2)C | Solid-human neuroblastoma; p53 mutant | 0.07 | 0.04 |
| CWR22 | Solid-human prostate carcinoma | 0.09 | 0.04 |
| FUUR1 | Solid-human renal cell carcinoma with the reciprocal ASPL-TFE3 fusion transcript | 0.48 | 0.34 |
| H11-18 | Solid-Human lung adenocarcinoma; L858R EGFR mutation | 0.42 | 0.06 |
| H1650 | Solid- Human lung adenocarcinoma; DelE746-A750 EGFR mutation; wild-type RAS; PTEN null | 0.29 | 0.06 |
| H1734 | Solid-Human lung adenocarcinoma; G13C KRAS mutation | 0.24 | 0.04 |
| H1975 | Solid-Human lung adenocarcinoma; T790M/L858R EGFR mutation; R273H p53 mutation; PTEN null; wild-type KRAS | 0.12 | 0.03 |
| H2030 | Solid-human lung adenocarcinoma; wild-type EGFR; G12C KRAS mutation; G262V P53 mutation; PTEN null | 0.49 | 0.22 |
| H2122 | Solid-human lung adenocarcinoma; G12C KRAS mutation; Q16L and C176F P53 mutations | 1.19 | 0.21 |
| H23 | Solid-Human lung adenocarcinoma; G12c KRAS mutation; M2461 P53 mutation | 0.12 | 0.05 |
| H2444 | Solid-human lung adenocarcinoma; G12V KRAS mutation | 0.31 | 0.03 |
| H3255 | Solid-Human lung adenocarcinoma; L858R EGFR mutation; wild-type KRAS; wild-type P53 | 0.21 | 0.07 |
| H358 | Solid-Human lung adenocarcinoma; G13C KRAS mutation | 0.21 | 0.05 |
| H460 | Solid-human lung adenocarcinoma; Q61H KRAS mutation | 0.39 | 0.08 |
| H820 | Solid-human lung adenocarcinoma; Del E746-E749 and T790M EGFR mutations | 0.09 | 0.05 |
| HCC4011 | Solid-Human lung adenocarcinoma; L858R EGFR mutation; wild-type KRAS | 0.14 | 0.05 |
| HCC827 | Solid-human lung adenocarcinoma; DelE746-A750 EGFR mutation | 0.28 | 0.12 |
| HELA N10 | Solid-human cervical adenocarcinoma (positive for human papillomavirus infection) | 1.27 | 0.97 |
| HPLD1 | Solid-Immortalized human bronchiolar epithelial cell with SV-40 Large T antigen | 0.18 | 0.04 |
| HTB15 | Solid-Human Glioblastoma (U-118MG), classified as Grade IV | 0.65 | 0.46 |
| JNDSRCT1 | Solid-Human desmoplastic small round cell tumor cell line | 0.07 | 0.05 |
| MCF-10A | Solid-human normal mammary epithelium | 0.26 | 0.24 |
| MCF-7 | Solid-human invasive breast ductal carcinoma, estrogen and progesterone receptor positive | 0.17 | 0.13 |
| MDA-MB-231 | Solid-human metastatic breast adenocarcinoma; estrogen, progesterone, and HER2/NEU receptor negative | 0.47 | 0.29 |

TABLE 2-continued

| | | IC$_{50}$ (microM) | |
|---|---|---|---|
| Cell Line | Description | Granaticin A | Granaticin B |
| MESO47 | Solid-human mesothelioma; WT-1 overexpression | 0.61 | 0.38 |
| OVCAR3 | Solid-human ovarian adenocarcinoma | 0.21 | 0.11 |
| PC9 | Solid-Human lung adenocarcinoma; DelE746-A750 EGFR mutation | 0.30 | 0.07 |
| RB355 | Solid-Human retinoblastoma | 0.09 | 0.04 |
| RH30 | Solid-Human rhabdomyosarcoma; P53 mutation | 0.13 | 0.08 |
| SKMEL28 | Solid-Human melanoma | 0.54 | 0.34 |
| SKOV3 | Solid-Human adenocarcinoma from the ovary derived from ascites; hypodiploid | 0.12 | 0.04 |
| SW1736 | Solid-Human anaplastic thyroid carcinoma with BRAF V600E mutation | 0.16 | 0.02 |
| TC71 | Solid-Human Ewing's sarcoma | 0.15 | 0.09 |
| Y79 | Solid-Human retinoblastoma | 0.06 | 0.05 |

Example 3. Stability Studies Using Granaticin A

Standard liver microsome stability tests were performed with mouse and human microsomes with granaticin A and revealed that this drug is cleared quickly by the liver. The stability of granaticin A was determined in mouse and human liver microsomes. In mouse liver microsomes, recovery at 30 minutes was 3.68%. In mouse liver microsomes, recovery at 60 minutes was 3.84%. In human liver microsomes, recovery at 30 minutes was 23.88%. In human liver microsomes, recovery at 60 minutes was 12.01%.

Example 4. Preliminary Screening of Granaticin B

Standard solubility studies were conducted with granaticin B. In aqueous solution, 4.0 mg/ml of granaticin B is soluble. In alcohol, >188 mg/ml of granaticin B is soluble. In methanol, >252 mg/ml of granaticin B is soluble.

Different formulations of granaticin B were also tested and PK data measured (see Table 3).

TABLE 3

| Preliminary Mouse PK Screening | | | | |
|---|---|---|---|---|
| Granaticin B, Mouse PK screening 5 mg/kg | AUC$_{inf}$ (hr - µ/mL) | Half-life (t$_{2/1}^\beta$) | C$_{max}$ (µg/mL) | CL (mL/hr/kg) |
| A: 1.25% of Ethanol & Tween-20 | 3532.5 | 6.9 | 2834.7 | 1415.4 |
| B: 0.6% GDO-12 | 477981.5 | 3445.5 | 2537.2 | 10.5 |
| C: 5% GDP-12 | 2689.9 | 6.6 | 2449.9 | 1858.8 |
| D: DMSO | 2724.5 | 2.1 | 2210.9 | 1835.2 |

OTHER EMBODIMENTS

All patents, patent applications, and literature references cited herein are incorporated herein by reference.

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:
1. A compound of Formula (A) or (B):

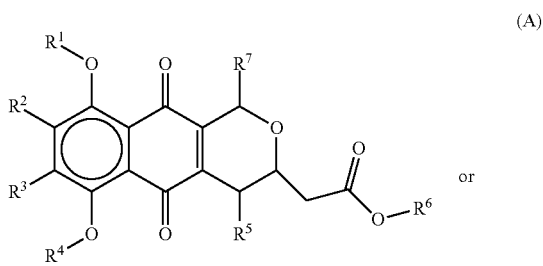

(A)

or

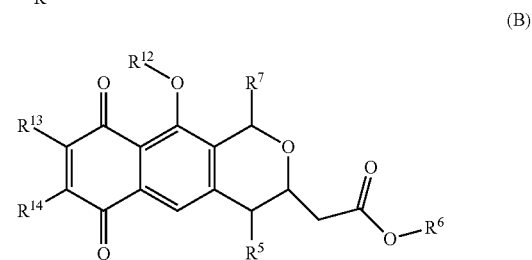

(B)

or a pharmaceutically acceptable salt thereof,
wherein:
each instance of $R^1$ and $R^4$ is independently selected from the group consisting of hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl;
each instance of $R^2$ and $R^3$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^2$ and $R^3$ are joined to form an optionally substituted carbocyclyl, optionally substituted heterocyclyl, optionally substituted aryl, or optionally substituted heteroaryl group;
$R^5$ is hydrogen and $R^6$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl; or $R^5$ and $R^6$ are joined to form a direct bond;
$R^7$ is hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl;

$R^{12}$ is carbonyl, silyl, optionally substituted alkenyl, optionally substituted alkynyl, optionally substituted carbocyclyl, optionally substituted heterocyclyl, optionally substituted aryl, optionally substituted heteroaryl; and each instance of $R^{13}$ and $R^{14}$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^{13}$ and $R^{14}$ are joined to form an optionally substituted carbocyclyl, optionally substituted heterocyclyl, optionally substituted aryl, or optionally substituted heteroaryl group;

with the proviso that the compound cannot be:

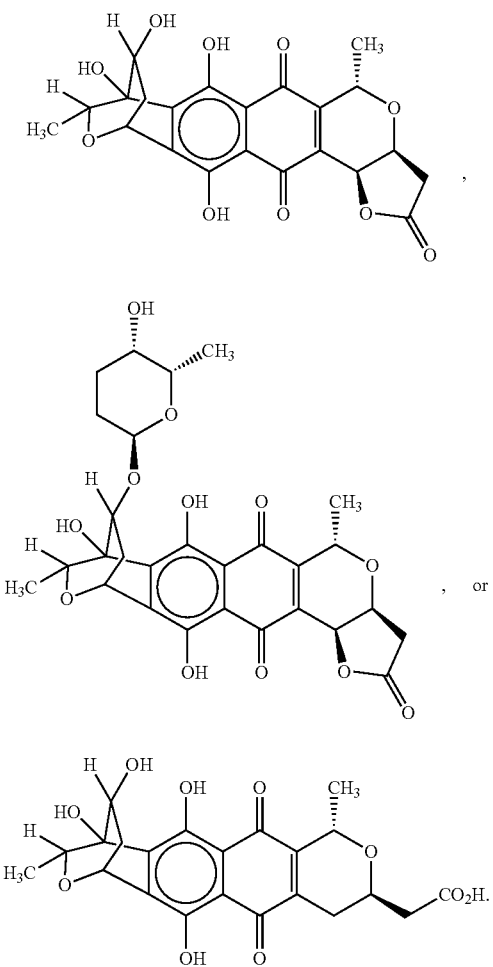

2. A pharmaceutical composition for treating a proliferative disorder comprising a pharmaceutically acceptable excipient and a compound of the Formula (A) or (B):

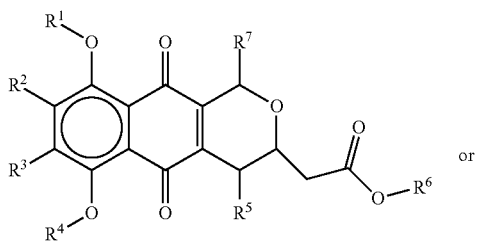

or

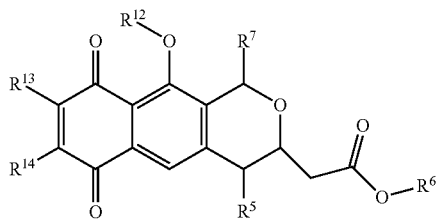

or a pharmaceutically acceptable salt thereof, wherein:

each instance of $R^1$ and $R^4$ is independently selected from the group consisting of hydrogen, carbonyl, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl;

each instance of $R^2$ and $R^3$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^2$ and $R^3$ are joined to form an optionally substituted carbocyclyl, optionally substituted heterocyclyl, optionally substituted aryl, or optionally substituted heteroaryl group;

$R^5$ is hydrogen and $R^6$ is selected from the group consisting of hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl; or $R^5$ and $R^6$ are joined to form a direct bond;

$R^7$ is hydrogen, optionally substituted alkyl, optionally substituted alkenyl, optionally substituted alkynyl, optionally substituted carbocyclyl, optionally substituted heterocyclyl, optionally substituted aryl, and optionally substituted heteroaryl;

$R^{12}$ is carbonyl, silyl, optionally substituted alkenyl, optionally substituted alkynyl, optionally substituted carbocyclyl, optionally substituted heterocyclyl, optionally substituted aryl, optionally substituted heteroaryl; and each instance of $R^{13}$ and $R^{14}$ is independently selected from the group consisting of hydrogen, halogen, —OH, substituted hydroxyl, —SH, substituted thiol, —NH$_2$, substituted amino, —CN, —NO$_2$, carbonyl, silyl, sulfinyl, sulfonyl, optionally substituted alkyl, optionally substituted alkenyl, optionally substituted alkynyl, optionally substituted carbocyclyl, optionally substituted heterocyclyl, optionally substituted aryl, and optionally substituted heteroaryl; or $R^{13}$ and $R^{14}$ are joined to form an optionally substituted carbocyclyl, optionally substituted heterocyclyl, optionally substituted aryl, or optionally substituted heteroaryl group;

with the proviso that the compound cannot be:

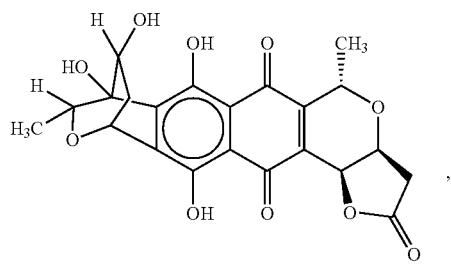

,

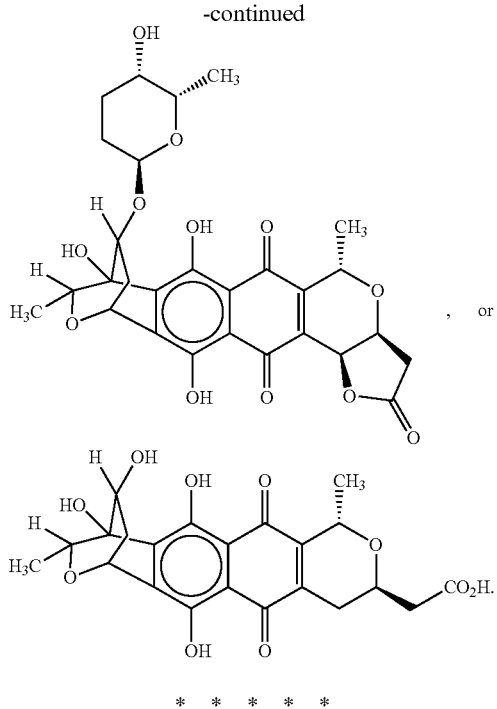

, or

* * * * *